(12) United States Patent
Murphy et al.

(10) Patent No.: US 11,589,562 B2
(45) Date of Patent: Feb. 28, 2023

(54) MOUSE MODEL OF DITRA DISEASE AND USES THEREOF

(71) Applicant: Regeneron Pharmaceuticals, Inc., Tarrytown, NY (US)

(72) Inventors: Andrew J. Murphy, Croton-on-Hudson, NY (US); Alexander O. Mujica, Elmsford, NY (US); Ka-Man Venus Lai, Seattle, WA (US); Sokol Haxhinasto, Brookfield, CT (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 362 days.

(21) Appl. No.: 16/512,949

(22) Filed: Jul. 16, 2019

(65) Prior Publication Data

US 2020/0015462 A1  Jan. 16, 2020

Related U.S. Application Data

(60) Provisional application No. 62/867,477, filed on Jun. 27, 2019, provisional application No. 62/698,459, filed on Jul. 16, 2018.

(51) Int. Cl.
| | |
|---|---|
| *A01K 67/027* | (2006.01) |
| *C07K 16/24* | (2006.01) |
| *C07K 16/28* | (2006.01) |
| *C12N 15/85* | (2006.01) |

(52) U.S. Cl.
CPC ........ *A01K 67/0278* (2013.01); *C07K 16/244* (2013.01); *C07K 16/2866* (2013.01); *C12N 15/8509* (2013.01); *A01K 2207/15* (2013.01); *A01K 2217/072* (2013.01); *A01K 2217/15* (2013.01); *A01K 2227/105* (2013.01); *A01K 2267/0368* (2013.01); *C07K 2317/24* (2013.01); *C07K 2317/76* (2013.01); *C12N 2015/8527* (2013.01)

(58) Field of Classification Search
None
See application file for complete search history.

(56) References Cited

U.S. PATENT DOCUMENTS

| | | | |
|---|---|---|---|
| 6,586,251 | B2 | 7/2003 | Economides et al. |
| 7,294,754 | B2 | 11/2007 | Poueymirou et al. |
| 7,576,259 | B2 | 8/2009 | Poueymirou et al. |
| 7,659,442 | B2 | 2/2010 | Poueymirou et al. |
| 2008/0078000 | A1 | 3/2008 | Poueymirou et al. |
| 2011/0200982 | A1 | 8/2011 | Stevens et al. |
| 2013/0042330 | A1 | 2/2013 | Murphy et al. |
| 2013/0111616 | A1 | 5/2013 | Macdonald et al. |
| 2013/0111617 | A1 | 5/2013 | Macdonald et al. |
| 2013/0117873 | A1 | 5/2013 | Wang et al. |
| 2013/0340104 | A1 | 12/2013 | Murphy |
| 2014/0134662 | A1 | 5/2014 | Flavell et al. |
| 2014/0235933 | A1 | 8/2014 | Lee et al. |
| 2014/0245466 | A1 | 8/2014 | Macdonald et al. |
| 2014/0245467 | A1 | 8/2014 | Macdonald et al. |
| 2014/0310828 | A1 | 10/2014 | Lee et al. |
| 2015/0089678 | A1 | 3/2015 | Murphy et al. |
| 2015/0106961 | A1 | 4/2015 | Rojas et al. |
| 2015/0143558 | A1 | 5/2015 | McWhirter et al. |
| 2015/0143559 | A1 | 5/2015 | McWhirter et al. |
| 2015/0208622 | A1 | 7/2015 | Flavell et al. |
| 2015/0282463 | A1 | 10/2015 | Murphy et al. |
| 2015/0313194 | A1 | 11/2015 | Hu et al. |
| 2015/0320021 | A1 | 11/2015 | Wang et al. |
| 2015/0327524 | A1 | 11/2015 | Murphy et al. |
| 2015/0342163 | A1 | 12/2015 | Voronina et al. |
| 2015/0366174 | A1 | 12/2015 | Burova et al. |
| 2016/0157469 | A1 | 6/2016 | Burova et al. |
| 2016/0295844 | A1 | 10/2016 | Herndler-Brandstetter et al. |
| 2016/0345549 | A1 | 12/2016 | Gurer et al. |
| 2017/0142943 | A1 | 5/2017 | Mujica et al. |
| 2017/0164588 | A1 | 6/2017 | Olson et al. |
| 2017/0245481 | A1 | 8/2017 | Gusarova et al. |
| 2017/0245482 | A1 | 8/2017 | Purcell et al. |
| 2018/0139940 | A1 | 5/2018 | Macdonald et al. |
| 2018/0243450 | A1 | 8/2018 | Devalaraja-Narashimha et al. |
| 2019/0098879 | A1 | 4/2019 | Drummond-Samuelson et al. |
| 2019/0159436 | A1 | 5/2019 | Mujica et al. |
| 2019/0290783 | A1 | 9/2019 | Momont et al. |

FOREIGN PATENT DOCUMENTS

| | | |
|---|---|---|
| CN | 101031316 A | 9/2007 |
| CN | 101522716 A | 9/2009 |
| CN | 104784688 A | 7/2015 |
| RU | 2 425 880 C2 | 2/2011 |
| WO | 2013/063556 A1 | 5/2013 |
| WO | 2013/074569 A1 | 5/2013 |
| WO | 2014/039782 A2 | 3/2014 |
| WO | 2015/171861 A1 | 11/2015 |
| WO | 2016/085889 A1 | 6/2016 |
| WO | 2016/164492 A2 | 10/2016 |

OTHER PUBLICATIONS

Boutet (Clinical & Exp. Immunol., 2016, vol. 184, p. 159-173).*
Cowen E.W. et al., "DIRA, DITRA, and New Insights into Pathways of Skin Inflammation: What's in a Name?", Arch Dermatol. 148(3):381-384 (Mar. 2012).

(Continued)

*Primary Examiner* — Michael C Wilson
(74) *Attorney, Agent, or Firm* — Scully, Scott, Murphy & Presser, P.C.; Elysa Goldberg

(57) ABSTRACT

This disclosure relates to genetically modified rodent animals and rodent models of human diseases. More specifically, this disclosure relates to genetically modified rodents whose genome comprises a humanized Il1rl2 gene (coding for the IL1rl2 subunit of the IL-36R protein) and human IL-36α, β and γ ligand genes. The genetically modified rodents disclosed herein display enhanced skin and intestinal inflammation as a preclinical model of psoriasis and IBD, respectively, and serve as a rodent model of human DITRA disease.

27 Claims, 19 Drawing Sheets
(6 of 19 Drawing Sheet(s) Filed in Color)

Specification includes a Sequence Listing.

(56) References Cited

OTHER PUBLICATIONS

Shibata A. et al., "Toll-Like Receptor 4 Antagonist TAK-242 Inhibits Autoinflammatory Symptoms in DITRA", Journal of Autoimmunity 80:28-38 (Feb. 11, 2017).
Zhou L. et al., "Quantitative Ligand and Receptor Binding Studies Reveal the Mechanism of Interleukin-36 (IL-36) Pathway Activation", Journal of Biological Chemistry 293(2):403-411 (Nov. 27, 2017).
International Search Report and Written Opinion dated Sep. 27, 2019 received in International Application No. PCT/US2019/041964.
Bissonnette R. et al., "Based on Molecular Profiling of Gene Expression, Palmoplantar Pustulosis and Palmoplantar Pustular Psoriasis are Highly Related Diseases that Appear to be Distinct from Psoriasis Vulgaris", PLoS One 11(5):1-11 (May 6, 2016).
Boutet M-A et al., "Distinct Expression of Interleukin (IL)-36α, β and ?, Their Antagonist IL-36Ra and IL-38 in Psoriasis, Rheumatoid Arthritis and Crohn's Disease", Clinical & Experimental Immunology 184:159-173 (2016).
Chen H. et al., "Alterations of Plasma Inflammatory Biomarkers in the Healthy and Chronic Obstructive Pulmonary Disease Patients With or Without Acute Exacerbation", Journal of Proteomics 75:2835-2843 (2012).
D'Erme A M et al., "IL-36y (IL-1F9) is a Biomarker for Psoriasis Skin Lesions", Journal of Investigative Dermatology 135:1025-1032 (2015).
Frey S. et al., "The Novel Cytokine Interleukin-36α is Expressed in Psoriatic and Rheumatoid Arthritis Synovium", Ann Rheum Dis 72:1569-1574 (2013).
Garlanda C. et al., "The Interleukin-1 Family: Back to the Future", Immunity 39:1003-1018 (Dec. 12, 2013).
Harari D. et al., Bridging the Species Divide: Transgenic Mice Humanized for Type-I Interferon Response, PLoS One 9(1):1-12 (Jan. 2014).
Harusato A. et al., "IL-36y Signaling Controls the Induced Regulatory T Cell-Th9 Cell Balance Via NFκB Activation and STAT Transcription Factors", Mucosal Immunology 10:1455-1467 (2017).
Heller F. et al., "Oxazolone Colitis, a Th2 Colitis Model Resembling Ulcerative Colitis, is Mediated by IL-13-Producing NK-T Cells", Immunity 17:629-638 (Nov. 2002).
Johnston A. et al., "IL-1 and IL-36 are Dominant Cytokines in Generalized Pustular Psoriasis", J Allergy Clin Immunol 140(1):109-120 (Jul. 2017).
Mahil S.K. et al., "An Analysis of IL-36 Signature Genes and Individuals with IL1RL2 Knockout Mutations Validates IL-36 as a Psoriasis Therapeutic Target", Sci. Transl. Med. 9:1-11 (Oct. 11, 2017.
Marrakchi S. et al., "Interieukin-36-Receptor Antagonist Deficiency and Generalized Pustular Psoriasis", The New England Journal of Medicine 365(7):620-628 (Aug. 18, 2011).
Medina-Contreras O. et al., "Cutting Edge: IL-36 Receptor Promotes Resolution of Intestinal Damage", The Journal of Immunology 196:34-38 (2016).
Nishida A. et al., "Increased Expression of Interleukin-36δ, a Member of the Interleukin-1 Cytokine Family, in Inflammatory Bowel Disease", Inflamm Bowel Dis 22(2):303-314 (Feb. 2016).
Okayasu I. et al., "A Novel Method in the Induction of Reliable Experimental Actue and Chronic Ulcerative Colitis in Mice", Gastroenterology 98(3):694-702 (1990).
Onoufriadis A. et al., "Mutations in IL36RN/IL1F5 are Associated With the Severe Episodic Inflammatory Skin Disease Known as Generalized Pustular Psoriasis", The American Journal of Human Genetics 89:432-437 (Sep. 9, 2011).
Paller A.S. et al., "An IL-17-Dominant Immune Profile is Shared Across the Major Orphan Forms of Ichthyosis", J Allergy Clin Immunol 139:152-165 (2017).
Poueymirou W T et al., "F0 Generation Mice Fully Derived from Gene-Targeted Embryonic Stem Cells Allowing Immediate Phenotypic Analyses", Nature Biotechnology 25(1):91-99 (Jan. 2007).

Rakoff-Nahoum S. et al., "Recognition of Commensal Microflora by Toll-Like Receptors is Required for Intestinal Homeostatis", Cell 118:229-241 (Jul. 23, 2004).
Russell SE et al., "IL-36α Expression is Elevated in Ulcerative Colitis and Promotes Colonic Inflammation", Mucosal Immunology 9(5):1193-1204 (Sep. 2016).
Shaik Y. et al., "IL-36 Receptor Antagonist With Special Emphasis on IL-38", International Journal of Immunopathology and Pharmacology 26(1):27-36 (2013).
Swindell et al., "Genome-Wide Expression Profiling of Five Mouse Models Identifies Similarities and Differences With Human Psoriasis", PLoS One 6(4):e18266 (Apr. 2011).
Thorsvik S. et al., "Fecal Neurophil Gelatinase-Associated Lipocalin as a Biomarker for Inflammatory Bowel Disease", Journal of Gastroenterology and Hepatology 32: 128-135 (2017).
Tong C. et al., "Generating Gene Knockout Rats by Homologous Recombination in Embryonic Stem Cells", Nat Protoc 6(6):doi:10. 1038/nprot.2011.338 (Jun. 2011).
Tong C. et al., "Production of p53 Gene Knockout Rats by Homologous Recombination in Embryonic Stem Cells", Nature 467:211-215 (Sep. 9, 2010).
Tortola L. et al., "Psoriasiform Dermatitis is Driven by IL-36-Mediated DC-Keratinocyte Crosstalk", The Journal of Clinical Investigation 122(11):3965-3976 (Nov. 2012).
Towne J.E. et al., "Interleukin (IL)-1F6, IL-1F8, and IL-1F9 Signal Through IL-1Rrp2 and IL-1RAcP to Activate the Pathway Leading to NF-κB and MAPKs", The Journal of Biological Chemistry 279(14):13677-13688 (Apr. 2, 2004).
Towne JE et al., "IL-36 in Psoriasis", Current Opinion in Pharmacology 12:486-490 (2012).
Valenzuela D M et al., "High-Throughput Engineering of the Mouse Genome Coupled With High-Resolution Expression Analysis", Nature Biotechnology 21(6):652-659 (Jun. 2003).
Van Der Fits L. et al., "Imiquimod-Induced Psoriasis-Like Skin Inflammation in Mice is Mediated Via the IL-23/IL-17 Axis", The Journal of Immunology 182:5836-5845 (2009).
NCBI Reference Sequence No. NM_014440.2 (4 pages) (May 4, 2019).
NCBI Reference Sequence No. NM_001106554.1 (2 pages) (May 28, 2018).
NCBI Reference Sequence No. NM_019450.3 (4 pages) (Jun. 2, 2019).
NCBI Reference Sequence No. NM_014438.4 (4 pages) (May 4, 2019).
NCBI Reference Sequence No. NM_001108570.1 (2 pages) (May 28, 2018).
NCBI Reference Sequence No. NM_027163.4 (3 pages) (Jun. 4, 2019).
NCBI Reference Sequence No. NM_001113790.1 (2 pages) (May 28, 2018).
NCBI Reference Sequence No. NM_153511.3 (4 pages) (Sep. 21, 2019).
NCBI Reference Sequence No. NM_019618.3 (4 pages) (Oct. 28, 2018).
NCBI Reference Sequence No. NM_133575.1 (4 pages) (Sep. 21, 2019).
NCBI Reference Sequence No. NM_133193.4 (6 pages) (Feb. 27, 2019).
NCBI Reference Sequence No. NM_003854.3 (5 pages) (Jul. 1, 2018).
NCBI Reference Sequence No. NP_055255.1 (3 pages) (Sep. 27, 2019).
NCBI Reference Sequence No. NP_573456.1 (4 pages) (Feb. 27, 2019).
NCBI Reference Sequence No. NP_062323.1 (3 pages) (Jun. 2, 2019).
NCBI Reference Sequence No. NP_001100024.1 (2 pages) (May 28, 2018).
NCBI Reference Sequence No. NP_055253.2 (3 pages) (Jun. 30, 2019).
NCBI Reference Sequence No. NP_081439.1 (3 pages) (Jun. 4, 2019).

(56) References Cited

OTHER PUBLICATIONS

NCBI Reference Sequence No. NP_001107262.1 (2 pages) (May 28, 2018).
NCBI Reference Sequence No. NP_062564.1 (3 pages) (Aug. 27, 2019).
NCBI Reference Sequence No. NP_003845.2 (4 pages) (Sep. 27, 2019).
NCBI Reference Sequence No. NP_598259.1 (3 pages) (Sep. 21, 2019).
NCBI Reference Sequence No. XP_006233676.1 (2 pages) (Jul. 26, 2016).
UniProtKB/Swiss-Prot No. Q8R460.1 (3 pages) (Sep. 18, 2019).
Chinese Office Action dated Mar. 3, 2022 received in Chinese Application No. 201980040953.1, together with an English-language translation.
Shibata A. et al., "Toll-Like Receptor 4 Antagonist TAK-242 Inhibits Autoinflammatory Symptoms in DITRA", Journal of Autoimmunity 80:28-38 (2017).
European Communication dated Apr. 28, 2022 received in European Application No. 19 749 891.8.
Dennis, Jr. M.B., "Welfare Issues of Genetically Modified Animals", ILAR Journal 43(2):100-109 (2002).
Glick B. et al., Moleculyarnaya Biotehnologiya. Printsipy i primeneniye. Moscow: Mir, 2002, together with an English-language translation.
Zhou H. et al., "Developing tTA Transgenic Rats for Inducible and Reversible Gene Expression", International Journal of Biological Sciences 5(2):171-181 (2009).
Russian Office Action & Search Report dated Oct. 3, 2022 received in Russian Application No. 2020135272/10 (664988), together with an English-language translation.

\* cited by examiner

FIG. 1D

Il1f6 protein alignment

```
Mouse Il1f6    1   MNKEKERAASPSLRHVQDLSSRVWILQNNILTAVPRKEQTVPVTITLLPCQYLDTLETN   60
human IL1F6    1   ..MEKALKIDTPQQGSIQDINHRVWVLQDQTLIAVPRKDRMSPVTIALISCRHVETLEKD  58

Mouse Il1f6   61   RGDPTYMGVQRPMSCLFCTKDGEQPVLQLGEGNIMEMYNKKEPVKASLFYHKISGTTSTF 120
human IL1F6   59   RGNPIYLGLNGLNLCLMCAKVGDQPTLQLKEKDIMDLYNQPEPVKSFLFYHSQSGRNSTF 118

Mouse Il1f6  121   ESAAFPGWFIAVCSKGSCPLLITQELGEIFITDFEMIVVH  160    SEQ ID NO: 11
human IL1F6  119   ESVAFPGWFIAVSSEGGCPLLITQELGKANTIDFGLTMLF  158    SEQ ID NO: 9
```

Il1f8 protein alignment

```
Mouse Il1f8    1   MMAFPPQSCVHVLPPKSIQMWEPNHNTMHGSSQSPRNYRVHDSQQMVWVLTGNTLTAVPA   60
human IL1F8    1   ...MNPQ.........................REAAPKSYAIRDSRQMVWVLSGNSLIAAPL  34

Mouse Il1f8   61   SNNVKPVILSLIACRDTEFQDVKKGNLVFLGIKNRNLCFCCVEMEGKPTLQLKEVDIMNL 120
human IL1F8   35   SRSIKPVTLHLIACRDTEFSDKEKGNMVYLGIKGKDLCLFCAEIQGKPTLQLKLQGSQDN  94

Mouse Il1f8  121   YKERKAQKAFLFYHGIEGST..SVFQSVLYPGWFIATSSIERQTIILTHQRGKLVNTNFY 178
human IL1F8   95   IGKDTCWKLVGIHTCINLDVRESCFMGTLDQ.MGIGVGRKKWKSSFQHHHLRKKDKDFSS 153

Mouse Il1f8  179   IESEK......  183    SEQ ID NO: 17
human IL1F8  154   MRTNIGMPGRM  164    SEQ ID NO: 15
```

FIG. 2D

Il1f9 protein alignment

```
Mouse Il1f9   1   MFSKHPFS....THISGRETPDFGEVFDLDQQVWIFRNQALVTVPRSHRVTPVS      55
human IL1F9   1   MRGTPGDADGGGRAVYQSMCKPITGTINDLNQQVWTLQGQNLVAVPRSDSVTPVT      60

Mouse Il1f9  56   CKYPESLEQDKGIAIYLGIQNPDKCLFCKEVNGHPTLLKEEKILDLYHHPEPMKPFLFY  115
human IL1F9  61   CKYPEALEQGRGDPIYLGIQNPEMCLYCEKVGEQPTLQLKEQKIMDLYGQPEPVKPFLFY 120

Mouse Il1f9 116   HTRTGGTSTFESVAFPGHYIASSKTGNPIFLTSKKGEYNINFNLDIKS              164  SEQ ID NO: 23
human IL1F9 121   RAKTGRTSTLESVAFPDWFIASSKRDQPILTSELGKSYNTAFELNND              169  SEQ ID NO: 21
```

FIG. 2D (continued)

SEQUENCE LISTING

```
<160> NUMBER OF SEQ ID NOS: 57

<210> SEQ ID NO 1
<211> LENGTH: 2628
<212> TYPE: DNA
<213> ORGANISM: Homo sapiens

<400> SEQUENCE: 1
cccgcccacg gtggcgggga aatacctagg catggaagtg gcatgacagg gctcgtgtcc      60
ctgtcatatt ttccactctc cacgaggtcc tgcgcgcttc aatcctgcag gcagcccggt     120
ttggggatgt ggtccttgct gctctgcggg ttgtccatcg cccttccact gtctgtcaca     180
gcagatggat gcaaggacat ttttatgaaa aatgagatac tttcagcaag ccagccttt      240 gcttttaatt gtacattccc tcccataaca tctggggaag tcagtgtaac atggtataaa     300
aattctagca aaatcccagt gtccaaaatc atacagtcta gaattcacca ggacgagact     360
tggattttgt ttctccccat ggaatggggg gactcaggag tctaccaatg tgttataaag     420
ggtagagaca gctgtcatag aatacatgta aacctaactg ttttttgaaaa acattggtgt    480 gacacttcca taggtggttt accaaattta tcagatgagt acaagcaaat attacatctt    540
ggaaaagatg atagtctcac atgtcatctg cacttcccga agagttgtgt tttgggtcca    600
ataaagtggg ataaggactg taacgagatt aaagggggagc ggttcactgt tttggaaacc   660
aggcttttgg tgagcaatgt ctcggcagag gacagaggga actacgcgtg tcaagccata   720
ctgacacact cagggaagca gtacgaggtt ttaaatggca tcactgtgag cattacagaa   780
agagctggat atggaggaag tgtccctaaa atcatttatc caaaaaatca ttcaattgaa   840
gtacagcttg gtaccactct gattgtggac tgcaatgtaa cagacaccaa ggataataca   900
aatctacgat gctggagagt caataacact ttggtggatg attactatga tgaatccaaa   960
cgaatcagag aagggtgga aacccatgtc tcttttcggg aacataattt gtacacagta   1020
aacatcacct tcttggaagt gaaaatggaa gattatggcc ttccttcat gtgccacgct   1080 ggagtgtcca cagcatacat tatattacag ctcccagctc cggattttcg agcttacttg   1140
ataggagggc ttatcgcctt ggtggctgtg gctgtgtctg ttgtgtacat atacaacatt   1200
tttaagatcg acattgttct ttggtatcga agtgccttcc attctacaga gaccatagta   1260
gatgggaagc tgtatgacgc ctatgtctta taccccaagc cccacaagga aagccagagg   1320
catgccgtgg atgccctggt gttgaatatc ctgcccgagg tgttggagag acaatgtgga   1380
tataagttgt ttattcgg cagagatgaa ttccctggac aagccgtggc caatgtcatc   1440
```

```
gatgaaaacg ttaagctgtg caggaggctg attgtcattg tggtccccga atcgctgggc    1500
tttggcctgt tgaagaacct gtcagaagaa caaatcgcgg tctacagtgc cctgatccag    1560
gacgggatga aggttattct cattgagctg gagaaaatcg aggactacac agtcatgcca    1620
gagtcaattc agtacatcaa acagaagcat ggtgccatcc ggtggcatgg ggacttcacg    1680
gagcagtcac agtgtatgaa gaccaagttt tggaagacag tgagatacca catgccgccc    1740
agaaggtgtc ggccgtttcc tccggtccag ctgctgcagc acacaccttg ctaccgcacc    1800
gcaggcccag aactaggctc aagaagaaag aagtgtactc tcacgactgg ctaagacttg    1860
ctggactgac acctatggct ggaagatgac ttgttttgct ccatgtctcc tcattcctac    1920
acctattttc tgctgcagga tgaggctagg gttagcattc tagacaccca gttgagctca    1980
ggcgtagaga agaggaggat gggataagaa ctggggccat ccccatgtca tggtgggtga    2040
gagctggggc catccccgtg gtcatggagg gtgagagctg ggggttatcc ccatggtcat    2100
ggagggtgag ggctggtcgg gggaggcatc cccaagtcat ggtgggtgag agctcggagc    2160
atccccatgt catggtgggt gagatctggg ggtatccctg tgtcatggtg ggtgagggcg    2220
ggtggtcatc cacatggtca tagtgggtga gagctggggg tatccctaca tcatggtggg    2280
tgagagctgg gagcatcccc atgtcatggt gggcgagatc tgggggggtat ccccacgtca    2340 tggtggatga gagctggggg aatcaccatg tcatggtggg tgagatcttg ggggatcacc    2400
tgtcatggtg ggtgagagct gggggggatca cctgtcatgg tgggtgagag ttgggattca    2460
tccccatgtc atggtgggct gagcccacat ggaagcctgt gcttggacag cgtatgccct    2520
tttctctgtt tttccacaat gaacaattaa actgtaaatg ttaaaaatat cagtaatttg    2580
tgaaataaat tttattctca tttgagcaac ataaaaaaaa aaaaaaaa                 2628
```

<210> SEQ ID NO 2
<211> LENGTH: 575
<212> TYPE: PRT
<213> ORGANISM: Homo sapiens

<400> SEQUENCE: 2

```
Met Trp Ser Leu Leu Leu Cys Gly Leu Ser Ile Ala Leu Pro Leu Ser
1               5                   10                  15

Val Thr Ala Asp Gly Cys Lys Asp Ile Phe Met Lys Asn Glu Ile Leu
            20                  25                  30

Ser Ala Ser Gln Pro Phe Ala Phe Asn Cys Thr Phe Pro Pro Ile Thr
        35                  40                  45

Ser Gly Glu Val Ser Val Thr Trp Tyr Lys Asn Ser Ser Lys Ile Pro
    50                  55                  60

Val Ser Lys Ile Ile Gln Ser Arg Ile His Gln Asp Glu Thr Trp Ile
65                  70                  75                  80

Leu Phe Leu Pro Met Glu Trp Gly Asp Ser Gly Val Tyr Gln Cys Val
                85                  90                  95

Ile Lys Gly Arg Asp Ser Cys His Arg Ile His Val Asn Leu Thr Val
            100                 105                 110

Phe Glu Lys His Trp Cys Asp Thr Ser Ile Gly Gly Leu Pro Asn Leu
        115                 120                 125

Ser Asp Glu Tyr Lys Gln Ile Leu His Leu Gly Lys Asp Asp Ser Leu
    130                 135                 140

Thr Cys His Leu His Phe Pro Lys Ser Cys Val Leu Gly Pro Ile Lys
145                 150                 155                 160
```

```
Trp Tyr Lys Asp Cys Asn Glu Ile Lys Gly Glu Arg Phe Thr Val Leu
            165                 170                 175

Glu Thr Arg Leu Leu Val Ser Asn Val Ser Ala Glu Asp Arg Gly Asn
        180                 185                 190

Tyr Ala Cys Gln Ala Ile Leu Thr His Ser Gly Lys Gln Tyr Glu Val
        195                 200                 205

Leu Asn Gly Ile Thr Val Ser Ile Thr Glu Arg Ala Gly Tyr Gly Gly
    210                 215                 220

Ser Val Pro Lys Ile Ile Tyr Pro Lys Asn His Ser Ile Glu Val Gln
225                 230                 235                 240

Leu Gly Thr Thr Leu Ile Val Asp Cys Asn Val Thr Asp Thr Lys Asp
                245                 250                 255

Asn Thr Asn Leu Arg Cys Trp Arg Val Asn Asn Thr Leu Val Asp Asp
            260                 265                 270

Tyr Tyr Asp Glu Ser Lys Arg Ile Arg Glu Gly Val Glu Thr His Val
        275                 280                 285

Ser Phe Arg Glu His Asn Leu Tyr Thr Val Asn Ile Thr Phe Leu Glu
    290                 295                 300

Val Lys Met Glu Asp Tyr Gly Leu Pro Phe Met Cys His Ala Gly Val
305                 310                 315                 320

Ser Thr Ala Tyr Ile Ile Leu Gln Leu Pro Ala Pro Asp Phe Arg Ala
                325                 330                 335

Tyr Leu Ile Gly Gly Leu Ile Ala Leu Val Ala Val Ala Val Ser Val
            340                 345                 350

Val Tyr Ile Tyr Asn Ile Phe Lys Ile Asp Ile Val Leu Trp Tyr Arg
        355                 360                 365

Ser Ala Phe His Ser Thr Glu Thr Ile Val Asp Gly Lys Leu Tyr Asp
    370                 375                 380

Ala Tyr Val Leu Tyr Pro Lys Pro His Lys Glu Ser Gln Arg His Ala
385                 390                 395                 400

Val Asp Ala Leu Val Leu Asn Ile Leu Pro Glu Val Leu Glu Arg Gln
                405                 410                 415

Cys Gly Tyr Lys Leu Phe Ile Phe Gly Arg Asp Glu Phe Pro Gly Gln
            420                 425                 430

Ala Val Ala Asn Val Ile Asp Glu Asn Val Lys Leu Cys Arg Arg Leu
        435                 440                 445

Ile Val Ile Val Val Pro Glu Ser Leu Gly Phe Gly Leu Leu Lys Asn
    450                 455                 460

Leu Ser Glu Glu Gln Ile Ala Val Tyr Ser Ala Leu Ile Gln Asp Gly
465                 470                 475                 480

Met Lys Val Ile Leu Ile Glu Leu Glu Lys Ile Glu Asp Tyr Thr Val
                485                 490                 495

Met Pro Glu Ser Ile Gln Tyr Ile Lys Gln Lys His Gly Ala Ile Arg
            500                 505                 510

Trp His Gly Asp Phe Thr Glu Gln Ser Gln Cys Met Lys Thr Lys Phe
        515                 520                 525

Trp Lys Thr Val Arg Tyr His Met Pro Pro Arg Arg Cys Arg Pro Phe
    530                 535                 540

Pro Pro Val Gln Leu Leu Gln His Thr Pro Cys Tyr Arg Thr Ala Gly
545                 550                 555                 560

Pro Glu Leu Gly Ser Arg Arg Lys Lys Cys Thr Leu Thr Thr Gly
                565                 570                 575
```

<210> SEQ ID NO 3
<211> LENGTH: 4072
<212> TYPE: DNA
<213> ORGANISM: Mus musculus

<400> SEQUENCE: 3

| | | | | | |
|---|---|---|---|---|---|
| ggcggacaga | gaccggaagc | tgggagatga | tggcttctga | tgtttgttgc | ttacgcgaca | 60 |
| cagcttgttt | ggaattatgt | ggcccttgac | aactgcgtgg | cacacacttc | aagatacaaa | 120 |
| agtgagaaga | agaggggggt | caccagagga | gactgaagtc | agtaagtttc | taccaaagct | 180 |
| gggtttcttc | tggccactcc | aaacaaagct | gaaattgtcc | ttcagacctc | tcctgagatg | 240 |
| ggggttacat | ctttgctctt | ctgtggggtg | ttttcctgc | ttctgctttt | cgtggcagca | 300 |
| gatacgtgtg | aggacatttt | tatgcacaat | gtgataattt | cagagggcca | gccttttcct | 360 |
| ttcaactgca | catacccgcc | agaaacaaac | ggggcagtaa | atctgacatg | gtacaaaaca | 420 |
| cctagcaaaa | gcccagtatc | taacaacaga | caccttagag | ttcaccagga | ccagacctgg | 480 |
| atcttgtttc | ttccattgac | actgaggac | tccggtatct | atcagtgtgt | tataaggaat | 540 |
| gcccacaact | gctaccaaat | agctgtgaac | ctaaccgttt | taaaaaacca | ctggtgtgac | 600 |
| tcttccatgg | aggggagtcc | cgtaaattca | ccagatgtgt | accagcaaat | attacccata | 660 |
| ggaaaatcgg | gcagtctgaa | ttgtcatctc | tacttcccag | aaagttgtgc | tttggattca | 720 |
| ataaaatggt | ataagggttg | tgaagagatt | aaagcgggga | aaaagtacag | cccttcagga | 780 |
| gcaaagcttc | ttgtgaacaa | cgttgctgtg | gaggacggcg | ggagctatgc | gtgctcagcc | 840 |
| agactgactc | acttggggag | acacttcacc | attagaaact | acattgctgt | gaacaccaag | 900 |
| gaagttgagt | atggaagaag | gatccctaac | atcacgtatc | caaagaacaa | ctccattgaa | 960 |
| gttccacttg | gctccaccct | catcgtgaac | tgcaatataa | cagacacgaa | ggagaataca | 1020 |
| aacctgaggt | gctggagagt | caacaacacc | ctggtggatg | actactacaa | agactccaaa | 1080 |
| cgcatccagg | aaggaatcga | aaccaatgtg | tccttgaggg | atcaaattcg | gtacacagtg | 1140 |
| aacataacat | tcttaaaagt | gaaaatggag | gactacggcc | gtccttcac | gtgtcatgct | 1200 |
| ggagtgtccg | cagcctacat | cattctgata | tacccagttc | cagacttcag | ggcttacctc | 1260 |
| ttaggagggc | ttatggcgtt | cctacttctg | gttgtatctg | ttctgttcat | ctacaacagc | 1320 |
| tttaagatcg | acatcatgct | ttggtacaga | agcgccttcc | acactgccca | ggctccagat | 1380 |
| gatgagaagc | tgtatgatgc | ctatgtctta | taccccaagt | acccgagagg | aagccagggc | 1440 |
| catgatgtag | acacactggt | actgaagatc | ttgcccgagg | tgctggagaa | acagtgtgga | 1500 |
| tataagttat | ttatatttgg | cagggatgaa | ttccctggac | aagctgtggc | cagcgtcatt | 1560 |
| gatgaaaaca | ttaagctgtg | taggaggctg | atggtctttg | tggcaccaga | gtcgtctagc | 1620 |
| ttcggctttc | taaagaactt | gtcagaagaa | caaattgccg | tctacaatgc | cctcatccag | 1680 |
| catggcatga | aggtcattct | gatcgaactg | gagaaagtca | agactacag | caccatgccc | 1740 |
| gagtccattc | agtatatccg | acagaagcac | ggggccatcc | aatgggatgg | ggacttcaca | 1800 |
| gagcagtcac | agtgtgccaa | gaccaagttc | tggaagaaag | tgagatacca | tatgccaccc | 1860 |
| aggaggtatc | cagcatcttc | cccagtccag | ctgctgggac | acatacccctg | caattgcaag | 1920 |
| gcaggcaaat | gcaatgctgc | cacagggctc | ataactccct | gagagtggtt | agtgtgtgtt | 1980 |
| ggctcacact | acatcctctc | tgaattgtct | actcatgtag | ctggctcttt | tgtgcttgtg | 2040 |
| agcgaccttg | tccttgccct | tgtagctttt | tgttttatttg | tattgtttgc | tggatgcttt | 2100 |
| cagtcatagc | tgatccttat | tactcctgtt | tgcttcatgg | ctcctgaaaa | cccatatact | 2160 |

```
cccaagcat ggggtggctc taacgttggg cctccgtgtc agtgggatac tgaggatgac    2220
agatcaggtg tccaggatgc ttgatcctgg tttgagatgg gaggctgggc agtctgagga    2280
taccaagtag atagccttag ggaagatcag caaggacagt agtgcaatgt ctgtgtttgt    2340
ccagggtcca caagattcta gtcctcaggc agtgtagact gcatttgaat ctccttcatt    2400
ttcctattgc atttagttaa ctaaccattg tgagaacagg acagaggact gggagttggg    2460
ggtgggggga ggtgacagag gatgggagtg tgtgtgtaag aggtgacagt tacatgatca    2520
atcctgggaa atcagactca ggaaaccagc attagggtgc agatctgagt tttttgtgca    2580
gcccttaagc ttatatacag cgttcgagcc aatcccaagc ccctaaaccc tcggccaatc    2640
atatcttgcc acatcatcac tatgcctcaa tgaaagccct gcctgatgag gtaactcaaa    2700
aggaattggg gtgggaagca tcatcccctg tcagaacttc cgtgaagatg gaggacgtag    2760
ccactacccc acctcagttt cttttttgttg tctcaggttt gcaccagagc catcttaaat    2820
ctagtgacat gtgcagcaaa tcatgactct tcaaggagct gcgggagcct gtggtgcctc    2880
gctctccatc ccactttttc cttcacaggg ttgacttcca cgtcccccaa accatggtat    2940
tagcacgatg ccctagaaag ccgcttagat gtcgccagga ccaatggtct tcatttccct    3000
ctttcccagc cctgtgaat cttactattc taggaaattc aaatgagaga cacggtgcat    3060
tcacggtttc tcattttatg actggcttct ttcatacacc acggatttct caagtgctct    3120
cgagattcat ccattgatta gccttttgtt ttattattat cactactgtc tttctcttct    3180
tttttcttcct cttaaattt ctcccctcc tcacgagcat ccggagagga gcatagactc    3240
tctgcatgcc tacagcgtga tgagctcacc gagggtccct tcaatcacaa gcttgtatgt    3300
tttgcttttc ggtttctctt tgcaccatgg gaattgtaac tccttacaga ggatttgaag    3360
gttcgggtac aaaggcgtca ctgactggtt ccttcttctg tcttcctcac cctgaatggg    3420
ctttgcttct gggtgattcc tggaaattgt cagcagtgat ggagaaacct agggacaggg    3480
ctgactaatg gggcctggcc tttcttcttt gaagcccagg acacagtgcc tgcctagtgg    3540
gtcctggaca caccaggtgg ttccactctg ctcagtggta acattttta gctgagtcat    3600
caacatcggg tcctttagtg aggaggtgcg ggcatctctc cccagttaga tttggactct    3660
tacttccctg ctcatttccc tttgaaagat tcaggagact atgtcagaag cagggagcca    3720
gcaccctgtg tcttctccac gtggctcctt gtcacacctg tgaccaccaa ttttagaaaa    3780
tgtgtttcct tgttctgacc acacttatgc ggacattagt tgaggctgtt gtcagaaagg    3840
aaaattaact catttgaagt aaacattttc tggaaatctc tgacttctgt caggccaatg    3900
gtgctgaaaa atttaaaact gaattcactt ttttggccag aaagctttcc tcttgccaac    3960
atgtcttaat tttcctttg cttaaactta ttggagatgt attatgaatg ctaagatgtg    4020
agtgtgttat atcagtacat tgacattta aataaagtat attttaataa aa              4072
```

<210> SEQ ID NO 4
<211> LENGTH: 574
<212> TYPE: PRT
<213> ORGANISM: Mus musculus

<400> SEQUENCE: 4

```
Met Gly Val Thr Ser Leu Leu Phe Cys Gly Val Phe Phe Leu Leu Leu
1               5                   10                  15

Leu Phe Val Ala Ala Asp Thr Cys Glu Asp Ile Phe Met His Asn Val
            20                  25                  30

Ile Ile Ser Glu Gly Gln Pro Phe Pro Phe Asn Cys Thr Tyr Pro Pro
```

```
                35                  40                  45
Glu Thr Asn Gly Ala Val Asn Leu Thr Trp Tyr Lys Thr Pro Ser Lys
 50                  55                  60

Ser Pro Val Ser Asn Asn Arg His Leu Arg Val His Gln Asp Gln Thr
 65                  70                  75                  80

Trp Ile Leu Phe Leu Pro Leu Thr Leu Glu Asp Ser Gly Ile Tyr Gln
                 85                  90                  95

Cys Val Ile Arg Asn Ala His Asn Cys Tyr Gln Ile Ala Val Asn Leu
                100                 105                 110

Thr Val Leu Lys Asn His Trp Cys Asp Ser Ser Met Glu Gly Ser Pro
            115                 120                 125

Val Asn Ser Pro Asp Val Tyr Gln Gln Ile Leu Pro Ile Gly Lys Ser
        130                 135                 140

Gly Ser Leu Asn Cys His Leu Tyr Phe Pro Ser Cys Ala Leu Asp
145                 150                 155                 160

Ser Ile Lys Trp Tyr Lys Gly Cys Glu Ile Lys Ala Gly Lys Lys
                165                 170                 175

Tyr Ser Pro Ser Gly Ala Lys Leu Leu Val Asn Asn Val Ala Val Glu
            180                 185                 190

Asp Gly Gly Ser Tyr Ala Cys Ser Ala Arg Leu Thr His Leu Gly Arg
        195                 200                 205

His Phe Thr Ile Arg Asn Tyr Ile Ala Val Asn Thr Lys Glu Val Glu
    210                 215                 220

Tyr Gly Arg Arg Ile Pro Asn Ile Thr Tyr Pro Lys Asn Asn Ser Ile
225                 230                 235                 240

Glu Val Pro Leu Gly Ser Thr Leu Ile Val Asn Cys Asn Ile Thr Asp
                245                 250                 255

Thr Lys Glu Asn Thr Asn Leu Arg Cys Trp Arg Val Asn Asn Thr Leu
            260                 265                 270

Val Asp Asp Tyr Tyr Lys Asp Ser Lys Arg Ile Gln Glu Gly Ile Glu
        275                 280                 285

Thr Asn Val Ser Leu Arg Asp Gln Ile Arg Tyr Thr Val Asn Ile Thr
    290                 295                 300

Phe Leu Lys Val Lys Met Glu Asp Tyr Gly Arg Pro Phe Thr Cys His
305                 310                 315                 320

Ala Gly Val Ser Ala Ala Tyr Ile Ile Leu Ile Tyr Pro Val Pro Asp
                325                 330                 335

Phe Arg Ala Tyr Leu Leu Gly Gly Leu Met Ala Phe Leu Leu Leu Val
            340                 345                 350

Val Ser Val Leu Phe Ile Tyr Asn Ser Phe Lys Ile Asp Ile Met Leu
        355                 360                 365

Trp Tyr Arg Ser Ala Phe His Thr Ala Gln Ala Pro Asp Glu Lys
    370                 375                 380

Leu Tyr Asp Ala Tyr Val Leu Tyr Pro Lys Tyr Pro Arg Gly Ser Gln
385                 390                 395                 400

Gly His Asp Val Asp Thr Leu Val Leu Lys Ile Leu Pro Glu Val Leu
                405                 410                 415

Glu Lys Gln Cys Gly Tyr Lys Leu Phe Ile Phe Gly Arg Asp Glu Phe
            420                 425                 430

Pro Gly Gln Ala Val Ala Ser Val Ile Asp Glu Asn Ile Lys Leu Cys
        435                 440                 445

Arg Arg Leu Met Val Phe Val Ala Pro Glu Ser Ser Phe Gly Phe
450                 455                 460
```

```
Leu Lys Asn Leu Ser Glu Glu Gln Ile Ala Val Tyr Asn Ala Leu Ile
465                 470                 475                 480

Gln His Gly Met Lys Val Ile Leu Ile Glu Leu Glu Lys Val Lys Asp
                485                 490                 495

Tyr Ser Thr Met Pro Glu Ser Ile Gln Tyr Ile Arg Gln Lys His Gly
                500                 505                 510

Ala Ile Gln Trp Asp Gly Asp Phe Thr Glu Gln Ser Gln Cys Ala Lys
            515                 520                 525

Thr Lys Phe Trp Lys Lys Val Arg Tyr His Met Pro Pro Arg Arg Tyr
        530                 535                 540

Pro Ala Ser Ser Pro Val Gln Leu Leu Gly His Ile Pro Cys Asn Cys
545                 550                 555                 560

Lys Ala Gly Lys Cys Asn Ala Ala Thr Gly Leu Ile Thr Pro
                565                 570
```

<210> SEQ ID NO 5
<211> LENGTH: 2044
<212> TYPE: DNA
<213> ORGANISM: Rattus norvegicus

<400> SEQUENCE: 5

```
ccggctggcc taggatcagg caagaaaagg ctgaacgcct ttctaaggac ggactctttc      60
tgtacagctc cacttgggga agcccgaaat ggggatgcca cccttgctct ctgtgttggt     120
gtctttcgtg cttccacttt ttgtggcagc aggtaactgt actgatgtct atatgcacca     180
tgagatgatt tcagagggcc agcctttccc cttcaactgc acatacctc cagtaacaaa     240
cggggcagtg aatctgacat ggcatagaac acccagtaag agcccaatct ccatcaacag     300
acacgttaga attcaccagg accagtcctg gattttgttt cttccgttgg cattggagga     360
ctcaggcatc tatcaatgtg ttataaagga tgcccacagc tgttaccgaa tagctataaa     420
cctaaccgtt tttagaaaac actggtgcga ctcttccaac gaagagagtt ccataaattc     480
ctcagatgag taccagcaat ggttacccat aggaaaatcg gcagtctga cgtgccatct     540
ctacttccca gagagctgtg ttttggattc aataaagtgg tataagggtt gtgaagagat     600
taaagtgagc aagaagtttt gccctacagg aacaaagctt cttgttaaca acatcgacgt     660
ggaggatagt gggagctatg catgctcagc cagactgaca cacttgggga gaatcttcac     720
ggttagaaac tacattgctg tgaataccaa ggaagttggg tctggaggaa ggatccctaa     780
catcacgtat ccaaaaaaca actccattga agttcaactt ggctccaccc tcattgtgga     840
ctgcaatata acagacacga aggagaatac gaacctcaga tgctggcgag ttaacaacac     900
cctggtggac gattactaca cgacttcaa acgcatccag gaaggaatcg aaaccaatct     960
gtctctgagg aatcacattc tgtacacagt gaacataaca ttcttagaag tgaaaatgga    1020
ggactacggc catcctttca catgccacgc tgcggtgtcc gcagcctaca tcattctgaa    1080
acgcccagct ccagacttcc gggcttacct cataggaggt ctcatggctt cctacttct    1140
ggccgtgtcc attctgtaca tctacaacac ctttaaggtc gacatcgtgc tttggtatag    1200
gagtaccttc cacactgccc aggctccaga tgacgagaag ctgtatgatg cctatgtctt    1260
ataccccaag tacccaagag aaagccaggg ccatgatgtg acacactgg tgttgaagat    1320
cttgcccgag gtgctggaga acagtgtgg atataagtta ttcatatttg gcagggatga    1380
attccctgga caagctgtgg ccagcgtcat tgatgaaaac attaagctgt gtaggaggct    1440
gatggtcctc gtggcaccag agacatccag cttcagcttt ctgaagaact tgactgaaga    1500
```

```
acaaatcgct gtctacaatg ccctcgtcca ggacggcatg aaggtcattc tgattgaact    1560
ggagagagtc aaggactaca gcaccatgcc cgagtccatt cagtacatcc gacagaagca    1620
cggggccatc cagtgggatg gggacttcac agagcaggca cagtgcgcca agacgaaatt    1680
ctggaagaaa gtgagatatc atatgccacc caggaggtac ccggcatctc ccccgtcca    1740 gctgctagga cacacacccc gcataccagg ctagtgcagt gccaccgcca cggggctcat    1800
aactccttaa gagcggttag tgtgtggtgg ctcgcactac aacctctctg gatcatctac    1860
ccccgtagct tgctcttttg tgcttgtgag cgacctcgtc cttagccacg tcatatttg    1920 attttttgtt tgttttgttt gtttgttgta tgcttttagt catagctgat tcgtactact    1980
cctgtttgct tcatggttcc tgaatcccag agactccctg agcatgggtg gctatcatgt    2040
tggg                                                                 2044
```

<210> SEQ ID NO 6
<211> LENGTH: 561
<212> TYPE: PRT
<213> ORGANISM: Rattus norvegicus

<400> SEQUENCE: 6

```
Met Gly Met Pro Pro Leu Leu Phe Cys Trp Val Ser Phe Val Leu Pro
1               5                   10                  15

Leu Phe Val Ala Ala Gly Asn Cys Thr Asp Val Tyr Met His His Glu
                20                  25                  30

Met Ile Ser Glu Gly Gln Pro Phe Pro Phe Asn Cys Thr Tyr Pro Pro
            35                  40                  45

Val Thr Asn Gly Ala Val Asn Leu Thr Trp His Arg Thr Pro Ser Lys
        50                  55                  60

Ser Pro Ile Ser Ile Asn Arg His Val Arg Ile His Gln Asp Gln Ser
65                  70                  75                  80

Trp Ile Leu Phe Leu Pro Leu Ala Leu Glu Asp Ser Gly Ile Tyr Gln
                85                  90                  95

Cys Val Ile Lys Asp Ala His Ser Cys Tyr Arg Ile Ala Ile Asn Leu
            100                 105                 110

Thr Val Phe Arg Lys His Trp Cys Asp Ser Ser Asn Glu Glu Ser Ser
        115                 120                 125

Ile Asn Ser Ser Asp Glu Tyr Gln Gln Trp Leu Pro Ile Gly Lys Ser
130                 135                 140

Gly Ser Leu Thr Cys His Leu Tyr Phe Pro Glu Ser Cys Val Leu Asp
145                 150                 155                 160

Ser Ile Lys Trp Tyr Lys Gly Cys Glu Glu Ile Lys Val Ser Lys Lys
                165                 170                 175

Phe Cys Pro Thr Gly Thr Lys Leu Leu Val Asn Asn Ile Asp Val Glu
            180                 185                 190

Asp Ser Gly Ser Tyr Ala Cys Ser Ala Arg Leu Thr His Leu Gly Arg
        195                 200                 205

Ile Phe Thr Val Arg Asn Tyr Ile Ala Val Asn Thr Lys Glu Val Gly
    210                 215                 220

Ser Gly Gly Arg Ile Pro Asn Ile Thr Tyr Pro Lys Asn Asn Ser Ile
225                 230                 235                 240

Glu Val Gln Leu Gly Ser Thr Leu Ile Val Asp Cys Asn Ile Thr Asp
                245                 250                 255

Thr Lys Glu Asn Thr Asn Leu Arg Cys Trp Arg Val Asn Asn Thr Leu
            260                 265                 270
```

-continued

Val Asp Asp Tyr Tyr Asn Asp Phe Lys Arg Ile Gln Glu Gly Ile Glu
        275                 280                 285

Thr Asn Leu Ser Leu Arg Asn His Ile Leu Tyr Thr Val Asn Ile Thr
    290                 295                 300

Phe Leu Glu Val Lys Met Glu Asp Tyr Gly His Pro Phe Thr Cys His
305                 310                 315                 320

Ala Ala Val Ser Ala Ala Tyr Ile Ile Leu Lys Arg Pro Ala Pro Asp
                325                 330                 335

Phe Arg Ala Tyr Leu Ile Gly Gly Leu Met Ala Phe Leu Leu Leu Ala
                340                 345                 350

Val Ser Ile Leu Tyr Ile Tyr Asn Thr Phe Lys Val Asp Ile Val Leu
        355                 360                 365

Trp Tyr Arg Ser Thr Phe His Thr Ala Gln Ala Pro Asp Asp Glu Lys
    370                 375                 380

Leu Tyr Asp Ala Tyr Val Leu Tyr Pro Lys Tyr Pro Arg Glu Ser Gln
385                 390                 395                 400

Gly His Asp Val Asp Thr Leu Val Leu Lys Ile Leu Pro Glu Val Leu
                405                 410                 415

Glu Lys Gln Cys Gly Tyr Lys Leu Phe Ile Phe Gly Arg Asp Glu Phe
                420                 425                 430

Pro Gly Gln Ala Val Ala Ser Val Ile Asp Glu Asn Ile Lys Leu Cys
            435                 440                 445

Arg Arg Leu Met Val Leu Val Ala Pro Glu Thr Ser Ser Phe Ser Phe
    450                 455                 460

Leu Lys Asn Leu Thr Glu Glu Gln Ile Ala Val Tyr Asn Ala Leu Val
465                 470                 475                 480

Gln Asp Gly Met Lys Val Ile Leu Ile Glu Leu Glu Arg Val Lys Asp
                485                 490                 495

Tyr Ser Thr Met Pro Glu Ser Ile Gln Tyr Ile Arg Gln Lys His Gly
                500                 505                 510

Ala Ile Gln Trp Asp Gly Asp Phe Thr Glu Gln Ala Gln Cys Ala Lys
            515                 520                 525

Thr Lys Phe Trp Lys Lys Val Arg Tyr His Met Pro Pro Arg Arg Tyr
    530                 535                 540

Pro Ala Ser Pro Pro Val Gln Leu Leu Gly His Thr Pro Arg Ile Pro
545                 550                 555                 560

Gly

<210> SEQ ID NO 7
<211> LENGTH: 573
<212> TYPE: PRT
<213> ORGANISM: Artificial Sequence
<220> FEATURE:
<223> OTHER INFORMATION: Humanized Il1r12

<400> SEQUENCE: 7

Met Gly Val Thr Ser Leu Leu Phe Cys Gly Val Phe Leu Leu Leu
1               5                   10                  15

Leu Phe Val Ala Ala Asp Gly Cys Lys Asp Ile Phe Met Lys Asn Glu
                20                  25                  30

Ile Leu Ser Ala Ser Gln Pro Phe Ala Phe Asn Cys Thr Phe Pro Pro
            35                  40                  45

Ile Thr Ser Gly Glu Val Ser Val Thr Trp Tyr Lys Asn Ser Ser Lys
        50                  55                  60

-continued

```
Ile Pro Val Ser Lys Ile Ile Gln Ser Arg Ile His Gln Asp Glu Thr
 65                  70                  75                  80

Trp Ile Leu Phe Leu Pro Met Glu Trp Gly Asp Ser Gly Val Tyr Gln
                 85                  90                  95

Cys Val Ile Lys Gly Arg Asp Ser Cys His Arg Ile His Val Asn Leu
            100                 105                 110

Thr Val Phe Glu Lys His Trp Cys Asp Thr Ser Ile Gly Gly Leu Pro
        115                 120                 125

Asn Leu Ser Asp Glu Tyr Lys Gln Ile Leu His Leu Gly Lys Asp Asp
    130                 135                 140

Ser Leu Thr Cys His Leu His Phe Pro Lys Ser Cys Val Leu Gly Pro
145                 150                 155                 160

Ile Lys Trp Tyr Lys Asp Cys Asn Glu Ile Lys Gly Glu Arg Phe Thr
                165                 170                 175

Val Leu Glu Thr Arg Leu Leu Val Ser Asn Val Ser Ala Glu Asp Arg
            180                 185                 190

Gly Asn Tyr Ala Cys Gln Ala Ile Leu Thr His Ser Gly Lys Gln Tyr
        195                 200                 205

Glu Val Leu Asn Gly Ile Thr Val Ser Ile Thr Glu Arg Ala Gly Tyr
    210                 215                 220

Gly Gly Ser Val Pro Lys Ile Ile Tyr Pro Lys Asn His Ser Ile Glu
225                 230                 235                 240

Val Gln Leu Gly Thr Thr Leu Ile Val Asp Cys Asn Val Thr Asp Thr
                245                 250                 255

Lys Asp Asn Thr Asn Leu Arg Cys Trp Arg Val Asn Asn Thr Leu Val
            260                 265                 270

Asp Asp Tyr Tyr Asp Glu Ser Lys Arg Ile Arg Glu Gly Val Glu Thr
        275                 280                 285

His Val Ser Phe Arg Glu His Asn Leu Tyr Thr Val Asn Ile Thr Phe
    290                 295                 300

Leu Glu Val Lys Met Glu Asp Tyr Gly Leu Pro Phe Met Cys His Ala
305                 310                 315                 320

Gly Val Ser Thr Ala Tyr Ile Ile Leu Gln Leu Pro Val Pro Asp Phe
                325                 330                 335

Arg Ala Tyr Leu Leu Gly Gly Leu Met Ala Phe Leu Leu Leu Val Val
            340                 345                 350

Ser Val Leu Phe Ile Tyr Asn Ser Phe Lys Ile Asp Ile Met Leu Trp
        355                 360                 365

Tyr Arg Ser Ala Phe His Thr Ala Gln Ala Pro Asp Asp Glu Lys Leu
    370                 375                 380

Tyr Asp Ala Tyr Val Leu Tyr Pro Lys Tyr Pro Arg Gly Ser Gln Gly
385                 390                 395                 400

His Asp Val Asp Thr Leu Val Leu Lys Ile Leu Pro Glu Val Leu Glu
                405                 410                 415

Lys Gln Cys Gly Tyr Lys Leu Phe Ile Phe Gly Arg Asp Glu Phe Pro
            420                 425                 430

Gly Gln Ala Val Ala Ser Val Ile Asp Glu Asn Ile Lys Leu Cys Arg
        435                 440                 445

Arg Leu Met Val Phe Val Ala Pro Glu Ser Ser Phe Gly Phe Leu
    450                 455                 460

Lys Asn Leu Ser Glu Glu Gln Ile Ala Val Tyr Asn Ala Leu Ile Gln
465                 470                 475                 480

His Gly Met Lys Val Ile Leu Ile Glu Leu Glu Lys Val Lys Asp Tyr
```

| | 485 | | 490 | | 495 | |
|---|---|---|---|---|---|---|
Ser Thr Met Pro Glu Ser Ile Gln Tyr Ile Arg Gln Lys His Gly Ala
          500                 505                 510

Ile Gln Trp Asp Gly Asp Phe Thr Glu Gln Ser Gln Cys Ala Lys Thr
          515                 520                 525

Lys Phe Trp Lys Val Arg Tyr His Met Pro Pro Arg Arg Tyr Pro
    530                 535                 540

Ala Ser Ser Pro Val Gln Leu Leu Gly His Ile Pro Cys Asn Cys Lys
545                 550                 555                 560

Ala Gly Lys Cys Asn Ala Ala Thr Gly Leu Ile Thr Pro
                565                 570

<210> SEQ ID NO 8
<211> LENGTH: 888
<212> TYPE: DNA
<213> ORGANISM: Homo sapiens

<400> SEQUENCE: 8

```
aaaacccaag tgcagtagaa gccattgttc ataatggtag ggatacaggg tccttcgtaa      60
cagattatca gtgtggccta tgctggaaag tctggtgacc tctgattttt tttgcttcca     120
ggtctttggc cttggcactc tttgtcatat tagagttcct gggtctaggc ctgggcagga     180
ttcataggtg cagctgcttc tgctggaggt agactgcatc caacaaagta agggtgctgg     240
gtgagttctg ggagtataga ttctgactgg ggtcactgct gggctggccg ccagtctttc     300
atctgaccca gggttaaact gtggcttggg actgactcag gtcctctctt ggggtcggtc     360
tgcacataaa aggactccta tccttggcag ttctgaaaca acaccaccac aatggaaaaa     420
gcattgaaaa ttgacacacc tcagcagggg agcattcagg atatcaatca tcgggtgtgg     480
gttcttcagg accagacgct catagcagtc ccgaggaagg accgtatgtc tccagtcact     540
attgccttaa tctcatgccg acatgtggag acccttgaga agacagagg gaacccatc     600
tacctgggcc tgaatggact caatctctgc ctgatgtgtg ctaaagtcgg ggaccagccc     660
acactgcagc tgaaggaaaa ggatataatg gatttgtaca accaacccga gcctgtgaag     720
tccttctct tctaccacag ccagagtggc aggaactcca ccttcgagtc tgtggctttc     780
cctggctggt tcatcgctgt cagctctgaa ggaggctgtc ctctcatcct tacccaagaa     840
ctggggaaag ccaacactac tgactttggg ttaactatgc tgttttaa                 888
```

<210> SEQ ID NO 9
<211> LENGTH: 158
<212> TYPE: PRT
<213> ORGANISM: Homo sapiens

<400> SEQUENCE: 9

Met Glu Lys Ala Leu Lys Ile Asp Thr Pro Gln Gln Gly Ser Ile Gln
1               5                   10                  15

Asp Ile Asn His Arg Val Trp Val Leu Gln Asp Gln Thr Leu Ile Ala
                20                  25                  30

Val Pro Arg Lys Asp Arg Met Ser Pro Val Thr Ile Ala Leu Ile Ser
            35                  40                  45

Cys Arg His Val Glu Thr Leu Glu Lys Asp Arg Gly Asn Pro Ile Tyr
        50                  55                  60

Leu Gly Leu Asn Gly Leu Asn Leu Cys Leu Met Cys Ala Lys Val Gly
65                  70                  75                  80

Asp Gln Pro Thr Leu Gln Leu Lys Glu Lys Asp Ile Met Asp Leu Tyr 85                  90                  95
Asn Gln Pro Glu Pro Val Lys Ser Phe Leu Phe Tyr His Ser Gln Ser
                100                 105                 110

Gly Arg Asn Ser Thr Phe Glu Ser Val Ala Phe Pro Gly Trp Phe Ile
            115                 120                 125

Ala Val Ser Ser Glu Gly Gly Cys Pro Leu Ile Leu Thr Gln Glu Leu
        130                 135                 140

Gly Lys Ala Asn Thr Thr Asp Phe Gly Leu Thr Met Leu Phe
145                 150                 155

<210> SEQ ID NO 10
<211> LENGTH: 883
<212> TYPE: DNA
<213> ORGANISM: Mus musculus

<400> SEQUENCE: 10
taacctcctc ttttcgtgtt gtggataaaa ggcttggacc ttagtagagc ttgtcagaga    60
agctgagcac agtagtgggt gtagttctgt agtgtgcaga cacattccta ttcaatcagg   120
gtcaatctgc agattggcag ctcagaaaca acatcaccat aatgaataag gagaaagaac   180
taagagcagc atcaccttcg cttagacatg ttcaggatct tagtagtcgt gtgtggatcc   240
tgcagaacaa tatcctcact gcagtcccaa ggaaagagca aacagttcca gtcactatta   300
ccttgctccc atgccaatat ctggacactc ttgagacgaa caggggggat cccacgtaca   360
tgggagtgca aaggccgatg agctgcctgt tctgcacaaa ggatggggag cagcctgtgc   420
tacagcttgg ggaagggaac ataatggaaa tgtacaacaa aaaggaacct gtaaaagcct   480
ctctcttcta tcacaagaag agtggtacaa cctctacatt tgagtctgca gccttccctg   540
gttggttcat cgctgtctgc tctaaaggga gctgccccact cattctgacc caagaactgg   600
ggaaatctt catcactgac ttcgagatga ttgtggtaca ttaaggtttt tagacacatt   660
gctctgtggc actctctcaa gatttcttgg attctaacaa gaagcaatca agacaccccc   720
taacaaaatg gaagactgaa agaaagctga gccctccct gggctgtttt tccttggtgg   780
tgaatcagat gcagaacatc ttaccatgtt ttcatccaaa gcatttactg ttggttttta   840
caaggagtga attttttaaa ataaaatcat ttatctcatt tgc                    883

<210> SEQ ID NO 11
<211> LENGTH: 160
<212> TYPE: PRT
<213> ORGANISM: Mus musculus

<400> SEQUENCE: 11

Met Asn Lys Glu Lys Glu Leu Arg Ala Ala Ser Pro Ser Leu Arg His
1               5                   10                  15

Val Gln Asp Leu Ser Ser Arg Val Trp Ile Leu Gln Asn Asn Ile Leu
            20                  25                  30

Thr Ala Val Pro Arg Lys Glu Gln Thr Val Pro Val Thr Ile Thr Leu
        35                  40                  45

Leu Pro Cys Gln Tyr Leu Asp Thr Leu Glu Thr Asn Arg Gly Asp Pro
    50                  55                  60

Thr Tyr Met Gly Val Gln Arg Pro Met Ser Cys Leu Phe Cys Thr Lys
65                  70                  75                  80

Asp Gly Glu Gln Pro Val Leu Gln Leu Gly Glu Gly Asn Ile Met Glu
                85                  90                  95

Met Tyr Asn Lys Lys Glu Pro Val Lys Ala Ser Leu Phe Tyr His Lys

```
            100                 105                 110
Lys Ser Gly Thr Thr Ser Thr Phe Glu Ser Ala Ala Phe Pro Gly Trp
            115                 120                 125

Phe Ile Ala Val Cys Ser Lys Gly Ser Cys Pro Leu Ile Leu Thr Gln
            130                 135                 140

Glu Leu Gly Glu Ile Phe Ile Thr Asp Phe Glu Met Ile Val Val His
145                 150                 155                 160
```

<210> SEQ ID NO 12
<211> LENGTH: 869
<212> TYPE: DNA
<213> ORGANISM: Rattus norvegicus

<400> SEQUENCE: 12

```
taatctcctc ccttcatgtt ttggataaaa ggcctggacc ctagcagagc ttgtcagaga      60
agctgagcac agtagtggct gtagttctgt agtgtgcaga tacattcctc tgcaatcagg     120
atcagtctgc agattggcag ttcagaaaca acatcaccat aatgaataag gataaagaac     180
taagtgcagc aacaccttgg tttagacata ttcaggatct tagtagtcgt gtgtgggtcc     240
ttcaagacaa tattcttact gcagtcccaa ggaaagagca aacggttcca gtcactatca     300
ccttactccc atgccaatat ctggacactc ttgagaagaa caagggggat cccatgtacc     360
tgggagtgaa gaaccctcaa agttgtctgt cctgcacaaa gaatggggag cagcctgtac     420
tacaacttcg ggaagggaac atactggata tgtaccacca gaaggaacgt gtaaaagcct     480
ctctcttcta tcacaagaag agtggtacaa cctctacatt cgagtctgca gccttccctg     540
gttggttcat tgctgtctgc tccaaaggga gctgcccact cgttttgacc caagaacttg     600
ggaaaacctt catcactgat tttgagatga ctgtagtaca ttaagattgc tctgcagcac     660
tctctgaaga tctctcggat tctaacaagc aaccaaacac acccccaaca aaatacaaga     720
ctgaaaagaa agctgagccc tccctgggct ttttttccctt ggcaggtgga tcagatgcag     780
aacttcttac catgttttca tccaaagcat ttactgatgg tttttacaag aagaaaacgt     840
ttttaattaa aatcatttat ctcacttgc                                       869
```

<210> SEQ ID NO 13
<211> LENGTH: 160
<212> TYPE: PRT
<213> ORGANISM: Rattus norvegicus

<400> SEQUENCE: 13

```
Met Asn Lys Asp Lys Glu Leu Ser Ala Ala Thr Pro Trp Phe Arg His
1               5                   10                  15

Ile Gln Asp Leu Ser Ser Arg Val Trp Val Leu Gln Asp Asn Ile Leu
            20                  25                  30

Thr Ala Val Pro Arg Lys Glu Gln Thr Val Pro Val Thr Ile Thr Leu
            35                  40                  45

Leu Pro Cys Gln Tyr Leu Asp Thr Leu Glu Lys Asn Lys Gly Asp Pro
        50                  55                  60

Met Tyr Leu Gly Val Lys Lys Pro Gln Ser Cys Leu Ser Cys Thr Lys
65                  70                  75                  80

Asn Gly Glu Gln Pro Val Leu Gln Leu Arg Glu Gly Asn Ile Leu Asp
                85                  90                  95

Met Tyr His Gln Lys Glu Arg Val Lys Ala Ser Leu Phe Tyr His Lys
            100                 105                 110

Lys Ser Gly Thr Thr Ser Thr Phe Glu Ser Ala Ala Phe Pro Gly Trp
```

```
                    115                 120                 125
Phe Ile Ala Val Cys Ser Lys Gly Ser Cys Pro Leu Val Leu Thr Gln
        130                 135                 140

Glu Leu Gly Lys Thr Phe Ile Thr Asp Phe Glu Met Thr Val Val His
145                 150                 155                 160

<210> SEQ ID NO 14
<211> LENGTH: 1186
<212> TYPE: DNA
<213> ORGANISM: Homo sapiens

<400> SEQUENCE: 14
cacgggttcc tccccactct gtctttctca cctctccttc acttttccta gcctcctcac     60
caccatctga tctatcttgt tctcttcaca aaaggctctg aagacatcat gaacccacaa    120
cgggaggcag cacccaaatc ctatgctatt cgtgattctc gacagatggt gtgggtcctg    180
agtggaaatt ctttaatagc agctcctctt agccgcagca ttaagcctgt cactcttcat    240
ttaatagcct gtagagacac agaattcagt gacaaggaaa agggtaatat ggtttacctg    300
ggaatcaagg gaaagatctc tgtctcttc tgtgcagaaa ttcagggcaa gcctactttg    360
cagcttaagc ttcagggctc ccaagataac atagggaagg acacttgctg aaactagtt    420 ggaattcaca catgcataaa cctggatgtg agagagagct gcttcatggg aaccccttgac    480 caatggggaa taggagtggg tagaaagaag tggaagagtt cctttcaaca tcaccatctc    540
aggaagaagg acaaagattt ctcatccatg cggaccaaca taggaatgcc aggaaggatg    600
tagaaataag gggaggaaga ttcccatctc tacaatcttt gagtgggttt gctatcaatg    660
aaatgctaca aatggaataa gttgcagaaa ttttttctctt ttcttgggtt ctggagagtt    720
tgtaaaacaa ggacactatg tattttttaaa gagttggtaa atcttacctg taaagctaga    780
gaaggtcgga gtcttttag gagtagattt ggactacata acctgtaaat gtgttttgtc    840
cagtccttag agtgtttttt aaaaaattgt aaagtcaagg ttttcatgaa aaatgggaag    900
atcagacaac attgctcctg aattcccaca gagcagcaag ctactagagc tcaatctgtt    960
atttcttttc ctgatgtaca gggggttaagt cctatggaag aaacagcaga attattcaaa   1020
attatttaca taatgtgcaa ttattcacta gagcatgagg agtgaaacgc tctgtttagt   1080
atgtataact taaaggaac acatacaatt aaaagtaatt gaaagacatt tcttcttaaa   1140
aattctataa tcttacactg gtaaaataaa ctagttttc ccatgt                   1186

<210> SEQ ID NO 15
<211> LENGTH: 164
<212> TYPE: PRT
<213> ORGANISM: Homo sapiens

<400> SEQUENCE: 15

Met Asn Pro Gln Arg Glu Ala Ala Pro Lys Ser Tyr Ala Ile Arg Asp
1               5                   10                  15

Ser Arg Gln Met Val Trp Val Leu Ser Gly Asn Ser Leu Ile Ala Ala
                20                  25                  30

Pro Leu Ser Arg Ser Ile Lys Pro Val Thr Leu His Leu Ile Ala Cys
            35                  40                  45

Arg Asp Thr Glu Phe Ser Asp Lys Glu Lys Gly Asn Met Val Tyr Leu
        50                  55                  60

Gly Ile Lys Gly Lys Asp Leu Cys Leu Phe Cys Ala Glu Ile Gln Gly
65                  70                  75                  80
```

```
Lys Pro Thr Leu Gln Leu Lys Leu Gln Gly Ser Gln Asp Asn Ile Gly
             85                  90                  95

Lys Asp Thr Cys Trp Lys Leu Val Gly Ile His Thr Cys Ile Asn Leu
            100                 105                 110

Asp Val Arg Glu Ser Cys Phe Met Gly Thr Leu Asp Gln Trp Gly Ile
        115                 120                 125

Gly Val Gly Arg Lys Lys Trp Lys Ser Ser Phe Gln His His His Leu
        130                 135                 140

Arg Lys Lys Asp Lys Asp Phe Ser Ser Met Arg Thr Asn Ile Gly Met
145                 150                 155                 160

Pro Gly Arg Met

<210> SEQ ID NO 16
<211> LENGTH: 790
<212> TYPE: DNA
<213> ORGANISM: Mus musculus

<400> SEQUENCE: 16
gactggcctc attgcctgct gtcataactt cgatcccaga gacaagactt ctttggacca      60
aggcaatgat ggcttccct ccacaatctt gtgtacatgt tcttcctcca aagagtattc      120
aaatgtggga accgaatcat aacactatgc atggatcctc acaatctccc agaaactaca     180
gggttcatga ctcacaacag atggtatggg tcctgactgg aaatacttta acagcagttc     240
ctgctagcaa caatgtcaag cctgtcattc ttagcttgat agcatgtaga gacacggaat     300
tccaagatgt aaagaaaggt aatctagttt tcctgggaat caagaacaga aatctctgct     360
tctgctgtgt tgagatggag ggcaaaccaa ctttgcagct taaggaagta gacatcatga     420
atttgtacaa agagagaaaa gcacaaaaag cctttctgtt ctatcatggc atagagggct     480
ccacttctgt ctttcagtca gtcctctatc ctggctggtt tatagccacc tcttccatag     540
aaagacagac aatcatcctc acacatcagc ggggtaaatt ggttaacact aacttctaca     600
tagagtctga gaagtaaatc caacatgggt catatgtggc cagctccagg ccacagaatc     660
aaactgttga agaatcttct acttgaaaac atagcaagcc tcttagaaga ccaccatgcc     720
atgtcttcac cagacatcca tgtctaaaat gccactcatt tgaatatcat tccagcatga     780
agcccatgaa                                                             790

<210> SEQ ID NO 17
<211> LENGTH: 183
<212> TYPE: PRT
<213> ORGANISM: Mus musculus

<400> SEQUENCE: 17

Met Met Ala Phe Pro Pro Gln Ser Cys Val His Val Leu Pro Pro Lys
1               5                  10                  15

Ser Ile Gln Met Trp Glu Pro Asn His Asn Thr Met His Gly Ser Ser
            20                  25                  30

Gln Ser Pro Arg Asn Tyr Arg Val His Asp Ser Gln Gln Met Val Trp
        35                  40                  45

Val Leu Thr Gly Asn Thr Leu Thr Ala Val Pro Ala Ser Asn Asn Val
    50                  55                  60

Lys Pro Val Ile Leu Ser Leu Ile Ala Cys Arg Asp Thr Glu Phe Gln
65                  70                  75                  80

Asp Val Lys Lys Gly Asn Leu Val Phe Leu Gly Ile Lys Asn Arg Asn
                85                  90                  95
```

```
Leu Cys Phe Cys Cys Val Glu Met Glu Gly Lys Pro Thr Leu Gln Leu
            100                 105                 110
Lys Glu Val Asp Ile Met Asn Leu Tyr Lys Glu Arg Lys Ala Gln Lys
            115                 120                 125
Ala Phe Leu Phe Tyr His Gly Ile Glu Gly Ser Thr Ser Val Phe Gln
        130                 135                 140
Ser Val Leu Tyr Pro Gly Trp Phe Ile Ala Thr Ser Ser Ile Glu Arg
145                 150                 155                 160
Gln Thr Ile Ile Leu Thr His Gln Arg Gly Lys Leu Val Asn Thr Asn
                165                 170                 175
Phe Tyr Ile Glu Ser Glu Lys
            180

<210> SEQ ID NO 18
<211> LENGTH: 587
<212> TYPE: DNA
<213> ORGANISM: Rattus norvegicus

<400> SEQUENCE: 18
ggcgtgggtc ctggctggaa attctttgac agcggttcct gctagcaaca gcgtcaaatc        60
tgtcattctt agcttgatag catgtagaga catggaattc caagatgaaa agaagggtaa       120
tctagttttc ctgggaatca aaggcagaag tctctgcctc ttctgtgctg agatcgaggg       180
caaaccgact ttgcagctta aggatgtaga catcatggat ttgtacaatg agaaaaaagc       240
acagaaagcc tttctcttct accatggcat agagggatct acttctgtct ttcagtcagt       300
cttgtatcct ggctggttta tagccacctc ttccacagca agacaaacaa tcattcttac       360
acaggagagg ggtgaagcta ataacactaa cttctactta gagtctgaga attagatcta       420
ccatgggcca tatgtggcca gttgcaggcc aaagaatcaa actgttggag aatcttttac       480
ttgaaaacat agcaagacat cttagaagac caccatgttt cctcttctcc tgacatccat       540
gtctgaaatg ccattcattg gtataagaga ataaaaaata gggctgg                    587

<210> SEQ ID NO 19
<211> LENGTH: 179
<212> TYPE: PRT
<213> ORGANISM: Rattus norvegicus

<400> SEQUENCE: 19

Met Met Ala Phe Pro Pro Gln Ser His Val Cys Phe Thr Pro Pro Lys
1               5                   10                  15
Ser Ser Asp Phe Asp Asn Ile Asn Lys Gly Val Gln Ala Phe Pro Ser
            20                  25                  30
Thr Tyr Arg Val His Asp Ser Gln His Lys Ala Trp Val Leu Ala Gly
        35                  40                  45
Asn Ser Leu Thr Ala Val Pro Ala Ser Asn Ser Val Lys Ser Val Ile
50                  55                  60
Leu Ser Leu Ile Ala Cys Arg Asp Met Glu Phe Gln Asp Glu Lys Lys
65                  70                  75                  80
Gly Asn Leu Val Phe Leu Gly Ile Lys Gly Arg Ser Leu Cys Leu Phe
                85                  90                  95
Cys Ala Glu Ile Glu Gly Lys Pro Thr Leu Gln Leu Lys Asp Val Asp
            100                 105                 110
Ile Met Asp Leu Tyr Asn Glu Lys Lys Ala Gln Lys Ala Phe Leu Phe
            115                 120                 125
Tyr His Gly Ile Glu Gly Ser Thr Ser Val Phe Gln Ser Val Leu Tyr
```

Pro Gly Trp Phe Ile Ala Thr Ser Ser Thr Ala Arg Gln Thr Ile Ile
145                 150                 155                 160

Leu Thr Gln Glu Arg Gly Glu Ala Asn Asn Thr Asn Phe Tyr Leu Glu
            165                 170                 175

Ser Glu Asn

<210> SEQ ID NO 20
<211> LENGTH: 1212
<212> TYPE: DNA
<213> ORGANISM: Homo sapiens

<400> SEQUENCE: 20

```
gaagctgctg gagccacgat tcagtcccct ggactgtaga taaagaccct ttcttgccag    60
gtgctgagac aaccacacta tgagaggcac tccaggagac gctgatggtg gaggaagggc   120
cgtctatcaa tcaatgtgta aacctattac tgggactatt aatgatttga atcagcaagt   180
gtggacccct cagggtcaga accttgtggc agttccacga agtgacagtg tgaccccagt   240
cactgttgct gttatcacat gcaagtatcc agaggctctt gagcaaggca gagggatcc    300
catttatttg ggaatccaga atccagaaat gtgtttgtat tgtgagaagg ttggagaaca   360
gcccacattg cagctaaaag agcagaagat catggatctg tatggccaac ccgagcccgt   420
gaaacccttc ctttctacc gtgccaagac tggtaggacc tccacccttg agtctgtggc   480
cttcccggac tggttcattg cctcctccaa gagagaccag cccatcattc tgacttcaga   540
acttgggaag tcatacaaca ctgcctttga attaaatata aatgactgaa ctcagcctag   600
aggtggcagc ttggtctttg tcttaaagtt tctggttccc aatgtgtttt cgtctacatt   660
ttcttagtgt cattttcacg ctggtgctga cagggggca aggctgctgt tatcatctca   720
ttttataatg aagaagaagc aattacttca tagcaactga agaacaggat gtggcctcag   780
aagcaggaga gctgggtggt ataaggctgt cctctcaagc tggtgctgtg taggccacaa   840
ggcatctgca tgagtgactt taagactcaa agaccaaaca ctgagctttc ttctaggggt   900
gggtatgaag atgcttcaga gctcatgcgc gttacccacg atggcatgac tagcacagag   960
ctgatctctg tttctgtttt gctttattcc ctcttgggat gatatcatcc agtctttata  1020
tgttgccaat atacctcatt gtgtgtaata gaaccttctt agcattaaga ccttgtaaac  1080
aaaaataatt cttgtgttaa gttaaatcat ttttgtccta attgtaatgt gtaatcttaa  1140
agttaaataa actttgtgta tttatataat aataaagcta aaactgatat aaaataaaga  1200
aagagtaaac tg                                                     1212
```

<210> SEQ ID NO 21
<211> LENGTH: 169
<212> TYPE: PRT
<213> ORGANISM: Homo sapiens

<400> SEQUENCE: 21

Met Arg Gly Thr Pro Gly Asp Ala Asp Gly Gly Arg Ala Val Tyr
1               5                   10                  15

Gln Ser Met Cys Lys Pro Ile Thr Gly Thr Ile Asn Asp Leu Asn Gln
                20                  25                  30

Gln Val Trp Thr Leu Gln Gly Gln Asn Leu Val Ala Val Pro Arg Ser
            35                  40                  45

Asp Ser Val Thr Pro Val Thr Val Ala Val Ile Thr Cys Lys Tyr Pro
        50                  55                  60

```
Glu Ala Leu Glu Gln Gly Arg Gly Asp Pro Ile Tyr Leu Gly Ile Gln
 65                  70                  75                  80

Asn Pro Glu Met Cys Leu Tyr Cys Glu Lys Val Gly Glu Gln Pro Thr
                 85                  90                  95

Leu Gln Leu Lys Glu Gln Lys Ile Met Asp Leu Tyr Gly Gln Pro Glu
            100                 105                 110

Pro Val Lys Pro Phe Leu Phe Tyr Arg Ala Lys Thr Gly Arg Thr Ser
        115                 120                 125

Thr Leu Glu Ser Val Ala Phe Pro Asp Trp Phe Ile Ala Ser Ser Lys
130                 135                 140

Arg Asp Gln Pro Ile Ile Leu Thr Ser Glu Leu Gly Lys Ser Tyr Asn
145                 150                 155                 160

Thr Ala Phe Glu Leu Asn Ile Asn Asp
                165

<210> SEQ ID NO 22
<211> LENGTH: 1647
<212> TYPE: DNA
<213> ORGANISM: Mus musculus

<400> SEQUENCE: 22
atcattacac ctgggagctg cccaagctgg gatttggtct tctagacttt ccataaggac      60
tctttcttgc catgtaccta caaacctaca aaaccctttg agtgcgcctc tgagtgtgga     120
gctttctgca gttcagggtt cagtgaatgg acagatctgt cttgctgtaa gtgatcctgt     180
gagcgatcct gtgagcgatc ctgtgagcga tcctgtgagc gatcctgtga gcgatcctgt     240
gagtgatcct gtgagcaatc ctgtgagagc tctgtgcacc agaacaagat cacgatggaa     300
aacaatgaaa aaaaaaacat tgtgtatgga agtgatgttg agatgaaaca cgagagagct     360
gggctatttg tatcttcagc tatgttttct aaacacccat tttctacaca catctcagga     420
agagaaactc ctgactttgg ggaggttttt gacttggacc agcaggtgtg gatctttcgt     480
aatcaggccc ttgtgacagt tccacgaagc cacagagtaa ccccagtcag cgtgactatc     540
ctcccatgca gtacccccaga gtctcttgaa caggacaaag ggattgccat ttatttggga     600
attcagaatc cagataaatg cctgttttgt aaggaagtta atggacaccc tactttgctg     660
ctaaaggaag agaagatttt ggatttgtac caccaccctg agccaatgaa gccattcctg     720
ttttaccaca cccggacagg tggaacatcc acctttgaat cagtggcttt ccctggccac     780
tatattgcct cctccaagac tggcaacccc atcttcctca catcaaaaaa gggagaatat     840
tacaacatta acttcaattt agatataaag tcttaaactc agcatggaag tggagggttg     900
gttagaactc ttcctcttaa acatcaaac ctctaatatg ttatcatttg tttgatctat     960
ggtattttca tactgaaagg taagcaggac caacattatc tcctttcata gatgaagaag    1020
caacaaaata atgcatactc caaagtcggt gggattggag tggtgtaagg atgttctcta    1080
agactgaagt ggtccaatct ataagacatc atgtctgaga ataggggtgc tgtgccacag    1140
tgtataaaac ctagaatgcc ctgtgtgtga gtggtgacat cctcatttcc agccattggc    1200
ctgattcata ccatgttttc acacatttgt aatatcaact ccttgcattt ggatagcaga    1260
ggcctcacaa tgacatttgc ctcaacagct aatagctttg atctttcaat gctgtgtaga    1320
tctgaataca ctagaaaagg aattagaatc ctgagtgaat gaactgtgag gagccgccct    1380
cacatttgcc attataagat ggcactgaca gctgtgttct aagtggtaaa catagtctgc    1440
acacatgcag gggcagtttt cccaccatgt gttctgcctt tcccgtgatg acaactgggc    1500
```

```
cgatgggctg cagccaatca gggagtaata cgtcctaggt ggaggataat tctccttaaa      1560
agggacgggg ttctggcact ctctcccttc cttgcttgct ctcttgcact ctggctcctg      1620
aagatgtaag caataaagct ttgccgc                                          1647

<210> SEQ ID NO 23
<211> LENGTH: 164
<212> TYPE: PRT
<213> ORGANISM: Mus musculus

<400> SEQUENCE: 23

Met Phe Ser Lys His Pro Phe Ser Thr His Ile Ser Gly Arg Glu Thr
1               5                   10                  15

Pro Asp Phe Gly Glu Val Phe Asp Leu Asp Gln Gln Val Trp Ile Phe
            20                  25                  30

Arg Asn Gln Ala Leu Val Thr Val Pro Arg Ser His Arg Val Thr Pro
        35                  40                  45

Val Ser Val Thr Ile Leu Pro Cys Lys Tyr Pro Glu Ser Leu Glu Gln
    50                  55                  60

Asp Lys Gly Ile Ala Ile Tyr Leu Gly Ile Gln Asn Pro Asp Lys Cys
65                  70                  75                  80

Leu Phe Cys Lys Glu Val Asn Gly His Pro Thr Leu Leu Lys Glu
                85                  90                  95

Glu Lys Ile Leu Asp Leu Tyr His His Pro Glu Pro Met Lys Pro Phe
                100                 105                 110

Leu Phe Tyr His Thr Arg Thr Gly Gly Thr Ser Thr Phe Glu Ser Val
            115                 120                 125

Ala Phe Pro Gly His Tyr Ile Ala Ser Ser Lys Thr Gly Asn Pro Ile
        130                 135                 140

Phe Leu Thr Ser Lys Lys Gly Glu Tyr Tyr Asn Ile Asn Phe Asn Leu
145                 150                 155                 160

Asp Ile Lys Ser

<210> SEQ ID NO 24
<211> LENGTH: 1395
<212> TYPE: DNA
<213> ORGANISM: Rattus norvegicus

<400> SEQUENCE: 24
ggaagctgcc caagctggga tttgatcttc tgaactttcc ataaggactc tttcttgcca       60
ggcaccagaa caagctcatg atggaaaaca atgaaaaaaa tcgttacata tgggtgtgat      120
gttgagatgt gacactaacg aactgggcta tttgtatctt cagctatgtc ctctaaatac      180
ccacattctc catgtactgc ctcagcagga aagaaactc ctgaccttgg caggttttct       240
gatgtggatc agcaggtgtg gatctttcgt gatcaggccc ttgtgacagt tccacgaagc      300
cacactgtaa ctccagtcac tgtgactgtc ctcccatgca gtacccaga gtctcttgag       360 cagggcaaag ggactcccat ttatttggga attcaaaatc cagataaatg cctgttttgt      420
aaggaagtta atggacaccc cactttgctc ctgaaggaag agaagatttt gaatttgtac      480
caccatcctg agccaatgaa gccattcctg ttttaccaca ccctgacagg tgcaacgtcc      540
acctttgaat cagtggtttt ccctggcagc tttattgcct cctccaagat tggcaaaccc      600
atcttcctca catcaaaaaa gggagaacat tacaacattc acttcagttt agatataatt      660
tagatataaa gtcttgaact cagaatggag gtggagggtt ggttagaact cttataactt      720
```

```
caaacctcta atatgctatc atttgtttga tgtgtggttg tttcatactg agaagtgagc    780
aaaaccaaca ttatctcatt tcatagatga agaagcaaca aaacagaatg tgtactccaa    840
agtaggttgg atgggagtgg tgtaaggctc tcctctaaga ctgaagtggt ccaacccata    900
aggcatcatg cctttctcag gtgctattat agggtgctgt gccacagtat ataaaaacta    960
gaatgcccca tgtgtgagta gcaacatcct cacttccagt cattggcctg attcatacca   1020
ggttttcaca cacttgtaat accaattcct tgcatttgga tagcaggagc ctcacaatga   1080
catttgctgc caacagctga tagctttgat ccttcagcaa ctgactgcta cgtggatctg   1140
aagacgccag aaaaggaatt agaatcctaa gtgaacgaac agttttaaa atgtctagaa    1200 ctatttaaac tatgttagaa tacagtggtt tatccttgaa aggtaaggat actgcctggt   1260
aaatcaaaaa cagttaggtc aataaactca gcttgaacaa ttctttcctg gaaacaatgt   1320
gtacaagtaa tgattaaaac attacctttt attattctag acttccataa aaaaaaaaaa   1380
aaaaaaaaaa aaaaa                                                    1395

<210> SEQ ID NO 25
<211> LENGTH: 165
<212> TYPE: PRT
<213> ORGANISM: Rattus norvegicus

<400> SEQUENCE: 25

Met Ser Ser Lys Tyr Pro His Ser Pro Cys Thr Ala Ser Ala Gly Lys
1               5                   10                  15

Glu Thr Pro Asp Leu Gly Gln Val Ser Asp Val Asp Gln Gln Val Trp
            20                  25                  30

Ile Phe Arg Asp Gln Ala Leu Val Thr Val Pro Arg Ser His Thr Val
        35                  40                  45

Thr Pro Val Thr Val Thr Val Leu Pro Cys Lys Tyr Pro Glu Ser Leu
    50                  55                  60

Glu Gln Gly Lys Gly Thr Pro Ile Tyr Leu Gly Ile Gln Asn Pro Asp
65                  70                  75                  80

Lys Cys Leu Phe Cys Lys Glu Val Asn Gly His Pro Thr Leu Leu Leu
                85                  90                  95

Lys Glu Glu Lys Ile Leu Asn Leu Tyr His His Pro Glu Pro Met Lys
            100                 105                 110

Pro Phe Leu Phe Tyr His Thr Leu Thr Gly Ala Thr Ser Thr Phe Glu
        115                 120                 125

Ser Val Val Phe Pro Gly Ser Phe Ile Ala Ser Ser Lys Ile Gly Lys
    130                 135                 140

Pro Ile Phe Leu Thr Ser Lys Lys Gly Glu His Tyr Asn Ile His Phe
145                 150                 155                 160

Ser Leu Asp Ile Ile
                165

<210> SEQ ID NO 26
<211> LENGTH: 108
<212> TYPE: DNA
<213> ORGANISM: Artificial Sequence
<220> FEATURE:
<223> OTHER INFORMATION: Synthetic Oligonucleotide

<400> SEQUENCE: 26
tacatttgaa ggtcttagca ttatgcttct aaatgactgg gctagtttgg gcgatcgcga     60
caagaagggt tgatttactc tgtaggtgag tacagagtaa agaactct                 108
```

<210> SEQ ID NO 27
<211> LENGTH: 140
<212> TYPE: DNA
<213> ORGANISM: Artificial Sequence
<220> FEATURE:
<223> OTHER INFORMATION: Synthetic Oligonucleotide

<400> SEQUENCE: 27

```
caccctgagc acatggggaa tccttcttgg gttgcaacat gtggaaggac ctcgagataa      60
cttcgtataa tgtatgctat acgaagttat atgcatggcc tccgcgccgg gttttggcgc     120
ctcccgcggg cgccccctc                                                  140
```

<210> SEQ ID NO 28
<211> LENGTH: 181
<212> TYPE: DNA
<213> ORGANISM: Artificial Sequence
<220> FEATURE:
<223> OTHER INFORMATION: Synthetic Oligonucleotide

<400> SEQUENCE: 28

```
tttcactgca ttctagttgt ggtttgtcca aactcatcaa tgtatcttat catgtctgga      60
ataacttcgt ataatgtatg ctatacgaag ttatgctagt aactataacg gtcctaaggt     120
agcgagctag ccagaatcaa tgacaaagat gaagaatata tttaacctca taaacttggt     180
t                                                                     181
```

<210> SEQ ID NO 29
<211> LENGTH: 177
<212> TYPE: DNA
<213> ORGANISM: Artificial Sequence
<220> FEATURE:
<223> OTHER INFORMATION: Synthetic Oligonucleotide

<400> SEQUENCE: 29

```
caccctgagc acatggggaa tccttcttgg gttgcaacat gtggaaggac ctcgagataa      60
cttcgtataa tgtatgctat acgaagttat gctagtaact ataacggtcc taaggtagcg     120
agctagccag aatcaatgac aaagatgaag aatatattta acctcataaa cttggtt       177
```

<210> SEQ ID NO 30
<211> LENGTH: 100
<212> TYPE: DNA
<213> ORGANISM: Artificial Sequence
<220> FEATURE:
<223> OTHER INFORMATION: Synthetic Oligonucleotide

<400> SEQUENCE: 30

```
ctggctctgt caactagatt ggaaggcatg cggagctgcc agtctcaact cgtcgacgtc      60
actctccttt cccactgcat gtgaagcatt tgagtgtctg                           100
```

<210> SEQ ID NO 31
<211> LENGTH: 140
<212> TYPE: DNA
<213> ORGANISM: Artificial Sequence
<220> FEATURE:
<223> OTHER INFORMATION: Synthetic Oligonucleotide

<400> SEQUENCE: 31

```
tgcactcaga aaagacaagt attcacattt tttcttgtgg ctgatctgga ctcgagataa      60
cttcgtataa tgtatgctat acgaagttat atgcatggcc tccgcgccgg gttttggcgc     120
ctcccgcggg cgccccctc                                                  140
```

<210> SEQ ID NO 32
<211> LENGTH: 181
<212> TYPE: DNA
<213> ORGANISM: Artificial Sequence
<220> FEATURE:
<223> OTHER INFORMATION: Synthetic Oligonucleotide

<400> SEQUENCE: 32

```
tttcactgca ttctagttgt ggtttgtcca aactcatcaa tgtatcttat catgtctgga      60
ataacttcgt ataatgtatg ctatacgaag ttatgctagt aactataacg gtcctaaggt     120
agcgagctag cctatgcctg cacagcccct ccataggtac taaggattta aactctcgtt     180
t                                                                    181
```

<210> SEQ ID NO 33
<211> LENGTH: 177
<212> TYPE: DNA
<213> ORGANISM: Artificial Sequence
<220> FEATURE:
<223> OTHER INFORMATION: Synthetic Oligonucleotide

<400> SEQUENCE: 33

```
tgcactcaga aaagacaagt attcacattt tttcttgtgg ctgatctgga gtcgagataa      60
cttcgtataa tgtatgctat acgaagttat gctagtaact ataacggtcc taaggtagcg     120
agctagccta tgcctgcaca gcccttccat aggtactaag gatttaaact ctcgttt        177
```

<210> SEQ ID NO 34
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 34

```
gggtccatta tttgagactt tcca                                             24
```

<210> SEQ ID NO 35
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 35

```
agctttctgc tggccccatt acttg                                            25
```

<210> SEQ ID NO 36
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 36

```
gcatgtgcct gtcttcaca                                                   19
```

<210> SEQ ID NO 37
<211> LENGTH: 25
<212> TYPE: DNA
<213> ORGANISM: Artificial Sequence
<220> FEATURE:
<223> OTHER INFORMATION: Synthetic Oligonucleotide

```
<400> SEQUENCE: 37
gagtggtaca acctctacat ttgag                                          25

<210> SEQ ID NO 38
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 38
ctgcagcctt ccctggttgg ttc                                            23

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
agtgggcagc tccctttaga                                                20

<210> SEQ ID NO 40
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 40
cccactgcat gtgaagcat                                                 19

<210> SEQ ID NO 41
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 41
ttgagtgtct gcacctgagc ca                                             22

<210> SEQ ID NO 42
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 42
ggagacctct tattagcctg tga                                            23

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
cacctgccct aagtcatctc                                                20

<210> SEQ ID NO 44
<211> LENGTH: 22
```

```
<212> TYPE: DNA
<213> ORGANISM: Artificial Sequence
<220> FEATURE:
<223> OTHER INFORMATION: Synthetic Oligonucleotide

<400> SEQUENCE: 44
tacagcaaga gcagaggcca ca                                           22

<210> SEQ ID NO 45
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 45
gcctgcagag aagcaatgtt c                                            21

<210> SEQ ID NO 46
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 46
cagccgctac acaccacaa                                               19

<210> SEQ ID NO 47
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 47
ccagctgcta cacaaatgca gggc                                         24

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
cgtcatctcc tgccagttca                                              20

<210> SEQ ID NO 49
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 49
ctgctgctca gagcattgaa a                                            21

<210> SEQ ID NO 50
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 50
```
ccatggccag ggaaggctta cta                                               23

<210> SEQ ID NO 51
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 51
cgcctccgac tgaacatatg ac                                                22

<210> SEQ ID NO 52
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 52
cctgatatgc atctttccct atgga                                             25

<210> SEQ ID NO 53
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 53
atggcacctc agaccagacc cac                                               23

<210> SEQ ID NO 54
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 54
ggcagcaata atactgggac aaac                                              24

<210> SEQ ID NO 55
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 55
ggccaggaaa cacatctgaa g                                                 21

<210> SEQ ID NO 56
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 56
agcagtgact ctaaatgctc agtgtga                                           27

<210> SEQ ID NO 57
<211> LENGTH: 23
<212> TYPE: DNA
<213> ORGANISM: Artificial Sequence

```
<220> FEATURE:
<223> OTHER INFORMATION: Synthetic Oligonucleotide

<400> SEQUENCE: 57
gcctcactcc aacaacatta tga                                              23
```

MOUSE MODEL OF DITRA DISEASE AND USES THEREOF

CROSS REFERENCE TO RELATED APPLICATIONS

This application claims the benefit of priority from U.S. Provisional Application No. 62/698,459, filed Jul. 16, 2018, and U.S. Provisional Application No. 62/867,477, filed Jun. 27, 2019, the entire contents of both of which are incorporated herein by reference.

FIELD OF THE DISCLOSURE

This disclosure relates to genetically modified rodent animals and rodent models of human diseases. More specifically, this disclosure relates to genetically modified rodents whose genome comprises a humanized Il1rl2 gene (coding for the IL1rl2 subunit of an IL-36R) and human IL-36α, β and γ ligand genes. The genetically modified rodents disclosed herein display enhanced skin and intestinal inflammation in preclinical model of psoriasis and Inflammatory Bowel Disease (IBD), respectively, and may serve as a rodent model of human deficiency of the Interleukin-36R antagonist (DITRA) disease.

INCORPORATION BY REFERENCE OF SEQUENCE LISTING

The sequence listing in the ASCII text file, named as 35950_10404US01_SequenceListing.txt of 65 KB, created on Jul. 9, 2019, and submitted to the United States Patent and Trademark Office via EFS-Web, is incorporated herein by reference in its entirety.

BACKGROUND ART

The Interleukin (IL)-36 subfamily consists of three agonists (IL-36α, β and γ, previously designated as IL1F6, IL1F8 and IL1F9, respectively) and one antagonist (IL36Ra) that signal through a heterodimeric receptor (IL-36R) leading to activation of nuclear factor-κB (NFκB) and mitogen-activated protein kinases (MAPKs). Similar to the classical IL-1 family members, IL-36 cytokines are involved in the initiation and regulation of immune responses. Members of the IL-36 family were first demonstrated to be predominantly expressed in squamous epithelial tissues, and, in particular, in psoriatic skin lesions. The link between IL-36R and epithelial-mediated diseases was confirmed in humans based on loss of function mutations in IL-36Ra leading to the diagnosis of Generalized Pustular Psoriasis (abbreviated "GPP"), now understood to be a species of GPP called deficiency of the Interleukin-36R antagonist (abbreviated "DITRA"). Elevated IL-36 expression was reported in GPP, palmoplantar pustular psoriasis (PPPP), inflammatory bowel disease (IBD), rheumatoid and psoriatic arthritis, asthma, chronic obstructive pulmonary disease, chronic kidney disease, and ichthyosis.

SUMMARY OF THE DISCLOSURE

Disclosed herein are some embodiments of rodents genetically modified to comprise a humanized Il1rl2 gene encoding an Il1rl2 protein having an ectodomain substantially identical with a human IL1RL2 ectodomain, as well as human Il1f6, Il1f8 and Il1f9 genes encoding human IL1F6, IL1F8, and IL1F9, respectively. Il1rl2 is a subunit of the heterodimer IL-36R protein, which binds to three agonists: IL1F6, IL1F8 and IL1F9 (also known as IL-36α, β and γ, respectively). The rodents disclosed herein, while comprising a humanized Il1rl2 gene and expressing three human agonist ligand genes, maintain the endogenous IL-36Ra antagonist, where the endogenous IL-36Ra is about 20-fold less potent in inhibiting human IL-36R signaling. Such quadruple humanized rodents (e.g., humanized Il1rl2 and human IL1F6, IL1F8 and IL1F9) have been shown herein to display symptoms of DITRA patients where the mutation in IL-36Ra leads to an enhanced IL-36R signaling. Accordingly, genetically modified rodents, compositions and methods for making such rodents, and methods of using such rodents as a model for screening and developing therapeutic agents are provided therein.

In one aspect of some embodiments, disclosed herein is a genetically modified rodent whose genome comprises (1) a humanized Il1rl2 gene at an endogenous rodent Il1rl2 locus, wherein the humanized Il1rl2 gene encodes a humanized Il1rl2 protein that comprises an ectodomain substantially identical with the ectodomain of a human IL1RL2 protein; (2) a human IL1F6 gene at an endogenous rodent Il1f6 locus; (3) a human IL1F8 gene at an endogenous rodent Il1f8 locus; and (4) a human IL1F9 gene at an endogenous rodent Il1f9 locus.

In some embodiments, the humanized Il1rl2 gene in a rodent encodes a humanized Il1rl2 protein that comprises a transmembrane-cytoplasmic sequence substantially identical with the transmembrane-cytoplasmic sequence of the endogenous rodent Il1rl2 protein. In some embodiments, the humanized Il1rl2 gene in a rodent encodes a humanized Il1rl2 protein that comprises a signal peptide substantially identical with the signal peptide of the endogenous rodent Il1rl2 protein.

In some embodiments, the humanized Il1rl2 gene in a rodent encodes a humanized Il1rl2 protein comprising an ectodomain substantially identical with the ectodomain of a human IL1RL2 protein wherein the human IL1RL2 protein comprises the amino acid sequence as set forth in SEQ ID NO: 2.

In some embodiments, the humanized Il1rl2 gene in a rodent encodes a humanized Il1rl2 protein comprising an ectodomain wherein the ectodomain comprises amino acids 22-337 of SEQ ID NO: 7.

In some embodiments, the humanized Il1rl2 gene in a rodent encodes a humanized Il1rl2 protein that comprises the amino acid sequence as set forth in SEQ ID NO: 7.

In some embodiments, the humanized Il1rl2 gene in a rodent is operably linked to the endogenous rodent Il1rl2 promoter at the endogenous rodent Il1rl2 locus.

In some embodiments, the humanized Il1rl2 gene in a rodent results from a replacement of a genomic fragment of the endogenous rodent Il1rl2 gene at the endogenous rodent Il1rl2 locus with a nucleotide sequence of a human IL1RL2 gene.

In some embodiments, the nucleotide sequence of a human IL1RL2 gene is a genomic fragment of the human IL1RL2 gene that encodes substantially the ectodomain of the human IL1RL2 protein. In some embodiments, the genomic fragment of the human IL1RL2 gene comprises exons 3-8 of the human IL1RL2 gene.

In some embodiments, the genomic sequence of an endogenous rodent Il1rl2 gene remaining after a humanization replacement comprises the exons downstream of exon 8 of the endogenous rodent Il1rl2 gene. In some embodiments, the genomic sequence of the endogenous rodent Il1rl2 gene remaining after a humanization replacement comprises exons 1-2 of the endogenous rodent Il1rl2 gene.

In specific embodiments, the humanized Il1rl2 gene in a rodent disclosed herein comprises exons 1-2 of the endogenous rodent Il1rl2 gene, exons 3-8 of the human IL1RL2 gene, and the remaining exons downstream of exon 8 of the endogenous rodent Il1rl2 gene.

In some embodiments, the human IL1F6 gene in a rodent disclosed herein replaces the endogenous rodent Il1f6 gene at the endogenous rodent Il1f6 locus.

In some embodiments, the human IL1F8 gene in a rodent disclosed herein replaces the endogenous rodent Il1f8 gene at the endogenous rodent Il1f8 locus.

In some embodiments, the human IL1F9 gene in a rodent disclosed herein replaces the endogenous rodent Il1f9 gene at the endogenous rodent Il1f9 locus.

In some embodiments, a rodent disclosed herein is homozygous for one or more of the four humanized and/or human genes. In some embodiments, rodent disclosed herein is homozygous for each of the four humanized and/or human genes.

In some embodiments, a rodent disclosed herein displays shortened colon as compared to a wild type rodent. In some embodiments, a rodent disclosed herein displays enhanced inflammation in an experimentally induced inflammation model as compared to a wild type rodent. In some embodiments, the experimentally induced inflammation model is a skin inflammation model induced by imiquimod (IMQ). In some embodiments, the experimentally induced inflammation model is an intestinal inflammation model induced by dextran sulfate sodium (DSS) or oxazolone.

In some embodiments, a rodent disclosed herein is a mouse or a rat.

Further disclosed herein is an isolated cell or tissue from a rodent described herein.

In a further aspect of some embodiments, disclosed herein is a method of making a genetically modified rodent, the method comprising modifying a rodent genome to comprise (1) a humanized Il1rl2 gene at an endogenous rodent Il1rl2 locus, wherein the humanized Il1rl2 gene encodes a humanized Il1rl2 protein that comprises an ectodomain substantially identical with the ectodomain of a human IL1RL2 protein; (2) a human IL1F6 gene at an endogenous rodent Il1f6 locus; (3) a human IL1F8 gene at an endogenous rodent Il1f8 locus; and (4) a human IL1F9 gene at an endogenous rodent Il1f9 locus; and making a rodent comprising the modified genome.

In some embodiments, the rodent genome is modified by a process comprising (i) making a first rodent comprising a humanized Il1rl2 gene at the endogenous rodent Il1rl2 locus; (ii) making a second rodent comprising a human IL1F6 gene at an endogenous rodent Il1f6 locus, a human IL1F8 gene at the endogenous rodent Il1f8 locus, and a human IL1F9 gene at the endogenous rodent Il1f9 locus; and (iii) crossing the first rodent with the second rodent to obtain a modified rodent genome.

In some embodiments, the rodent comprising a humanized Il1rl2 gene at the endogenous rodent Il1rl2 locus is made by providing a rodent embryonic stem (ES) cell, inserting a nucleotide sequence of a human IL1RL2 gene into the rodent Il1rl2 locus of the rodent ES cell to form a humanized Il1rl2 gene at the rodent Il1rl2 locus, thereby obtaining a rodent ES cell comprising the humanized Il1rl2 gene, and making a rodent using the rodent ES cell comprising the humanized Il1rl2 gene.

In some embodiments, the nucleotide sequence of a human IL1RL2 gene being inserted replaces a genomic fragment of the rodent Il1rl2 gene at the rodent Il1rl2 locus. In some embodiments, the nucleotide sequence of a human IL1RL2 gene is a genomic fragment of the human IL1RL2 gene that encodes substantially the ectodomain of the human IL1RL2 protein. In some embodiments, the genomic fragment of the human IL1RL2 gene comprises exons 3-8 of the human IL1RL2 gene. In some embodiments, the genomic sequence of the endogenous rodent Il1rl2 gene remaining after the replacement comprises the exons downstream of exon 8 of the endogenous rodent Il1rl2 gene. In some embodiments, the genomic sequence of the endogenous rodent Il1rl2 gene remaining after a humanization replacement comprises exons 1-2 of the endogenous rodent Il1rl2 gene. In some embodiments, the humanized Il1rl2 gene formed as a result of a humanization replacement comprises exons 1-2 of the endogenous rodent Il1rl2 gene, exons 3-8 of the human IL1RL2 gene, and the remaining exons downstream of exon 8 of the endogenous rodent Il1rl2 gene.

In some embodiments, a rodent comprising a human IL1F6 gene, a human IL1F8 gene, and a human IL1F9 gene is made by: providing a rodent embryonic stem (ES) cell; inserting a human IL1F6 gene into the rodent Il1f6 locus of the rodent ES cell, a human IL1F8 gene into the rodent Il1f8 locus of the rodent ES cell, and a human IL1F9 gene into the rodent Il1f9 locus of the rodent ES cell, thereby obtaining a rodent ES cell comprising the human IL1F6 gene, the human IL1F8 gene, and the human IL1F9 gene; and making a rodent using the rodent ES cell comprising the human IL1F6 gene, the human IL1F8 gene, and the human IL1F9 gene.

In some embodiments, a human IL1F6 gene, a human IL1F8 gene, and a human IL1F9 gene, are provided in a contiguous nucleic acid molecule.

In some embodiments of the methods, the human IL1F6 gene replaces the endogenous rodent Il1f6 gene at the endogenous rodent Il1f6 locus.

In some embodiments of the methods, the human IL1F8 gene replaces the endogenous rodent Il1f8 gene at the endogenous rodent Il1f8 locus.

In some embodiments of the methods, the human IL1F9 gene replaces the endogenous rodent Il1f9 gene at the endogenous rodent Il1f9 locus.

In another aspect of some embodiments, disclosed herein is a rodent embryonic stem (ES) cell comprising (1) a humanized Il1rl2 gene at an endogenous rodent Il1rl2 locus, wherein the humanized Il1rl2 gene encodes a humanized Il1rl2 protein that comprises an ectodomain substantially identical with the ectodomain of a human IL1RL2 protein; (2) a human IL1F6 gene at an endogenous rodent Il1f6 locus; (3) a human IL1F8 gene at an endogenous rodent Il1f8 locus; and (4) a human IL1F9 gene at an endogenous rodent Il1f9 locus. In some embodiments, such ES cell can be made by methods disclosed herein. In some embodiments, use of such ES cell to make a rodent is also disclosed.

In still another aspect of some embodiments, disclosed herein are targeting nucleic acid constructs useful for modifying a rodent genome (e.g., in a rodent ES cell) for making a modified rodent.

In some embodiments, disclosed herein is a targeting nucleic acid construct comprising a nucleotide sequence of a human IL1RL2 gene, flanked by 5' and 3' rodent nucleotide sequences capable of mediating homologous recombination and integration of the nucleotide sequence of the human IL1RL2 gene into a rodent Il1rl2 locus to form a humanized Il1rl2 gene, wherein the humanized Il1rl2 gene encodes a humanized Il1rl2 protein that comprises an ectodomain substantially identical with the ectodomain of a human IL1RL2 protein.

In some embodiments, disclosed herein is a targeting nucleic acid construct, comprising a contiguous nucleic acid sequence which comprises: a human IL1F6 gene, a human IL1F8 gene, and a human IL1F9 gene, wherein the contiguous nucleic acid sequence is flanked by 5' and 3' rodent nucleotide sequences capable of mediating homologous recombination and integration of the contiguous nucleic acid sequence into the rodent locus encompassing the rodent Il1f6 gene, the rodent Il1f8 gene, and the rodent Il1f9 gene.

In a further aspect of some embodiments, disclosed herein is use of a rodent disclosed herein as a rodent model of human diseases associated with deregulated IL-36 signaling. As non-limiting examples of the embodiments disclosed herein, the rodent can be used to study the pathology and molecular basis of human diseases associated with deregulated IL-36 signaling (such as, but not limited to, DITRA), or to screen, test and develop therapeutic compounds useful for treating such diseases.

In still a further aspect of some embodiments, disclosed herein is a method of assessing the therapeutic efficacy of a candidate compound for treating a disease associated with deregulated IL-36 signaling, comprising administering an agent to a rodent disclosed herein to induce inflammation, administering a candidate compound to the rodent, and determining whether the candidate compound inhibits and/or decreases induced inflammation.

In some embodiments, the agent administered to induce inflammation is DSS or oxazolone, which induces intestinal inflammation in the rodent. In some embodiments, the agent administered to induce inflammation is IMQ which induces skin inflammation in the rodent.

In some embodiments, a candidate compound is administered to the rodent before, during, or after the administration of an agent that induces inflammation. In some embodiments, a candidate compound can be a small molecule compound, a nucleic acid inhibitor, or an antigen-binding protein such as an antibody. In some embodiments, a candidate compound is an antibody that specifically binds human IL-36R.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 1A-1D show embodiments of an exemplary strategy for humanization of mouse Il1rl2. FIG. 1A shows a diagram, not to scale, of the genomic organization of mouse Il1rl2 and human IL1RL2 genes. Exons are represented by thin bars placed across the genomic sequences. A mouse genomic fragment of about 25,324 base pairs (bp) to be deleted and a human genomic fragment of about 32,389 bp to be inserted are indicated. Locations of probes used in an assay described in Example 1 are indicated. FIG. 1B illustrates, not to scale, an exemplary modified BAC vector for humanization of an endogenous mouse Il1rl2 gene, along with the junction sequences at the bottom (SEQ ID NOS: 26-28), to achieve (i) replacement of mouse Il1rl2 exons 3-8 and intervening introns, along with the 3' 155 bp of mouse intron 2 and the 5' 642 bp of mouse intron 8 with human IL1RL2 exons 3-8 and intervening introns, as well as the 3' 346 bp of human intron 2 and 5' 1101 bp of human intron 8, and (ii) an insertion of a loxP-hUb1-em7-Neo-pA-mPrm1-Crei-loxP cassette (4996 bp) downstream of the insertion of the human genomic fragment in intron 8. FIG. 1C illustrates, not to scale, a humanized Il1rl2 allele after the neomycin cassette has been deleted, along with the junction sequences at the bottom (SEQ ID NOS: 26 and 29). FIG. 1D sets forth a sequence alignment of a mouse Il1rl2 protein (SEQ ID NO: 4), a human IL1 RL2 protein (SEQ ID NO: 2), and a humanized Il1rl2 protein (SEQ ID NO: 7).

FIGS. 2A-2D show embodiments of an exemplary strategy for replacing mouse Il1f8, Il1f9, and Il1f6 with human IL1F8, IL1F9, and IL1F6. FIG. 2A shows a diagram, not to scale, of the genomic organization of mouse Il1f8, Il1f9, and Il1f6 genes and human IL1F8, IL1F9, AND IL1F6 genes. Exons are represented by thin bars placed across the genomic sequences. A mouse genomic fragment of about 76,548 bp to be deleted and a human genomic fragment of about 88,868 bp to be inserted are indicated. Locations of probes used in an assay described in Example 1 are indicated. FIG. 2B illustrates, not to scale, an exemplary modified BAC vector for replacement of endogenous mouse Il1f8, Il1f9, and Il1f6 genes, along with the junction sequences (SEQ ID NOS: 30-32) at the bottom, to achieve (i) replacement of coding sequences and untranslated regions (UTR), as well as intergenic sequence of mouse Il1f8, Il1f9, and Il1f6 with the corresponding human sequence of IL1F8, IL1F9, and IL1F6; and (ii) an insertion of a loxP-hUb1-em7-Hygro-pA-mPrm1-Crei-loxP cassette (5,218 bp) downstream of the insertion of the human genomic fragment. FIG. 2C illustrates, not to scale, a humanized locus after the hygromycin cassette has been deleted, along with the junction sequences at the bottom (SEQ ID NOS: 30 and 33). FIG. 2D sets forth sequence alignments of mouse Il1f6 (SEQ ID NO: 11) and human IL1F6 (SEQ ID NO: 9) proteins; of mouse Il1f8 (SEQ ID NO: 17) and human IL1F8 (SEQ ID NO: 15) proteins; and mouse Il1f9 (SEQ ID NO: 23) and human IL1F9 (SEQ ID NO: 21) proteins.

DETAILED DESCRIPTION

Figure 1A:
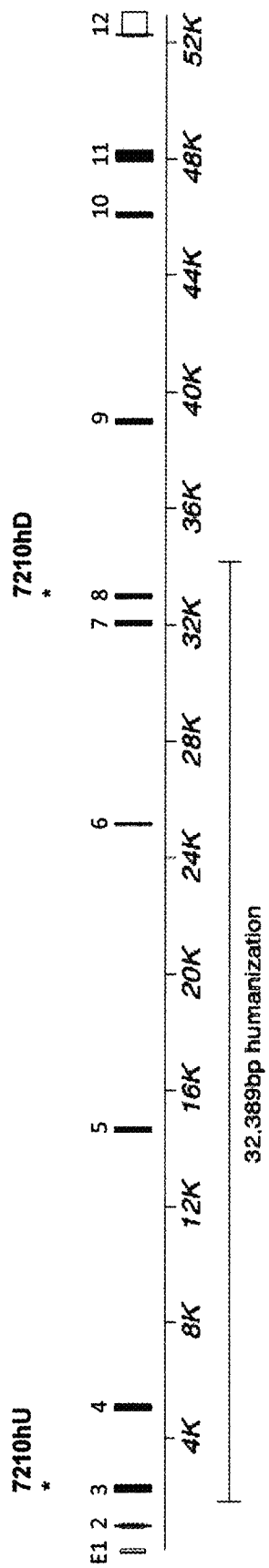
Figure 1A:
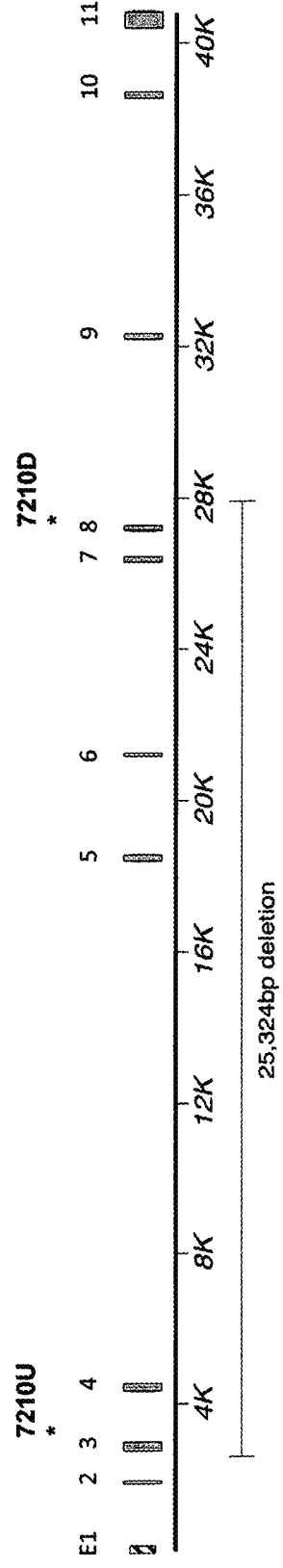

Disclosed herein are rodents (such as, but not limited to, mice) genetically modified to comprise a humanized Il1rl2 gene (encoding a humanized IL1RL2 protein having an ectodomain substantially identical with a human IL1RL2 ectodomain) and human genes coding for human IL-36α, β, γ ligands, while keeping the IL-36Ra antagonist endogenous which is 20-fold less potent in inhibiting human IL-36R signaling. Genetically modified rodents disclosed herein have been shown to display symptoms of DITRA patients where the mutation in IL-36Ra leads to an enhanced IL-36R signaling. Therefore, the genetically modified rodents disclosed herein can serve as a novel functional model of DITRA suitable for testing candidate therapeutic agents for treating DITRA and related disorders. The various embodiments are further described below.

Genetically Modified Rodents: Quadruple Humanization

In one aspect of some embodiments, this disclosure provides rodent animals that comprise in their genome a humanized Il1rl2 gene encoding a humanized IL1RL2 protein (a subunit of the IL-36R), and human genes encoding human IL-36α, β, and γ ligands. Such rodents are also referred to herein as quadruple humanized rodents (i.e., 4H or DITRA-like).

The term "humanized", when used in the context of nucleic acids or proteins, includes nucleic acids or proteins of a rodent whose structures (i.e., nucleotide or amino acid sequences) have been modified, in whole or in part, to include structures found in corresponding human nucleic acids or proteins. A rodent containing a humanized gene or expressing a humanized protein is a "humanized" rodent.

In some embodiments, rodents of this disclosure include, as non-limiting examples, a mouse, a rat, and a hamster. In some embodiments, rodents of this disclosure include, as non-limiting examples, a mouse and a rat. In some embodiments, a rodent is selected from the superfamily Muroidea. In some embodiments, a rodent of this disclosure is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some embodiments, a rodent of this disclosure is selected from a true mouse or rat (family Muridae), a gerbil, a spiny mouse, and a crested rat. In some embodiments, a mouse of this disclosure is from a member of the family Muridae.

IL-1RL2 Humanization

IL-36R is a member of the interleukin 1 receptor family and is a heterodimer that consists of a receptor subunit named IL1RL2 (also known as IL-1Rrp2) and a co-receptor subunit Interleukin-1 receptor accessory protein, IL-1RAcP (Garlanda C et al., Immunity 39, 1003-1018 (2013); Towne J E et al., J. Biol. Chem. 279, 13677-13688 (2004), which are incorporated by reference in their entireties). The receptor (IL-36R) can recognize and bind three different agonists, IL-36α, IL-36β, and IL-36γ (also known as IL1F6, IL1F8, and IL1F9), to induce the expression of inflammatory cytokines, as well as an antagonist, IL-36Ra, which binds to IL-36R and decreases the expression of inflammatory cytokines.

IL1RL2 contains a signal peptide, an extracellular domain ("ECD" or "ectodomain"), a transmembrane domain and an intracellular or cytoplasmic domain. See FIG. 1D, for example. Exemplary IL1RL2 sequences, including human, mouse, rat, and humanized Il1rl2 nucleic acid and protein sequences, are disclosed in the Sequence Listing and are summarized in the following table.

TABLE 1

| SEQ ID NO | Description | Features |
|---|---|---|
| 1 | *Homo sapiens* IL1RL2 transcript variant 1 mRNA, NM_003854.3 | Length: 2628 bp<br>CDS: 127-1854<br>12 Exons: 1-114, 115-184, 185-419, 420-615, 616-775, 776-850, 851-980, 981-1117, 1118-1261, 1262-1423, 1424-1804, 1805-2615. |
| 2 | *Homo sapiens* IL1RL2 protein, NP_003845.2 | Length: 575 aa<br>Signal peptide: 1-19<br>Mature: 20-575<br>Ectodomain: 20-335 |
| 3 | *Mus musculus* Il1rl2 mRNA, NM_133193.4 | Length: 4072 bp<br>CDS: 238-1962<br>11 Exons: 1-231, 232-301, 302-536, 537-735, 736-898, 899-970, 971-1100, 1101-1237, 1238-1381, 1382-1543, 1544-4072. |
| 4 | *Mus musculus* Il1rl2 Protein NP_573456.1 | Length: 574 aa<br>Signal peptide: 1-21<br>Mature: 22-574<br>Ectodomain: 22-338 |
| 5 | *Rattus norvegicus* Il1rl2 mRNA, NM_133575.1 | Length: 2044 bp<br>CDS: 89-1774 |
| 6 | *Rattus norvegicus* Il1rl2 Protein NP_598259.1 | Length: 561 aa<br>Signal peptide: 1-21<br>Mature: 22-561<br>Ectodomain: 22-338 |
| 7 | Humanized Il1rl2 Protein | Length: 573 aa<br>Signal peptide: 1-21<br>Mature: 22-573<br>Ectodomain: 22-337 |

In some embodiments, a rodent disclosed herein comprises a humanized Il1rl2 gene in its genome that includes a nucleotide sequence of an endogenous rodent Il1rl2 gene and a nucleotide sequence of a human IL1RL2 gene. As used herein, "a nucleotide sequence of a gene" includes a genomic sequence, an mRNA or cDNA sequence, in full or in part of the gene. As a non-limiting example, a nucleotide sequence of a human IL1RL2 gene includes a genomic sequence, an mRNA or cDNA sequence, in full or in part of the human IL1RL2 gene. The nucleotide sequence of the endogenous rodent Il1rl2 gene and the nucleotide sequence of the human IL1RL2 gene are operably linked to each other such that the humanized Il1rl2 gene in the rodent genome encodes an Il1rl2 protein, i.e., a protein that has an Il1rl2 protein structure (composed of an ectodomain, a transmembrane domain and a cytoplasmic domain), and that performs Il1rl2 functions (e.g., forms a heterodimer with Interleukin-1 receptor accessory protein (IL-1RacP) and recognizes the three ligands: IL-36α, IL-36β, and IL-36γ).

In some embodiments, a genetically modified rodent contains a humanized Il1rl2 gene in its genome, wherein the humanized Il1rl2 gene encodes a humanized Il1rl2 protein that contains an ectodomain that is substantially identical with the ectodomain of a human IL1RL2 protein. In some embodiments, an ectodomain that is substantially identical with the ectodomain of a human IL1RL2 protein exhibits the same functionality (e.g., ligand binding properties) as the ectodomain of a human IL1RL2 protein. By an ectodomain or polypeptide that is "substantially identical with the ectodomain of a human IL1RL2 protein", it is meant in some embodiments, a polypeptide that is at least 95%, 98%, 99% or 100% identical in sequence with the ectodomain of a human IL1RL2 protein; in some embodiments, a polypeptide that differs from the ectodomain of a human IL1RL2 protein by not more than 10, 9, 8, 7, 6, 5, 4, 3, 2 or 1 amino acid(s); and in some embodiments, a polypeptide that differs from the ectodomain of a human IL1RL2 protein only at the N- or C-terminal portion of the ectodomain, e.g., by having addition, deletion or substitution of amino acids, but not more than 5, 4, 3, 2 or 1 amino acid at the N- or C-terminal portion of the ectodomain. By "the N- or C-terminal portion of the ectodomain" is meant within 5-10 amino acids from the N- or C-terminus of the ectodomain. In some embodiments, a human IL1RL2 protein has an amino acid sequence substantially identical (e.g., at least 95%, 98%, 99% or 100% identical) with the amino acid sequence as set forth in SEQ ID NO: 2. In specific embodiments, a human IL1RL2 protein comprises the amino acid sequence as set forth in SEQ ID NO: 2, and its ectodomain is composed of amino acids 20-335 of SEQ ID NO: 2. In some embodiments, the humanized Il1rl2 gene encodes a humanized Il1rl2 protein that contains an ectodomain that is substantially identical with the ectodomain of the human IL1RL2 protein as set forth in SEQ ID NO: 2, i.e., with amino acids 20-335 of SEQ ID NO: 2. In some embodiments, the humanized Il1rl2 gene encodes a humanized Il1rl2 protein that contains an ectodomain comprising amino acids 22-337 of SEQ ID NO: 7.

In some embodiments, the humanized Il1rl2 gene encodes a humanized Il1rl2 protein that contains a transmembrane-cytoplasmic sequence (i.e., a sequence that includes both the transmembrane domain and the cytoplasmic domain) that is substantially identical with the transmembrane-cytoplasmic sequence of an endogenous rodent Il1rl2 protein. In some embodiments, a transmembrane-cytoplasmic sequence that is substantially identical with the transmembrane-cytoplasmic sequence of an endogenous rodent Il1rl2 protein exhibits the same functionality (e.g., signal transduction and/or interaction with intracellular molecules) as the transmembrane-cytoplasmic sequence of an endogenous rodent Il1rl2 protein. By a transmembrane-cytoplasmic sequence or polypeptide that is "substantially identical with the transmembrane-cytoplasmic sequence of an endogenous rodent Il1rl2 protein", it is meant in some embodiments, a polypeptide that is at least 95%, 98%, 99% or 100% identical in sequence with the transmembrane-cytoplasmic sequence of an endogenous rodent Il1rl2 protein; in some embodiments, a polypeptide that differs from the transmembrane-cytoplasmic sequence of an endogenous rodent Il1rl2 protein by not more than 10, 9, 8, 7, 6, 5, 4, 3, 2 or 1 amino acid(s); in some embodiments, a polypeptide that differs from the transmembrane-cytoplasmic sequence of an endogenous rodent Il1rl2 protein only at the N- or C-terminus, e.g., by having addition, deletion or substitution of amino acids, but not more than 5, 4, 3, 2 or 1 amino acid, at the N- or C-terminal portion of the transmembrane—cytoplasmic sequence. By "the N- or C-terminal portion of the transmembrane-cytoplasmic sequence" is meant within 5-10 amino acids from the N-terminus of the transmembrane domain or within 5-10 amino acids from the C-terminus of the cytoplasmic domain. In some embodiments, a humanized Il1rl2 protein contains a transmembrane-cytoplasmic sequence that is substantially identical with the transmembrane-cytoplasmic sequence of a mouse Il1rl2 protein, e.g., a mouse Il1rl2 protein substantially identical (at least 95%, 98%, 99%; or 100% identical) with SEQ ID NO: 4, or with the transmembrane-cytoplasmic sequence of a rat Il1rl2 protein, e.g., a rat Il1rl2 protein substantially identical (at least 95%, 98%, 99% or 100% identical) with SEQ ID NO: 6.

In some embodiments, the humanized Il1rl2 gene encodes a humanized Il1rl2 protein that contains a signal peptide that is substantially identical with the signal peptide of an endogenous rodent Il1rl2 protein. By a signal peptide that is "substantially identical with the signal peptide of an endogenous rodent Il1rl2 protein", it is meant in some embodiments, a polypeptide that is at least 95%, 98%, 99%; or 100% identical in sequence with the signal peptide of an endogenous rodent Il1rl2 protein; in some embodiments, a polypeptide that differs from the signal peptide of an endogenous rodent Il1rl2 protein by not more than 3, 2 or 1 amino acid(s); in some embodiments, a polypeptide that differs from the signal peptide of an endogenous rodent Il1rl2 protein only at the N- or C-terminus, e.g., by having addition, deletion or substitution of amino acids, but not more than 3, 2 or 1 amino acid, at the N- or C-terminal portion of the signal peptide. By "the N- or C-terminal portion of the signal peptide" is meant within 5 amino acids from the N- or C-terminus of the signal peptide. In some embodiments, a humanized Il1rl2 protein includes a signal peptide substantially identical with the signal peptide of a mouse Il1rl2 protein, e.g., a mouse Il1rl2 protein substantially identical (at least 95%, 98%, 99% or 100% identical) with SEQ ID NO: 4, or with the signal peptide of a rat Il1rl2 protein, e.g., a rat Il1rl2 protein substantially identical (at least 95%, 98%, 99% or 100% identical) with SEQ ID NO: 6.

In some embodiments, the humanized Il1rl2 gene in the genome of a genetically modified rodent includes a nucleotide sequence of a human IL1RL2 gene (or "a human IL1RL2 nucleotide sequence") and a nucleotide sequence of an endogenous rodent Il1rl2 gene (or "an endogenous rodent Il1rl2 nucleotide sequence"), wherein the human IL1RL2 nucleotide sequence encodes a polypeptide substantially identical to the ectodomain of the human IL1RL2 protein encoded by the human IL1RL2 gene. Such human IL1RL2 nucleotide sequence is also referred to as encoding substantially the ectodomain of a human IL1RL2 protein. In some embodiments, the human IL1RL2 nucleotide sequence is a genomic fragment of a human IL1RL2 gene. In some embodiments, the human IL1RL2 nucleotide sequence is a genomic fragment comprising exons 3-8 of a human IL1RL2 gene. In some embodiments, the human IL1RL2 nucleotide sequence is a genomic fragment comprising a 3' portion of intron 2, exons 3-8, and a 5' portion of intron 8 of a human IL1RL2 gene. In some embodiments, the human IL1RL2 nucleotide sequence is a cDNA sequence.

In some embodiments, the humanized Il1rl2 gene in the genome of a genetically modified rodent includes an endogenous rodent Il1rl2 nucleotide sequence and a human IL1RL2 nucleotide sequence, wherein the endogenous rodent Il1rl2 nucleotide sequence encodes a polypeptide substantially identical to the transmembrane-cytoplasmic sequence of an endogenous rodent Il1rl2 protein. Such rodent/Il1rl2 nucleotide sequence is also referred to as encoding substantially the transmembrane-cytoplasmic sequence of the endogenous rodent Il1rl2 protein. In some embodiments, the endogenous rodent Il1rl2 nucleotide sequence present in a humanized Il1rl2 gene encodes the transmembrane-cytoplasmic sequence of the endogenous rodent Il1rl2 protein. In some embodiments, the endogenous rodent Il1rl2 nucleotide sequence present in a humanized Il1rl2 gene comprises the remaining exons downstream of exon 8 in the endogenous rodent Il1rl2 gene. In some embodiments, the endogenous rodent Il1rl2 nucleotide sequence present in a humanized Il1rl2 gene comprises a 3' portion of intron 8 and the remaining exons downstream of exon 8 in the endogenous rodent Il1rl2 gene.

In some embodiments, the humanized Il1rl2 gene in the genome of a genetically modified rodent includes an endogenous rodent Il1rl2 nucleotide sequence upstream (5') of a human IL1RL2 nucleotide sequence, wherein the endogenous rodent Il1rl2 nucleotide sequence encodes a polypeptide substantially identical to the signal peptide of the endogenous rodent Il1rl2 protein. Such rodent Il1rl2 nucleotide sequence is also referred to as encoding substantially the signal peptide of an endogenous rodent Il1rl2 protein. In some embodiments, the endogenous rodent Il1rl2 nucleotide sequence encoding a polypeptide substantially identical to the signal peptide of the endogenous rodent Il1rl2 protein comprises exons 1-2 of the endogenous rodent Il1rl2 gene; and in some embodiments, the endogenous rodent Il1rl2 nucleotide sequence includes exons 1-2 and a 5' portion of intron 2 of an endogenous rodent Il1rl2 gene.

In some embodiments, the humanized Il1rl2 gene is operably linked to endogenous rodent Il1rl2 regulatory sequences, e.g., a 5' transcriptional regulatory sequence(s) such as promoter and/or enhancers, such as expression of the humanized Il1rl2 gene is under control of the rodent Il1rl2 5' regulatory sequence(s).

In some embodiments, the humanized Il1rl2 gene is at an endogenous rodent Il1rl2 locus. In some embodiments, the humanized Il1rl2 gene is at a locus other than an endogenous rodent Il1rl2 locus; e.g., as a result of random integration. In some embodiments where the humanized Il1rl2 gene is at a locus other than an endogenous rodent Il1rl2 locus, the rodents are incapable of expressing a rodent Il1rl2 protein, e.g., as a result of inactivation (e.g., deletion in full or in part) of the endogenous rodent Il1rl2 gene.

In some embodiments where a humanized Il1rl2 gene is at an endogenous rodent Il1rl2 locus, the humanized Il1rl2 gene results from a replacement of a nucleotide sequence of an endogenous rodent Il1rl2 gene at the endogenous rodent Il1rl2 locus with a nucleotide sequence of a human IL1RL2 gene.

In some embodiments, the nucleotide sequence of an endogenous rodent Il1rl2 gene at an endogenous rodent Il1rl2 locus that is being replaced is a genomic fragment of an endogenous rodent Il1rl2 gene that encodes substantially the ectodomain of the rodent Il1rl2 protein. In some embodiments, a rodent genomic fragment being replaced comprises exons 3-8 of an endogenous rodent Il1rl2 gene.

In some embodiments, the nucleotide sequence of a human IL1RL2 gene that replaces a genomic fragment of a rodent Il1rl2 gene at an endogenous rodent Il1rl2 locus is a cDNA sequence. In some embodiments, the human IL1RL2 nucleotide sequence that replaces a genomic fragment of a rodent Il1rl2 gene at an endogenous rodent Il1rl2 locus is a genomic fragment of a human IL/RL2 gene. In some embodiments, a genomic fragment of a human IL1RL2 gene that replaces a genomic fragment of a rodent Il1rl2 gene at an endogenous rodent Il1rl2 locus includes exons, in full or in part, of a human IL1RL2 gene, that encode substantially the ectodomain of the human IL1RL2 protein. In some embodiments, the human genomic fragment comprises exons 3-8 of a human IL1RL2 gene.

In some embodiments, the genomic sequence of an endogenous rodent Il1/rl2 gene that remains at an endogenous rodent Il1rl2 locus after the humanization replacement and is operably linked to the inserted human IL1RL2 nucleotide sequence encodes substantially the transmembrane-cytoplasmic sequence of the endogenous rodent Il1rl2 protein. In some embodiments, the genomic sequence of an endogenous rodent Il1rl2 gene that remains at an endogenous rodent Il1rl2 locus after the humanization replacement includes the exons downstream of exon 8 of the endogenous rodent Il1rl2 gene.

In some embodiments, the genomic sequence of an endogenous rodent Il1rl2 gene that remains at an endogenous rodent Il1rl2 locus after the humanization replacement and is operably linked to the inserted human IL1RL2 nucleotide sequence encodes substantially the signal peptide of the endogenous rodent Il1rl2 protein. In some embodiments, the genomic sequence of an endogenous rodent Il1rl2 gene that remains at an endogenous rodent Il1rl2 locus after the humanization replacement includes exons 1-2 of the endogenous rodent Il1rl2 gene.

In some embodiments, in circumstances where an endogenous rodent Il1rl2 protein and a human IL1RL2 protein share common amino acids near the junction between the transmembrane domain and the ectodomain, it may not be necessary to insert a human IL1RL2 nucleotide sequence that encodes precisely the ectodomain of the human IL1RL2 protein. It is possible to insert a slightly longer or shorter nucleotide sequence of a human IL1RL2 gene, which encodes substantially the ectodomain of the human IL1RL2 protein, in operable linkage to a genomic sequence of an endogenous rodent Il1rl2 gene that encodes substantially the transmembrane domain (and the cytoplasmic domain) of the endogenous rodent Il1rl2 protein, such that the humanized Il1rl2 protein encoded by the resulting humanized Il1rl2 gene includes an ectodomain that is identical with the ectodomain of the human IL1RL2 protein and a transmembrane domain that is identical with the transmembrane domain of the endogenous rodent Il1rl2 protein.

In some embodiments, a genomic fragment comprising exons 3-8 of an endogenous rodent Il1rl2 gene at an endogenous rodent Il1rl2 locus has been replaced with a genomic fragment comprising exons 3-8 of a human IL1RL2 gene. As a result, a humanized Il1rl2 gene is formed at the endogenous rodent Il1rl2 locus and comprises exons 1-2 of the endogenous rodent Il1rl2 gene, exons 3-8 of the human IL1RL2 gene, and the remaining exons downstream of exon 8 of the endogenous rodent Il1rl2 gene.

In some embodiments, a rodent provided herein is heterozygous for a humanized Il1rl2 gene in its genome. In some embodiments, a rodent provided herein is homozygous for a humanized Il1rl2 gene in its genome.

In some embodiments, a humanized Il1rl2 gene results in an expression of the encoded humanized Il1rl2 protein in a rodent. In some embodiments, a humanized Il1rl2 protein is expressed in a pattern comparable with, or substantially the same as, a counterpart rodent Il1rl2 protein in a control rodent (e.g., a rodent without the humanized Il1rl2 gene). In some embodiments, a humanized Il1rl2 protein is expressed at a level comparable with, or substantially the same as, a counterpart rodent Il1rl2 protein in a control rodent (e.g., a rodent without the humanized Il1rl2 gene). In some embodiments, a humanized Il1rl2 protein is expressed and detected at the cell surface, e.g., but not limited to, surface of cells such as keratinocytes, monocytes, macrophages, neutrophils, bronchial and intestinal epithelial cells among others. In the context of comparing a humanized gene or protein in a humanized rodent with an endogenous rodent gene or protein in a control rodent, the term "comparable" means that the molecules or levels being compared may not be identical to one another but are sufficiently similar to permit comparison there between so that conclusions may reasonably be drawn based on differences or similarities observed. In some embodiments, the term "substantially the same", in referring to expression levels, include levels being compared that are not different from one another by more than 20%, 19%, 18%, 17%, 16%, 15%, 14%, 13%, 12%, 11%, 10%, 9%, 8%, 7%, 6%, 5%, 4%, 3%, 2%, or 1%.

In some embodiments, rodents disclosed herein are incapable of expressing a rodent Il1rl2 protein, e.g., as a result of inactivation (e.g., deletion in full or in part) or replacement (in full or in part) of the endogenous rodent Il1rl2 gene.

IL-36 Ligands Humanization

The rodents disclosed herein also comprise in the germline genes encoding human IL-36α, β, and γ ligands.

TABLE 2

| SEQ ID NO | Description | Features |
|---|---|---|
| 8 | *Homo sapiens* IL1F6 (IL-36α) mRNA, NM_014440.2 | Length: 888 bp CDS: 412-888 |
| 9 | *Homo sapiens* IL1F6 (IL-36α) protein, NP_055255.1 | Length: 158aa Mature: 6-158 |
| 10 | *Mus musculus* Il1f6 (Il-36α) mRNA, NM_019450.3 | Length: 883 bp CDS: 162-644 |
| 11 | *Mus musculus* Il1f6 (Il-36α) Protein NP_062323.1 | Length: 160 aa Mature: 8-160 |
| 12 | *Rattus norvegicus* Il1f6 (Il-36α) mRNA, NM_001106554.1 | Length: 869 bp CDS: 162-644 |
| 13 | *Rattus norvegicus* Il1f6 (Il-36α) Protein, NP_001100024.1 | Length: 160 aa |

In some embodiments, a rodent disclosed herein has a genome comprising a human IL-36α gene that encodes a human IL-36α protein. References to a "human IL-36α gene" include a human genomic DNA that encodes a human IL-36α protein and comprises human IL-36α promoter. A human IL-36α protein can be the mature form or the precursor form of a human IL-36α protein. In some embodiments, a human IL-36α protein comprises the amino acid sequence of SEQ ID NO: 9.

In some embodiments, a human IL-36α gene is at an endogenous rodent Il-36α locus. In some embodiments, a human IL-36α gene is at a locus other than an endogenous rodent Il-36α locus; e.g., as a result of random integration. In some embodiments where the human IL-36α gene is at a locus other than an endogenous rodent Il-36α locus, the rodents are incapable of expressing a rodent Il-36α protein, e.g., as a result of inactivation (e.g., deletion in full or in part) of the endogenous rodent Il-36α gene.

In some embodiments, a human IL-36α gene replaces an endogenous rodent Il-36α gene at an endogenous rodent Il-36α locus.

In some embodiments, a rodent provided herein is heterozygous for a human IL-36α gene in its genome. In other embodiments, a rodent provided herein is homozygous for a human IL-36α gene in its genome.

In some embodiments, a human IL-36α gene results in an expression of the encoded human IL-36α protein in a rodent, e.g., in serum, at mucosal sites, such as skin, intestinal epithelium, lungs, and in various types of cells of immune system (e.g., monocytes, macrophages, T cells, dendritic cells). In some embodiments, the human IL-36α protein is expressed in a pattern comparable with, or substantially the same as, a counterpart rodent Il-36α protein in a control rodent (e.g., a rodent without the human IL-36α gene). In some embodiments, the human IL-36α protein is expressed at a level comparable with, or substantially the same as, a counterpart rodent Il-36α protein in a control rodent (e.g., a rodent without the human IL-36α gene), e.g., in serum, at mucosal sites (e.g., such as skin, intestinal epithelium, lungs), and/or in immune cells (e.g., monocytes, macrophage, T cells, dendritic cells).

In some embodiments, rodents disclosed herein are incapable of expressing a rodent Il-36α protein, e.g., as a result of inactivation (e.g., deletion in full or in part) or replacement (in full or in part) of the endogenous rodent Il-36α gene.

TABLE 3

| SEQ ID NO | Description | Features |
|---|---|---|
| 14 | *Homo sapiens* IL1F8 (IL-36β), transcript variant 1, mRNA, NM_014438.4 | Length: 1186 bp CDS: 109-603 |
| 15 | *Homo sapiens* IL1F8 (IL-36β) protein, NP_055253.2 | Length: 164 aa |
| 16 | *Mus musculus* Il1f8 (Il-36β) mRNA, NM_027163.4 | Length: 790 bp CDS: 66-617 |
| 17 | *Mus musculus* Il1f8 (Il-36β) Protein NP_081439.1 | Length: 183 aa |
| 18 | *Rattus norvegicus* Il1f8 (Il-36β) mRNA, NM_001108570.1 | Length: 587 bp CDS: 92-415 |
| 19 | *Rattus norvegicus* Il1f8 (Il-36β) Protein, XP_006233676 | Length: 179 aa |

In some embodiments, the rodents disclosed herein have a genome comprising a human IL-36β gene that encodes a human IL-36β protein. References to a "human IL-36β gene" include a human genomic DNA that encodes a human IL-36β protein and comprises human IL-36β promoter. A human IL-36β protein can be the mature form or the precursor form of a human IL-36β protein. In some embodiments, a human IL-36β protein comprises the amino acid sequence of SEQ ID NO: 15.

In some embodiments, a human IL-36β gene is at an endogenous rodent Il-36β locus. In some embodiments, a human IL-36β gene is at a locus other than an endogenous rodent Il-36β locus; e.g., as a result of random integration. In some embodiments where the human IL-36β gene is at a locus other than an endogenous rodent Il-36β locus, the rodents are incapable of expressing a rodent Il-36β protein, e.g., as a result of inactivation (e.g., deletion in full or in part) of the endogenous rodent Il-36β gene.

In some embodiments, a human IL-36β gene replaces an endogenous rodent Il-36β gene at an endogenous rodent Il-36β locus.

In some embodiments, a rodent provided herein is heterozygous for a human IL-36β gene in its genome. In other embodiments, a rodent provided herein is homozygous for a human IL-36β gene in its genome.

In some embodiments, a human IL-36β gene results in an expression of the encoded human IL-36β protein in a rodent, e.g., in serum, at mucosal sites (e.g., such as skin, intestinal epithelium, lungs), and/or in immune cells (e.g., monocytes, macrophage, T cells, dendritic cells). In some embodiments, the human IL-36β protein is expressed in a pattern comparable with, or substantially the same as, a counterpart rodent Il-36β protein in a control rodent (e.g., a rodent without the human IL-36β gene). In some embodiments, the human IL-36β protein is expressed at a level comparable with, or substantially the same as, a counterpart rodent Il-36β protein in a control rodent (e.g., a rodent without the human IL-36β gene), e.g., in serum, at mucosal sites, such as skin, intestinal epithelium, lungs, and in various types of cells of immune system (e.g., monocyte, macrophages, T cells, dendritic cells).

In some embodiments, rodents disclosed herein are incapable of expressing a rodent I Il-36β protein, e.g., as a result of inactivation (e.g., deletion in full or in part) or replacement (in full or in part) of the endogenous rodent Il-36β gene.

TABLE 4

| SEQ ID NO | Description | Features |
|---|---|---|
| 20 | Homo sapiens IL1F9 (IL-36γ), transcript variant 1, mRNA, NM_019618.3 | Length: 1212 bp CDS: 80-589 |
| 21 | Homo sapiens IL1F9 (IL-36γ) protein, NP_062564.1 | Length: 169 aa |
| 22 | Mus musculus Il1f9 (Il-36γ) mRNA, NM_153511.3 | Length: 1647 bp CDS: 295-876 |
| 23 | Mus musculus Il1f9 (Il-36γ) Protein, Q8R460.1 | Length: 164 aa |
| 24 | Rattus norvegicus Il1f9 (Il-36γ) mRNA, NM_001113790.1 | Length: 1395 bp CDS : 166-663 |
| 25 | Rattus norvegicus Il1f9 (Il-36γ) Protein, NP_001107262.1 | Length: 165 aa |

In some embodiments, this invention provides a rodent whose genome contains a human IL-36γ gene that encodes a human IL-36γ protein. References to a "human IL-36γ gene" include a human genomic DNA that encodes a human IL-36γ protein and comprises human IL-36γ promoter. In some embodiments, a human IL-36γ protein can be the mature form or the precursor form of a human IL-36γ protein. In some embodiments, a human IL-36γ protein comprises the amino acid sequence of SEQ ID NO: 21.

In some embodiments, a human IL-36γ gene is at an endogenous rodent Il-36γ locus.

In some embodiments, a human IL-36γ gene is at a locus other than an endogenous rodent Il-36γ locus; e.g., as a result of random integration. In some embodiments where the human IL-36γ gene is at a locus other than an endogenous rodent Il-36γ locus, the rodents are incapable of expressing a rodent Il-36γ protein, e.g., as a result of inactivation (e.g., deletion in full or in part) of the endogenous rodent Il-36γ gene.

In some embodiments, a human IL-36γ gene replaces an endogenous rodent Il-36γ gene at an endogenous rodent Il-36γ locus.

In some embodiments, a rodent provided herein is heterozygous for a human IL-36γ gene in its genome. In other embodiments, a rodent provided herein is homozygous for a human IL-36γ gene in its genome.

In some embodiments, a human IL-36γ gene results in an expression of the encoded human IL-36γ protein (e.g., a protein identical with a human IL-36γ protein) in a rodent, e.g., in serum, at mucosal sites, such as skin, intestinal epithelium, lungs, and in various types of cells of immune system (e.g., monocyte, macrophages, T cells, dendritic cells). In some embodiments, the human IL-36γ protein is expressed in a pattern comparable with, or substantially the same as, a counterpart rodent Il-36γ protein in a control rodent (e.g., a rodent without the human IL-36γ gene). In some embodiments, the human IL-36γ protein is expressed at a level comparable with, or substantially the same as, a counterpart rodent Il-36γ protein in a control rodent (e.g., a rodent without the human IL-36γ gene), e.g., in serum, at mucosal sites (e.g., such as skin, intestinal epithelium, lungs), and/or in immune cells (e.g., monocytes, macrophage, T cells, dendritic cells).

In some embodiments, rodents disclosed herein are incapable of expressing a rodent Il-36γ protein, e.g., as a result of inactivation (e.g., deletion in full or in part) or replacement (in full or in part) of the endogenous rodent Il-36γ gene.

In some embodiments, rodents are provided whose genome comprise a replacement of a contiguous genomic fragment encompassing the coding sequences for all three Il-36 ligands at an endogenous locus with a contiguous nucleic acid comprising coding sequences for three ligands that are substantially identical with a human IL-36α, β, and γ, respectively. In some embodiments, the resulting locus comprises, from 5' to 3', (i) a human IL-36β gene, (ii) a human IL-36γ gene, and (iii) the reverse strand of a human IL-36α gene.

Phenotypes of Quadruple Humanized Rodents

The genetically modified rodents disclosed herein do not develop any spontaneous diseases at steady state; however, these rodents do display shortened colons and increased expression of proinflammatory mediators in the skin as compared to age-matched control rodents without the humanization, at both steady state and disease state (e.g., after DSS or IMQ treatment). In some embodiments, a genetically modified rodent displays a colon length that is at least 10%, 15%, 20%, 25%, 30%, 35%, 40%, 45%, or 50% shorter than a control rodent at steady state or disease state.

In some embodiments, a genetically modified rodent displays a colon length that is 10% to 15% (+/−5%) shorter than a control rodent at steady state. In some embodiments, a genetically modified rodent displays a colon length that is 15% to 20% (+/−5%) shorter than a control rodent at steady state. In some embodiments, a genetically modified rodent displays a colon length that is 10% to 20% (+/−5%) shorter than a control rodent at steady state.

In other embodiments, a genetically modified rodent displays a colon length that is 20% to 40% (+/−5%) shorter than a control rodent at disease state (e.g., after DSS or oxazolone treatment). In other embodiments, a genetically modified rodent displays a colon length that is 30% to 40% (+/−5%) shorter than a control rodent at disease state (e.g., after DSS or oxazolone treatment). In other embodiments, a genetically modified rodent displays a colon length that is 200 to 300 (+/−5%) shorter than a control rodent at disease state (e.g., after DSS or oxazolone treatment). In other embodiments, a genetically modified rodent displays a colon length that is 25% to 35% (+/−5%) shorter than a control rodent at disease state (e.g., after DSS or oxazolone treatment).

Although the genetically modified rodents disclosed herein do not develop any spontaneous diseases at steady state, they have been shown to display enhanced skin and intestinal inflammation in experimentally induced skin and intestinal inflammation models (e.g., preclinical models of psoriasis and IBD, respectively).

In some embodiments, DSS is used to induce chronic colitis. In some embodiments, DSS is administered to rodents through drinking water at least 0.5%, at least 1%, at least 1.5%, at least 2.5%. In some embodiments, DSS is administered to rodents through drinking water at not more than 10%, 9%, 8%, 7%, 6%, or 5%. In some embodiments, drinking water containing DSS at 1.5%-3% is given to rodents. In some embodiments, drinking water containing DSS at 0.5%-3% is given to rodents. In some embodiments, drinking water containing DSS at 1%-3% is given to rodents. In some embodiments, drinking water containing DSS at 2%-3% is given to rodents. In some embodiments, drinking water containing DSS at 2.5%-3% is given to rodents. In some embodiments, drinking water containing DSS at 0.5%-2.5% is given to rodents. In some embodiments, drinking water containing DSS at 0.5%-2% is given to rodents. In some embodiments, drinking water containing DSS at 0.5%-1.5% is given to rodents. In some embodiments, drinking water containing DSS at 0.5%-1% is given to rodents. In some embodiments, drinking water containing DSS at 1%-2.5% is given to rodents. In some embodiments, drinking water containing DSS at 1.5%-2% is given to rodents.

In some embodiments, administration of DSS can be performed for a period of 5, 6, 7, 8, 9, 10, 11, 12, 13, 14, 15, 16, 17, 18, 19, 20 or more days, and can be continuous or interrupted by days without a DSS administration. In some embodiments, rodents are provided with drinking water containing 2.5% DSS for 7 days, then 1.5% DSS for 5 days, followed by distilled water until 27-30 days before analysis. In some embodiments, rodents are provided with drinking water containing 3% DSS for 7 days, then 2% DSS for 13 days, followed by distilled water until 27-30 days before analysis. In some embodiments, DSS is not given for the total period. In some embodiments, rodents are provided with drinking water containing 2.5% DSS for 7 days, followed by 11 days of distilled water, then 1.5% DSS for 4 days, followed by 5 days of distilled water—for a total of 27 days before analysis. In some embodiments, rodents are provided with drinking water containing 3% DSS for 7 days, followed by 13 days of water, then 2% DSS for 4 days, followed by 6 days of distilled water until 30 days before analysis.

In some embodiments, oxazolone is used to induce colitis. In some embodiments, oxazolone is given to rodents intrarectally to induce colitis. In some embodiments, oxazolone is given to rodents intrarectally in three administrations to induce colitis. In some embodiments, oxazolone is applied to rodents topically for pre-sensitization prior to intrarectal administration. In some embodiments, oxazolone is given to a rodent for pre-sensitization by topical application of a solution of oxazolone (e.g., 3% solution of oxazolone dissolved in 100% ethanol) on the shaved skin, followed by a three intrarectal administrations of a solution of oxazolone (e.g., 1.0-2.0% N oxazolone dissolved in 50% ethanol). In some embodiments, the pre-sensitization employs a solution of 1.5%, 2.0%, 2.5%0, 3.0%, 3.5%, or 4.0% oxazolone dissolved in 100% ethanol. In some embodiments, the intrarectal administrations employ a solution of 1.0%, 1.1%, 1.2%, 1.3%, 1.5%, 1.6%, 1.7%, 1.8%, 1.9% or 2.0% of oxazolone dissolved in 50% ethanol. In some embodiments, the intrarectal administration is performed several days, e.g., 3, 4, 5, 6 or 7 days, after the pre-sensitization. In some embodiments, oxazolone is given to a rodent by topical application on the skin in a solution of 3.0% oxazolone dissolved in 100% ethanol, followed by three intrarectal administrations of a solution of 1.0-2.0% oxazolone dissolved in 50, ethanol on days 5, 6 and 7.

In some embodiments, the extent of colitis is evaluated by scoring the following features: inflammation (severity and extent), epithelial changes (erosion/ulcer), changes in the crypts (crypt loss, cryptitis/crypt abscess, regeneration/hyperplasia, goblet cell loss), submucosal edema and percentage of tissue area with pathology relative to the total tissue area on the slide. A 0-4 scoring scale is used: 0-0-within normal limits, 1-minimal, 2-mild, 3-moderate and 4-severe. A total pathology score is calculated for each rodent animal by adding the individual histopathological feature scores. In some embodiments, colitis is evaluated by measuring the level of Lipocalin-2 (Lcn2) in fecal samples. In some embodiments, colitis is measured by measuring the level of Myeloperoxidase (MPO) activity in colon homogenates. In some embodiments, colitis is evaluated by measuring the levels of inflammatory cytokines in colon homogenates.

In some embodiments, the genetically modified rodents display an increased intestinal pathology score, e.g., by at least 50%, 60%, 70%, 80%, 90%, 100%, 200%, 300%, 400% or more, as compared to wild type control rodents that have undergone the same DSS administration. In some embodiments, the genetically modified rodents display an increased intestinal pathology score by, e.g., 500%-400%, 500%-300%, 50%-200%, 50%-100%, 100%-400%, 100%-300%, 100-200%, or 200%-400%, as compared to wild type control rodents that have undergone the same DSS administration. In some embodiments, the genetically modified rodents exhibit an increased level of Myeloperoxidase ("MPO") in colon homogenates, e.g., by at least 50%, 60%, 70%, 80%, 90%, 100%, 200%, 300%, 400%, or more, as compared to wild type control rodents that have undergone the same DSS administration. In some embodiments, the genetically modified rodents display an increased level of MPO in colon homogenates by, e.g., 50%-400%, 50%-300%, 50%-200%, 50%-100%, 100%-400%, 100%-300%, 100-200%, or 200%-400%, as compared to wild type control rodents that have undergone the same DSS administration. In some embodiments, the genetically modified rodents exhibit an increased level of fecal Lcn, e.g., by at least 10%, 20%, 30%, 40%, 50%, 60%, 70%, 80%, 90%, 100%, 200%, 300%, 400%, or more, as compared to wild type control rodents that have undergone the same DSS administration. In some embodiments, the genetically modified rodents exhibit an increased mRNA expression and/or protein level of one or more proinflammatory mediators (e.g., KC-GRO, IL-6, IL-1β, TNFα, IL-21, IL-12p40, IL-17f, IL-17a, and IL-17c) in colon homogenates, e.g., by at least 20%, 30%, 40%, 50%, 60%, 70%, 80%, 90%, 100%, 200%, 300%, 400%, 500%, 600%, 700%, 800%, 900% or more, as compared to wild type control rodents that have undergone the same DSS administration. In some embodiments, the genetically modified rodents exhibit an increased mRNA expression and/or protein level of one or more proinflammatory mediators in colon homogenates by, e.g., 20%-900%, 200%-800%, 20%-700%, 20%-600%, 20%-500%, 20%-400%, 20%-300%, 20%-200%, or 20%-100%. In some embodiments, the genetically modified rodents exhibit an increased mRNA expression and/or protein level of one or more proinflammatory mediators in colon homogenates by, e.g., 30%-900, 30%-800%, 30%-700%, 30%-600%, 30%-500%, 30%-400%, 30%-300%, 30%-200%, or 30%-100%. In some embodiments, the genetically modified rodents exhibit an increased mRNA expression and/or protein level of one or more proinflammatory mediators in colon homogenates by, e.g., 40%-900%, 40%-800%, 40%-700%, 40%-600%, 40%-500%, 40-400%, 40%-300%, 40%-200%, or 40%-100%. In some embodiments, the genetically modified rodents exhibit an increased mRNA expression and/or protein level of one or more proinflammatory mediators in colon homogenates by, e.g., 50%-900%, 50%-800%, 50%-700%, 50%-600%, 50%-500%, 50%-400%, 50%-300%, 50%-200%, or 50%-100%.

In some embodiments, IMQ is applied topically to the skin of a rodent to induce skin inflammation. In some embodiments, IMQ is provided in a carrier suitable for topical application, e.g., a cream, a gel, including commercially available IMQ creams (e.g., such as those from Aldara). In some embodiments, to induce skin inflammation, IMQ is applied to the rodent skin daily at a daily dose of 1 to 5 mg, 2 to 4 mg, or 3-3.5 mg, for a period of 2, 3, 4, 5, 6, 7, 8, 9, 10 days or longer. In some embodiments, a daily topical application at a daily dosage of about 3.125 mg for 4 days is suitable for inducing acute skin inflammation, and a daily topical application at a daily dosage of about 3.125 mg for 9 days is suitable for inducing chronic skin inflammation. In some embodiments, IMQ is applied topically for multiple rounds (e.g., 2, 3 or 4 rounds), with 4-5 consecutive days of IMQ application followed by 2 days of no IMQ application for each round, before analysis or assay is performed. In a specific embodiment. IMQ is applied topically for two rounds, with 5 consecutive days of IMQ application followed by 2 days of no IMQ application for the first round, then 4 consecutive days of IMQ application for the second round, before analysis (see, e.g., FIGS. 7A-7C). In some embodiments, the severity of inflammation can be evaluated by (i) using an adapted version of the clinical Psoriasis Area and Severity Index based on measuring erythema, scaling and thickening of the skin; (ii) performing histopathological analysis of skin tissues, e.g., to evaluate the presence of parakeratosis, orthokeratosis, Munro's microabscess, acanthosis, epidermal ulceration, inflammation in the dermis and hypodermis, blood vessel congestion in the dermis and hypodermis, follicular hyperkeratosis and epithelial hyperplasia, and to determine a total pathology score; (iii) measuring mRNA expression and/or protein levels of proinflammatory mediators in the skin homogenates, including e.g., mRNA expression and/or protein levels of Cxcl1, IL-17f, IL-17a, IL-23a, S100A8 and Defb4, among others; and (iv) a combination of (i)-(iii).

In some embodiments, the genetically modified rodents display an increased skin pathology score, e.g., by at least 20%, 30%, 40%, 50%, 60%, 70%, 80%, 90%, 100%, 200% or more, as compared to wild type control rodents that have undergone the same IMQ administration. In some embodiments, the genetically modified rodents exhibit an increased mRNA expression and/or protein level of one or more proinflammatory mediators (e.g., but not limited to, Cxcl1, IL-17f, IL-17a, IL-23a, S100A8 and Defb4) in skin homogenates, e.g., by at least 20%, 30%, 40%, 50%, 60%, 70%, 80%, 90%, 100%, 200%, 300%, or more, as compared to wild type control rodents that have undergone the same IMQ administration. In some embodiments, the genetically modified rodents at steady state exhibit an increased mRNA expression and/or protein level of one or more proinflammatory mediators (e.g., but not limited to, Cxcl1, IL-17f, IL-17a, IL-23a, S100A8 and Defb4) in skin homogenates, e.g., by at least 20%, 30%, 40%, 50%, 60%, 70%, 80%, 90%, 100%, 200%, 300%, or more, as compared to wild type control rodents at steady state.

Figures 3A, 3B, 3C:
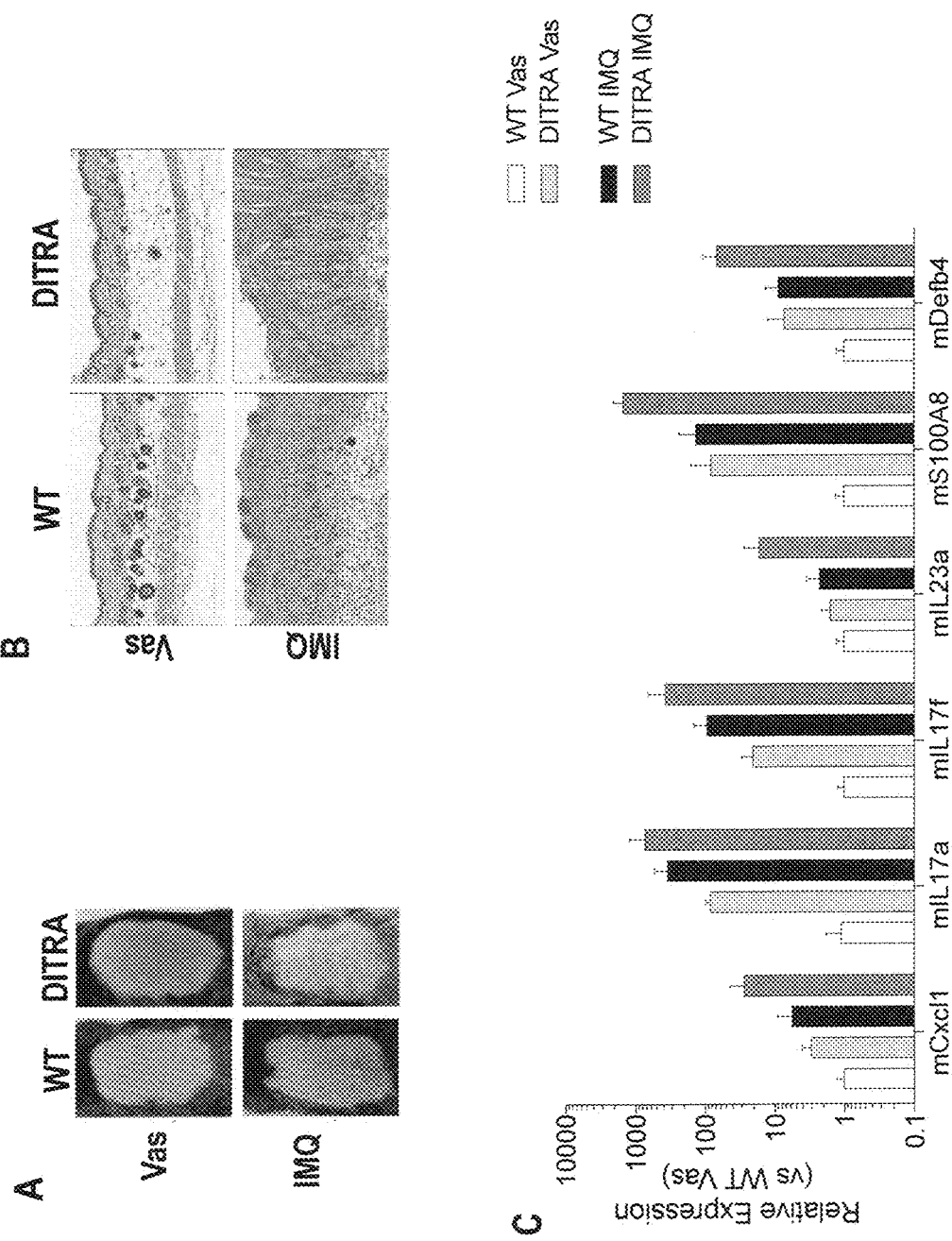
FIGS. 3A-3E show embodiments of the present invention, showing enhanced IMQ-induced skin inflammation in humanized DITRA-like mice. DITRA-like (also abbreviated as "DITRA" in the figures herein) and wild-type (WT) mice were treated with topical application of IMQ for 4 consecutive days. On day 5, back skin samples were collected for subsequent histopathological evaluation and qRT-PCR. (3A) Representative skin appearance of DITRA-like and WT mice at day 5 topically treated with Vaseline ("Vas", control) or IMQ-containing cream (Aldara) for 4 consecutive days. (3B) Representative haematoxylin and eosin ("H&E") staining of Vaseline- and IMQ-treated skin from DITRA-like and WT mice. (3C) mRNA expression of pro-inflammatory molecules in the skin of DITRA and WT mice treated daily with Vaseline or IMQ-containing cream (n=10 per each group). After topical application of IMQ for 4 consecutive days, on day 5, back skin samples were collected from Il1rl2 single humanized mice ("1H"), DITRA-like mice and wild type mice for subsequent histopathological evaluation and qRT-PCR. In each group of bars from left to right are: WT Vas, DITRA Vas, WT IMQ, and DITRA IMQ. (3D) Representative skin appearance of 1H, DITRA-like and WT mice at day 5 topically treated with Vaseline (control) or IMQ-containing cream (Aldara) for 4 consecutive days. (3E) mRNA expression of pro-inflammatory molecules in the skin of 1H, DITRA and WT mice treated daily with Vaseline or IMQ-containing cream (n=10 per each group). In each group of bars from left to right are: WT Vas, 1H Vas, DITRA-LIKE Vas, WT IMQ, 1H IMQ, and DITRA-LIKE IMQ.
Figures 3D, 3E:
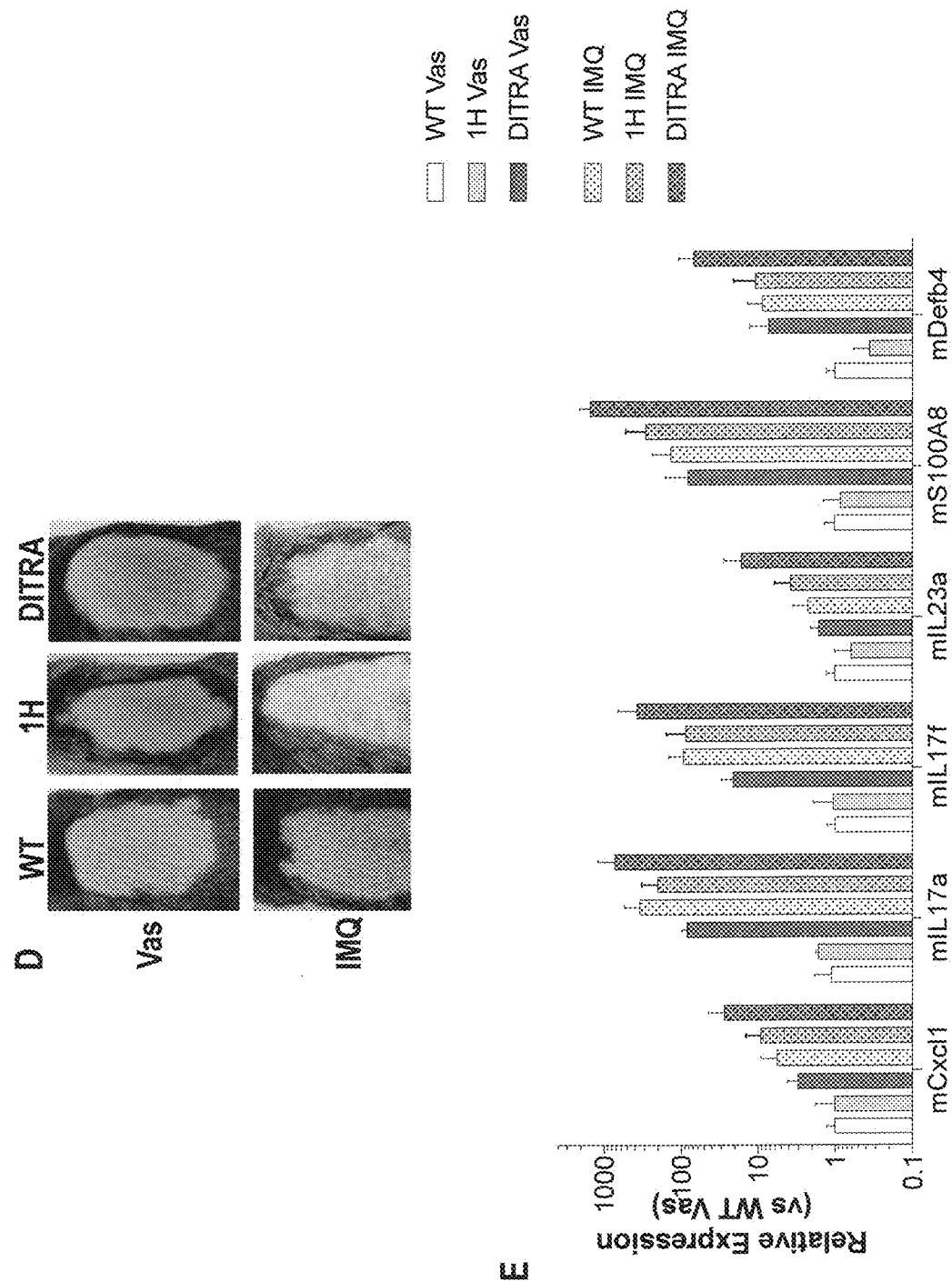

For IMQ induced-skin inflammation, single Il1rl2 humanized mice exhibited phenotypes similar to a wild type rodent, as reflected in histopathology and RNA expression of proinflammatory molecules in the skin (see FIGS. 3D and 3E). On the other hand, DITRA-like mice (i.e., quadruple-humanized mice comprising humanized Il1rl2 and human IL1F6. IL1F8, and IL1F9) developed increased skin inflammation compared to both WT and 1H mice after IMQ application (see FIGS. 3D and 3E).

Tissues and Cells of Genetically Modified Rodents

In some embodiments, disclosed herein is an isolated cell or tissue from a rodent animal as described herein. In some embodiments, a cell is selected from a dendritic cell, lymphocyte (e.g., a B or T cell), macrophage and a monocyte. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof. In some embodiments, the isolated cell or tissue comprises in its genome the quadruple humanization features described herein.

Compositions and Methods for Making Quadruple Humanized Rodents

Further aspects of this disclosure are directed to methods for making a genetically modified rodent described above, as well as nucleic acid vectors and rodent embryonic stem cells suitable for use in making a genetically modified rodent.

A quadruple-humanized rodent, i.e., a rodent comprising humanized Il1rl2 and human IL1F6, IL1F8, and IL1F9 genes, can be generated by making a single Il1rl2 humanized rodent strain, and a Il1f6, Il1f8, and Il1f9 triple human rodent strain, followed by breeding the single-humanized and triple-human strains together to obtain a quadruple-humanized rodent. The term "breeding" or "crossing", as used herein in reference to rodents, refers to the mating of the rodents to produce offspring. Those skilled in the art would understand that more than one cross may be needed in order to achieve homozygosity.

In some embodiments, disclosed herein is a targeting vector (or nucleic acid construct) comprises a human nucleotide sequence desired to be integrated into a rodent locus. In some embodiments, the human nucleotide sequence can be a nucleotide sequence of a human IL1RL2 gene that encodes an ectodomain substantially identical to a human IL1RL2 ectodomain, e.g., a nucleotide sequence comprising exons 3-8 of a human IL1RL2 gene. In some embodiments, the human nucleotide sequence can be a nucleotide sequence encompassing the coding sequence for human IL-36α, the coding sequence for human Il-36β and the complement strand of the coding sequence of a human IL-36γ. The targeting vector also includes 5' and 3' rodent sequences flanking the human nucleotide sequence to be integrated, also known as homology arms, that mediate homologous recombination and integration of the human nucleotide sequence into the target rodent locus (e.g., the Il1rl2 locus, or the locus where the rodent Il1f6, Il1f8, and Il1f9 genes are located). In some embodiments, the 5' and 3' flanking rodent sequences are the nucleotide sequences that flank the corresponding rodent nucleotide sequence at the target rodent locus that is to be replaced by the human nucleotide sequence. For example, in embodiments where a rodent ectodomain-encoding nucleotide sequence (e.g., exons 3-8 of a rodent Il1rl2 gene) is replaced with a human ectodomain-encoding sequence (e.g., exons 3-8 of a human IL1RL2 gene), the 5' flanking sequence can include exons 1-2 of the rodent Il1rl2 gene, and the 3' flanking sequence can include the remaining exons downstream of exon 8 of the rodent Il1rl2 gene. In some embodiments where the rodent nucleotide sequence coding for all three IL-36 ligands is to be replaced with a human nucleotide sequence, the 5' flanking sequence can include a rodent nucleotide sequence upstream of the coding sequence of the Il1f6 gene, and the 3' flanking sequence can include a rodent nucleotide sequence upstream of the coding sequence of the Il1f9 gene.

In some embodiments, a targeting vector comprises a selection marker gene. In some embodiments, a targeting vector comprises one or more site-specific recombination sites. In some embodiments, a targeting vector comprises a selection marker gene, flanked by site-specific recombination sites, such that the selection marker gene can be deleted as a result of recombination between the sites.

In exemplary embodiments, a bacterial artificial chromosome (BAC) clone carrying a rodent genomic fragment can be modified using bacterial homologous recombination and VELOCIGENE® technology (see, e.g., U.S. Pat. No. 6,586,251 and Valenzuela et al. (2003) Nature Biotech. 21(6):652-659; which are incorporated herein by reference in their entireties). As a result, a rodent genomic sequence is deleted from the original BAC clone, and a human nucleotide sequence is inserted, resulting in a modified BAC clone carrying a human nucleotide sequence, flanked with 5' and 3' rodent homology arms. In some embodiments, human nucleotide sequence can be a cDNA sequence or a human genomic DNA encoding (i) human IL1RL2 in whole or in part (e.g., the ectodomain of a human IL1RL2 protein), or (ii) all three of human IL1F6, IL1F8, and IL1F9. The modified BAC clone, once linearized, can be introduced into rodent embryonic stem (ES) cells.

In some embodiments, the present invention provides use of a targeting vector as described herein to make a modified rodent embryonic stem (ES) cell. For example, a targeting vector can be introduced into a rodent ES cell by, e.g., electroporation. Both mouse ES cells and rat ES cells have been described in the art. See, e.g., U.S. Pat. Nos. 7,576,259, 7,659,442, 7,294,754, and US 2008-0078000 A1 (all of which are incorporated herein by reference in their entireties) that describe mouse ES cells and the VELOCIMOUSE® method for making a genetically modified mouse; US 2014/0235933 A1 (Regeneron Pharmaceuticals, Inc.), US 2014/0310828 A1 (Regeneron Pharmaceuticals, Inc.), Tong et al. (2010) Nature 467:211-215, and Tong et al. (2011) Nat Protoc. 6(6): doi:10.1038/nprot.2011.338 (all of which are incorporated herein by reference in their entireties) that describe rat ES cells and methods for making a genetically modified rat, which can be used to make a modified rodent embryo, which in turn can be used to make a rodent animal.

In some embodiments, ES cells having a human nucleotide sequence integrated in the genome can be selected. In some embodiments, ES cells are selected based on loss of rodent allele and/or gain of human allele assays. In some embodiments, selected ES cells are then used as donor ES cells for injection into a pre-morula stage embryo (e.g., 8-cell stage embryo) by using the VELOCIMOUSE® method (see, e.g., U.S. Pat. Nos. 7,576,259, 7,659,442, 7,294,754, and US 2008-0078000 A1, all of which are incorporated by reference in their entireties), or methods described in US 2014/0235933 A1 and US 2014/0310828 A1, which are both incorporated by reference in their entireties. In some embodiments, the embryo comprising the donor ES cells is incubated until blastocyst stage and then implanted into a surrogate mother to produce an F0 rodent fully derived from the donor ES cells. Rodent pups bearing a human nucleotide sequence can be identified by genotyping of DNA isolated from tail snips using loss of rodent allele and/or gain of human allele assays.

In some embodiments, rodents heterozygous for a humanized gene can be crossed to generate homozygous rodents.

Methods Employing the Quadruple Humanized Rodents

Rodents disclosed herein provide a useful in vivo system and source of biological materials for identifying and testing compounds useful for treating a disease or condition associated with deregulated IL-36 signaling.

By "disease associated with deregulated IL-36 signaling" it is meant a disease in which abnormal IL-36 signaling is manifested, which could cause directly or indirectly the disease, or exacerbate symptoms of the disease. Non-limiting examples of diseases associated with deregulated IL-36 signaling include generalized pustular psoriasis (GPP or DITRA) (Marrakchi S. et al., N Engl J. Med. 365:620-628 (2011) and Onoufriadis A. et al., Am J. Hum Genet 89:432-437 (2011), which are herein incorporated by reference in their entireties), palmoplantar pustular psoriasis (PPPP) (Bissonnette R. et al., PLoS One 11:e0155215 (2016), which is herein incorporated by reference in its entirety), inflammatory bowel disease (IBD) (Medina-Contreras et al., J Immunol 196:34-38 (2016; Nishida A. et al., Inflamm Bowel Dis 22:303-314 (2016) and Russell S E et al., Mucosal Immunol. 9:1193-1204 (2016) which are herein incorporated by reference in their entireties), rheumatoid and psoriatic arthritis (Frey S. et al., Ann Rheum Dis 72:1569-1574 (2013), which is herein incorporated by reference in its entirety), asthma, chronic obstructive pulmonary disease (Chen H. et al., J. Proteomics 75:2835-2843 (2012), which is herein incorporated by reference in its entirety), chronic kidney disease (Shaik Y. et al., Int J Immunopathol Pharmacol 26:27-36 (2013) which is herein incorporated by reference in its entirety) and ichthyosis (Paller A S et al., J Allergy Clin Immunol 139:152-165 (2017) which is herein incorporated by reference in its entirety).

In some embodiments, compounds that can be evaluated using the rodents disclosed include candidate inhibitors of the IL-36 signaling, for example, but not limited to, a small molecule inhibitor, a nucleic acid-based inhibitor (e.g., siRNA, ribozyme, antisense construct, etc.), an antigen-binding protein (e.g., antibody or antigen-binding fragment thereof), or a blocking peptide/peptide inhibitor.

In some embodiments, a candidate inhibitor is an antibody or antigen-binding fragment thereof. Both monoclonal and polyclonal antibodies are suitable to be tested in a rodent disclosed herein. In some embodiments, an antibody specifically binds to a human IL-36R protein. In some embodiments, an antibody specifically binds to the IL1RL2 subunit of a human IL-36R protein.

Candidate compounds can be evaluated by inducing inflammation, e.g., IMQ induced skin inflammation or DSS-induced intestinal inflammation, in a rodent disclosed herein, and determining whether a candidate compound can treat or inhibit the induced inflammation. The term "treating" or "inhibiting" includes ameliorating the severity, slowing down the progression, eliminating, delaying or preventing the onset of the induced inflammation and symptoms, or a combination thereof.

In some embodiments, a rodent is administered with a candidate compound prior to, together with, or after administration of an agent that induces inflammation. Candidate compounds may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebro ventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection.

In some embodiments, suitable control rodents can include, e.g., humanized rodents without being subjected to an induced inflammation; humanized rodents subjected to an induced inflammation without any compound or with a control compound not expected to have any therapeutic efficacy (e.g., an isotype control antibody); and humanized rodents subjected to an induced inflammation and a compound known to be therapeutically effective.

To assess the efficacy of a candidate compound on skin inflammation, the compound can be administered to the rodent before, during or after the IMQ treatment. In specific embodiments, a candidate compound is administered subcutaneously at or near the skin area where IMQ is applied. A compound is considered to be effective if it inhibits skin inflammation as compared to control rodents not administered the compound. For example, a compound is considered effective if the total pathology score is reduced by 10%, 15%, 20%, 30%, 40%, 50%, 60%, 70%, 80%, 90% or more (e.g., reduced by 20%-90%, 20%-80%, 20%-70%, 20%-60%, 20%-50%, 20%-40%, 30%-90%, 30%-80%, 30%-70%, 30%-60%, 30%-50%, or 30%-40%); or if the concentration(s) of one or more proinflammatory mediators are reduced by 10%, 15%, 20%, 30%, 40%, 50%, 60%, 70%, 80%, 90% or more (e.g., reduced by 20%-90%, 20%-80%, 20%-70%, 20%-60%, 20%-50%, 20%-40%, 30%-90%, 30%-80%, 30%-70%, 30%-60%, 30%-50%, or 30%-40%).

To assess the efficacy of a candidate compound on colon inflammation, the compound can be administered to the rodent before, during or after the DSS or oxazolone treatment. In some embodiments, a candidate compound is administered intraperitoneally a number of days (e.g., 5, 6, 7, 8, or 9 days) after the DSS treatment has started. In some embodiments, a candidate compound is administered intraperitoneally multiple times during the oxazolone treatment; for example, at 2-3 days after a topical application of oxazolone, at one or more of the intrarectal administrations of oxazolone (e.g., at first intrarectal administration of oxazolone, and at third intrarectal administration of oxazolone). A compound is considered to be effective if it inhibits colitis as compared to control DITRA rodents not administered the compound. For example, a compound is considered effective if the total pathology score is reduced by 100%, 15%, 200, 30%, 40%, 50%, 60%, 70%, 80%, 90% or more (e.g., reduced by 20%-90%, 20%-80%, 20%-70%, 20%-60%, 20%-50%, 20%-40%, 30%-90%, 30%-80%, 30%-70%, 30%-60%, 30%-50%, or 30%-40%); if the concentration of one or more proinflammatory mediators are reduced by 10%, 15%, 20%, 30%, 40%, 50%, 60%, 70%, 80%, 90% or more (e.g., reduced by 20%-90%, 20%-80%, 20%-70%, 20%-60%, 20%-50%, 20%-40%, 30%-90%, 30%-80%, 30%-70%, 30%-60%, 30%-50%, or 30%-40%); if the fecal Lcn2 is reduced by 10%, 15%, 20%, 30%, 40%, 50%, 60%, 70%, 80%, 90% or more (e.g., reduced by 20%-90%, 20%-80%, 20%-70%, 20%-60%, 20%-50%, 20%-40%, 30%-90%, 30%-80%, 30%-70%, 30%-60%, 30%-50%, or 30%-40%); if the MPO activity in colon homogenates is reduced by 10%, 15%, 20%, 30%, 40%, 50%, 60%, 70%, 80%, 90% or more (e.g., reduced by 20%-90%, 20%-80%, 20%-70%, 20%-60%, 20%-50%, 20%-40%, 30%-90%, 30%-80%, 30%-70%, 30%-60%, 30%-50%, or 30%-40%); if the colon length is increased by 10%, 15%, 20%, 30%, 40%, 50%, 60%, 70%, 80%, 90% or more (e.g., reduced by 20%-90%, 20%-80%, 20%-70%, 20%-60%, 20%-50%, 20%-40%, 30%-90%, 30%-80%, 30%-70%, 30%-60%, 30%-50%, or 30%-40%); or a combination thereof.

The present description is further illustrated by the following examples, which should not be construed as limiting in any way. The contents of all cited references (including literature references, issued patents, and published patent applications as cited throughout this application) are hereby expressly incorporated by reference in their entireties.

Example 1. Generation of a Quadruple-Humanized Mouse Strain

Two genetically-engineered mouse strains were created using VelociGene® technology (Poueymirou et al., *Nat Biotechnol.* 2007 January; 25(1): 91-9; Valenzuela et al., Nat Biotechnol 2003 June; 21:652-59, which are herein incorporated by reference in their entireties): an Il1rl2 single-humanized mouse strain, and a Il1f6, Il1f8, Il1f9 triple humanized mouse strain. A "quadruple-humanized" strain was generated by breeding the single-humanized and triple-humanized strains together.

Generation of a Single-Humanized Il1rl2 Mouse Strain

A "single-humanized" strain was generated in which the portion of the mouse Il1rl2 gene encoding the extracellular domain of mouse Il Il1rl2 (interleukin-1 receptor-like 2 protein) was replaced with a fragment of the human IL1RL2 gene encoding the corresponding extracellular domain of human IL1RL2 (Il1rl2/IL1RL2 exons 3-8, with intervening introns and parts of the flanking introns, respectively) (FIG. 1A). The resulting humanized gene encodes a chimeric receptor that maintains the intracellular signaling specificity of mice, while rendering the extracellular domain human and able to bind human ligands IL1F6, IL1F8, and IL1F9, also called IL36A, B and G, respectively. Homozygous humanized Il1rl2 mice are referred to as Il1rl2$^{hu/hu}$.

Figure 1B:
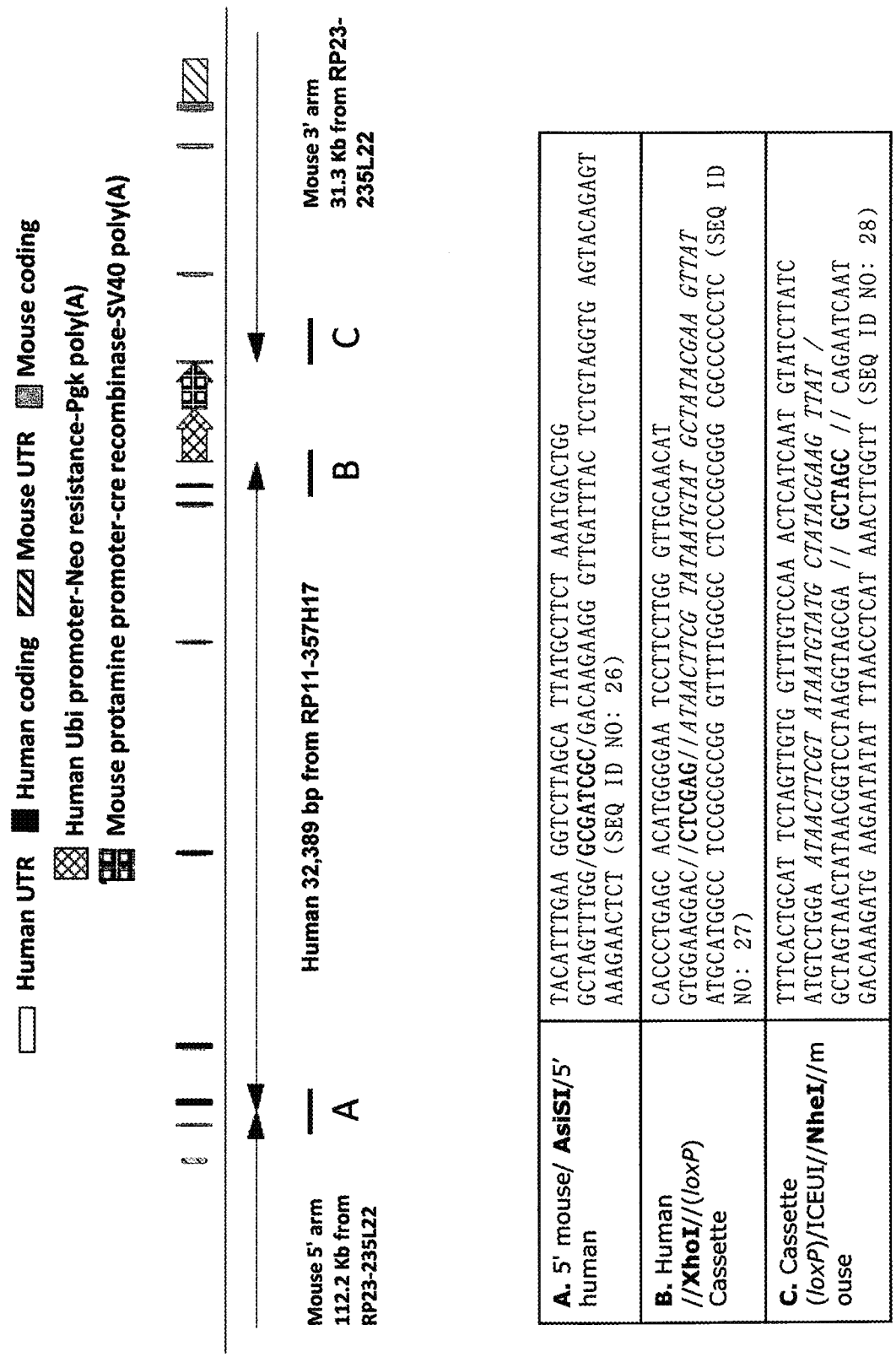

More specifically, mouse bacterial artificial chromosome (BAC) clone RP23-235L22 containing a mouse Il1rl2 gene was used and modified as follows to provide a targeting vector. A DNA fragment was generated to include a 5' mouse homology nucleotide sequence, a human IL1RL2 genomic DNA of about 32,389 bp (containing 3' 346 bp of intron 2, exons 3-8 with all intervening introns, and 5' 1101 bp of intron 8), a self-deleting neomycin cassette of about 4,996 bp, and a 3' mouse homology sequence (FIG. 1B). This DNA fragment was used to modify BAC clone RP23-235L22 through homologous recombination in bacterial cells. As a result, an ectodomain-encoding mouse Il1rl2 genomic fragment (of about 25,324 bp, including the 3' 155 bp of mouse intron 2, exons 3 through 8 with all intervening introns, and the 5' 642 bp of mouse intron 8) in the BAC clone was replaced with the human IL1RL2 genomic DNA, followed by the self-deleting neomycin cassette (FIG. 1B). The resulting modified BAC clone included, from 5' to 3', (i) a 5' mouse homology arm containing about 112.2 kb of mouse genomic DNA, mouse Il1rl2 exons 1-2 and a 5' portion of intron 2, (ii) a human IL1RL2 genomic fragment including a 3' portion of intron 2, exons 3 through 8, and a 5' portion of intron 8; (iii) a self-deleting neomycin cassette of about 4,996 bp, followed by (iv) a 3' mouse homology arm of 31.3 kb containing the remaining mouse Il1rl2 exons downstream of exon 8, all the intervening introns and the 3' UTR. See FIG. 1B. The junction sequences are also set forth at the bottom of FIG. 1B.

Figure 1C:
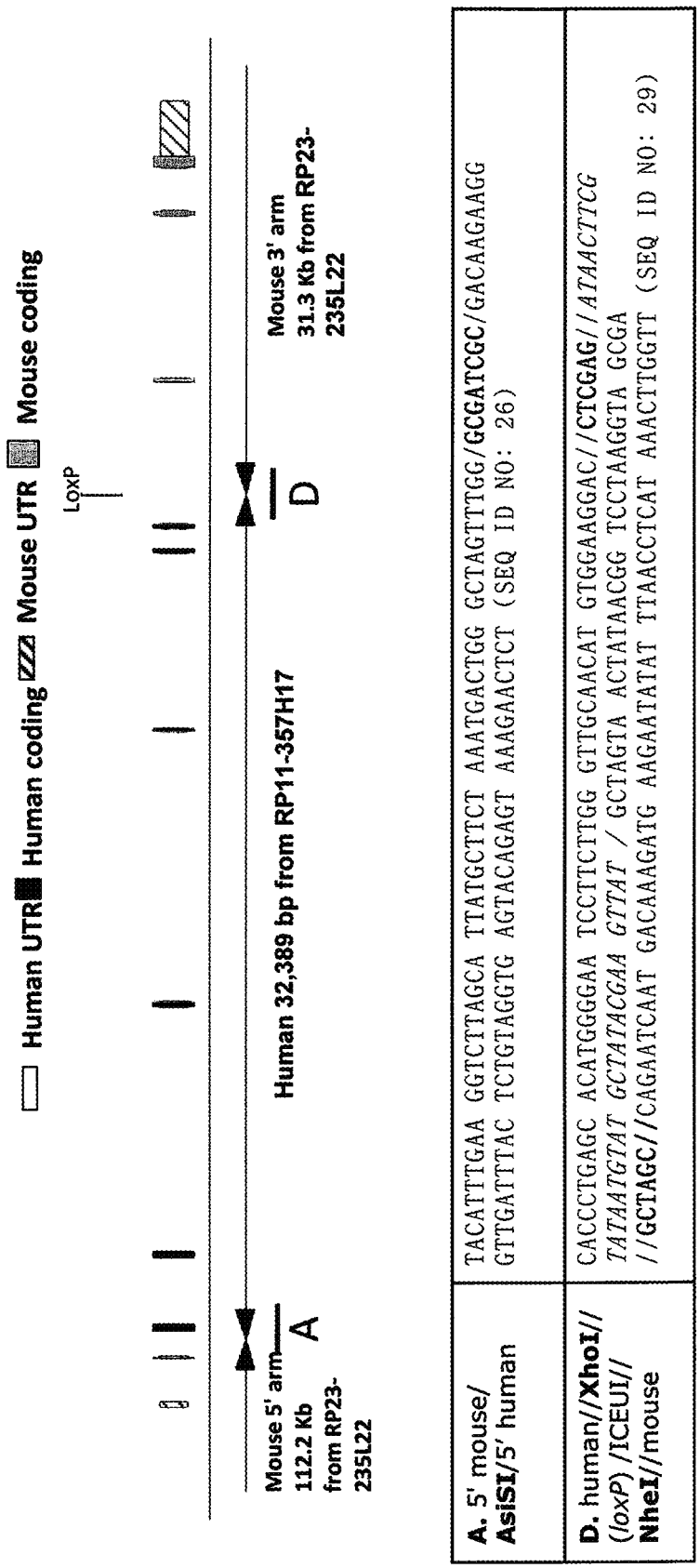

The modified BAC clone containing the humanized Il1rl2 gene, as described above, was used as a targeting vector to electroporate mouse F1H4 embryonic stem cells (50% C57BL/6NTac/50% 129S6/SvEvTac) to create modified ES cells comprising a humanized Il1rl2 gene. Positively targeted ES cells containing a humanized Il1rl2 gene were identified by an assay (Valenzuela et al., supra) that detected the presence of the human IL1RL2 sequences and confirmed the loss and/or retention of mouse Il1rl2 sequences. The primers and probes that were used to confirm humanization as described above were set forth in Table 5. Once a correctly targeted ES cell clone has been selected, the neomycin selection cassette can be excised. The humanized Il1rl2 locus after the deletion of the cassette is depicted in FIG. 1C, with the junction sequences also shown in FIG. 1C.

TABLE 5

| | | | Mouse TaqMan Loss of allele assays |
|---|---|---|---|
| 7252mTU | Fwd | | GGGTCCATTATTTGAGACTTTCCA (SEQ ID NO: 34) |
| | Probe | (BHQ) | AGCTTTCTGCTGGCCCCATTACTTG (SEQ ID NO: 35) |
| | Rev | | GCATGTGCCTGTCTTCACA (SEQ ID NO: 36) |
| 7252mTD | Fwd | | GAGTGGTACAACCTCTACATTTGAG (SEQ ID NO: 37) |
| | Probe | (BHQ) | CTGCAGCCTTCCCTGGTTGGTTC (SEQ ID NO: 38) |
| | Rev | | AGTGGGCAGCTCCCTTTAGA (SEQ ID NO: 39) |
| | | | Human TaqMan Gain of allele assays |
| 7252hTU | Fwd | | CCCACTGCATGTGAAGCAT (SEQ ID NO: 40) |
| | Probe | (BHQ) | TTGAGTGTCTGCACCTGAGCCA (SEQ ID NO: 41) |
| | Rev | | GGAGACCTCTTATTAGCCTGTGA (SEQ ID NO: 42) |
| 7252hTD | Fwd | | CACCTGCCCTAAGTCATCTC (SEQ ID NO: 43) |
| | Probe | (BHQ) | TACAGCAAGAGCAGAGGCCACA (SEQ ID NO: 44) |
| | Rev | | GCCTGCAGAGAAGCAATGTTC (SEQ ID NO: 45) |

Selected ES cell clones were microinjected into 8-cell embryos from Charles River Laboratories Swiss Webster albino mice, yielding F0 VelociMice® that were 100% derived from the targeted cells (Poueymirou et al. 2007, supra). Mice bearing a humanized locus were again confirmed and identified by genotyping of DNA isolated from tail snips using a modification of allele assay (Valenzuela et al., supra) that detected the presence of the human gene sequences. Animals homozygous for a humanized locus were made by crossing heterozygous animals.

Figure 1D:
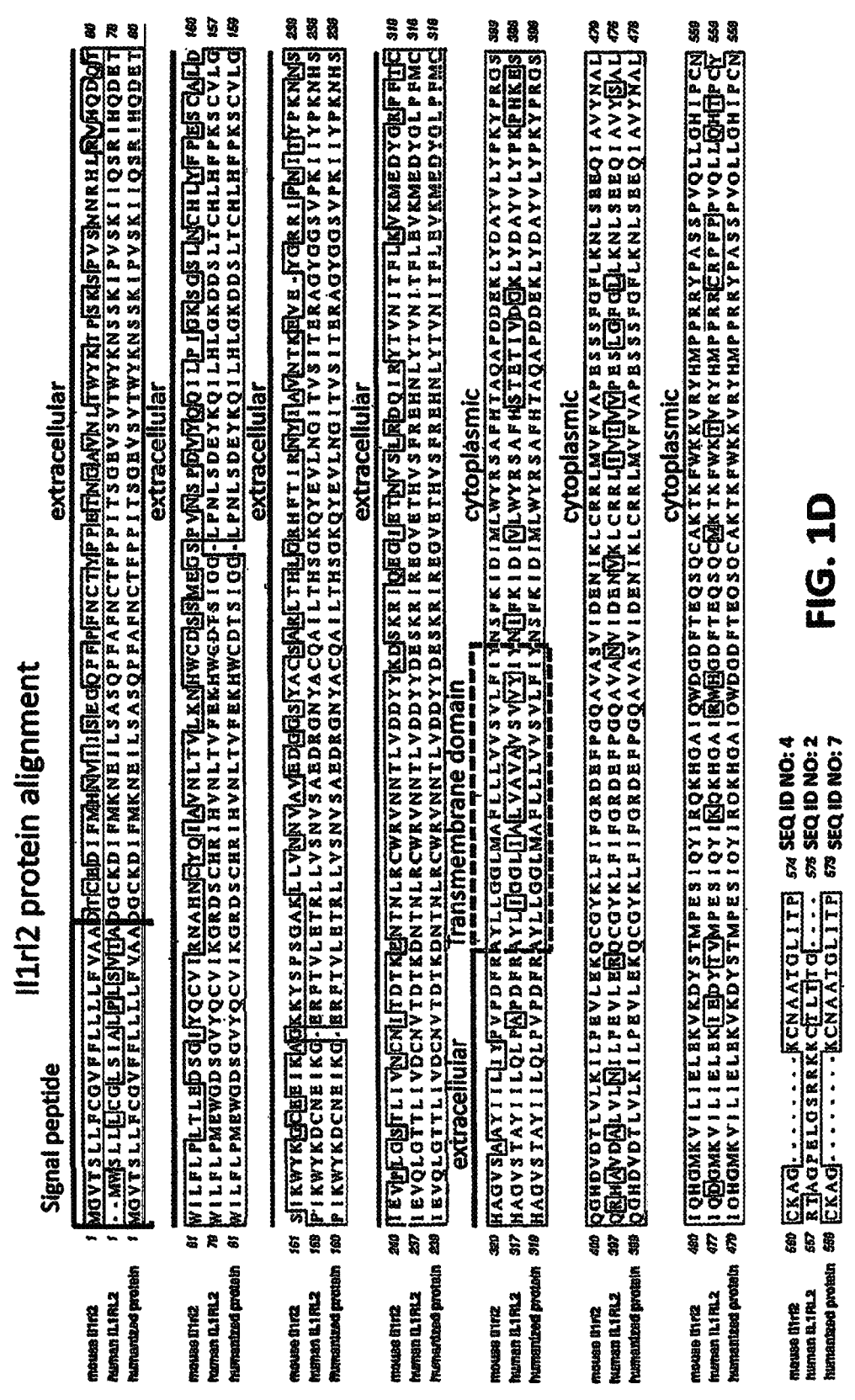

An alignment of the amino acid sequences of the resulting humanized/chimeric Il1rl2 receptor (SEQ ID NO: 7), mouse Il1rl2 protein (SEQ ID NO: 4), and human IL1RL2 protein (SEQ ID NO: 2), is provided in FIG. 1D.

Generation of a Triple-Humanized Mouse Strain

A "triple-humanized" strain was generated in which the complete coding sequence of each of the mouse Il1f6, Il1f8, and IL1f9 genes was replaced with the complete coding sequence of each of the human IL1F6, IL1F8, and IL1F9 genes, respectively. This strategy resulted in humanized genes encoding human ligands that are able to bind the human extracellular domain of the chimeric Il1rl2 receptor. Homozygous humanized Il1f6, Il1f8, Il1f9 mice are referred to as Il1f6$^{hu/hu}$, Il1f8$^{hu/hu}$, Il1f9$^{hu/hu}$.

Figure 2A:
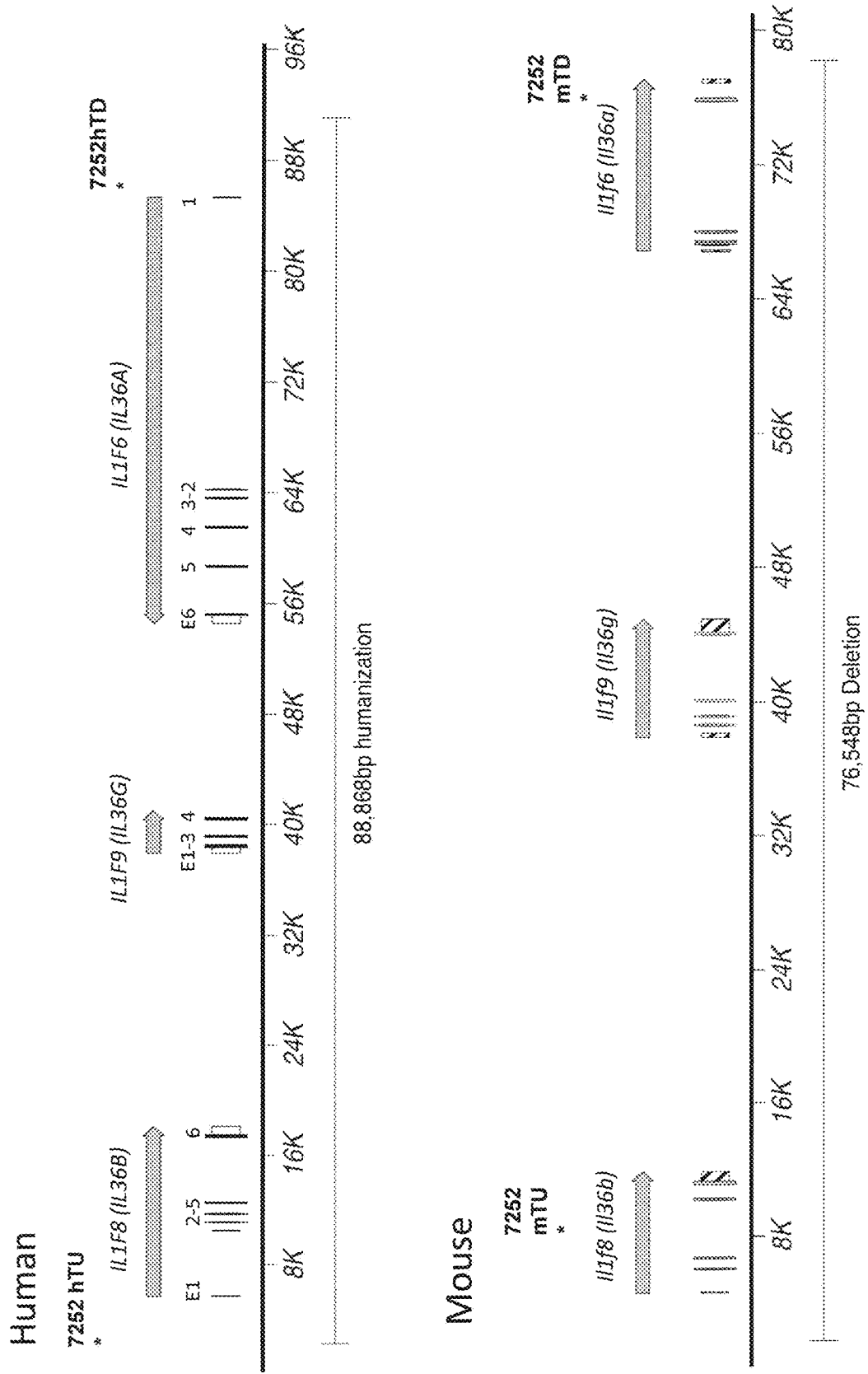
Figure 2B:
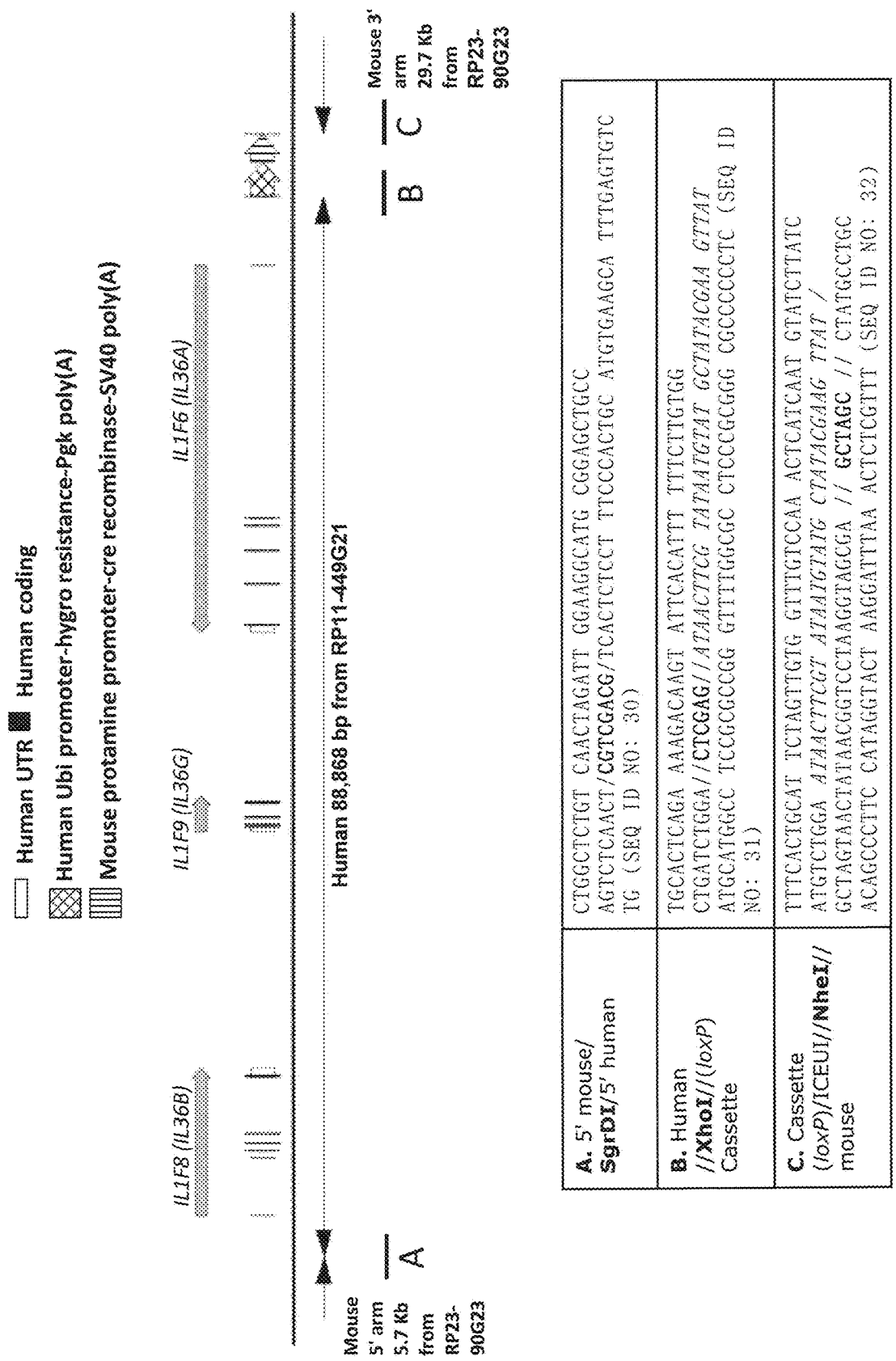

More specifically, mouse bacterial artificial chromosome (BAC) clone RP23-90G23 containing mouse Il1f8, Il1f9, and Il1f6 genes and intergenic sequences was used and modified as follows to provide a targeting vector. A DNA fragment was generated to include a 5' mouse homology nucleotide sequence, a human genomic DNA of about 88,868 bp (containing the promoters, untranslated regions, and coding sequences for human IL1F8, IL1F9, and IL1F6), a self-deleting hygromycin cassette of about 5,218 bp, and a 3' mouse homology sequence (FIG. 2B). This DNA fragment was used to modify BAC clone RP23-90G23 through homologous recombination in bacterial cells. As a result, a mouse genomic fragment of about 76,548 bp in the BAC clone was replaced with the human genomic DNA, followed by the self-deleting cassette (FIGS. 2A-2B). The resulting modified BAC clone included, from 5' to 3', (i) a 5' mouse homology arm containing about 5.7 kb of mouse genomic DNA, (ii) a human genomic fragment of about 88,868 bp (containing the promoters, untranslated regions, and coding sequences for human IL1F8, IL1F9, and IL1F6), (iii) a self-deleting hygromycin cassette of about 5,218 bp, and (iv) a 3' mouse homology sequence of about 29.7 kb. See FIG. 2B. The junction sequences are also set forth at the bottom of FIG. 2B.

Figure 2C:
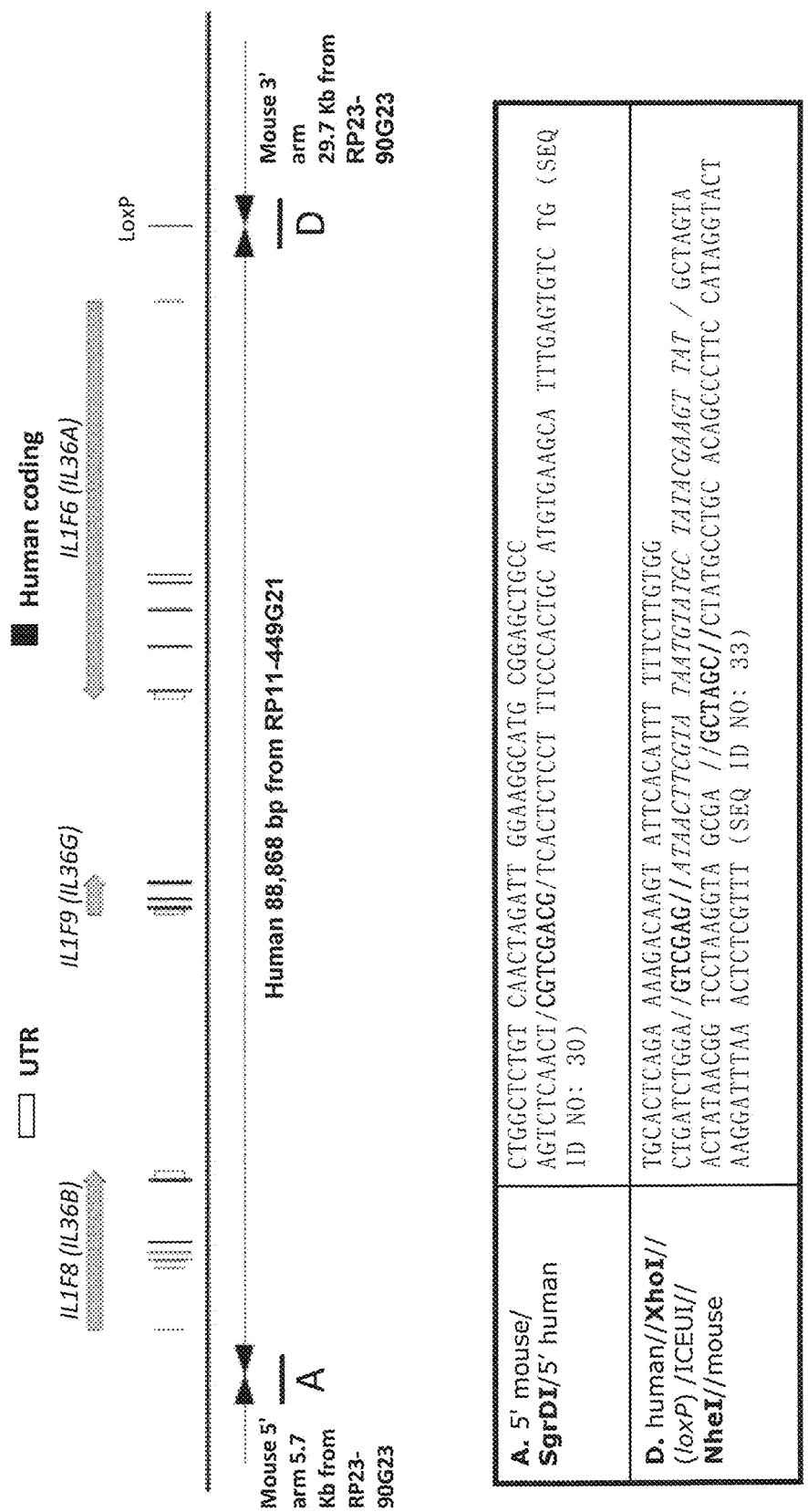

The modified BAC clone containing the human IL1F8, IL1F9, and IL1F6 gene sequences, as described above, was used as a targeting vector to electroporate mouse F1H4 embryonic stem cells (50% C57BL/6NTac/50%129S6/SvEvTac) to create modified ES cells comprising human IL1F8, IL1F9, and IL1F6 gene sequences. Positively targeted ES cells containing human IL1F8, IL1F9, and IL1F6 gene sequences were identified by an assay (Valenzuela et al., supra) that detected the presence of the human sequences and confirmed the loss and/or retention of mouse sequences. The primers and probes that were used to confirm humanization as described above were set forth in Table 6. Once a correctly targeted ES cell clone has been selected, the hydromycin selection cassette can be excised. The humanized locus after the deletion of the cassette is depicted in FIG. 2C, with the junction sequences also shown in FIG. 2C.

TABLE 6

| | | | Mouse TaqMan Loss of allele assays |
|---|---|---|---|
| 7210U | Fwd | | CAGCCGCTACACACCACAA (SEQ ID NO: 46) |
| | Probe | (BHQ) | CCAGCTGCTACACAAATGCAGGGC (SEQ ID NO: 47) |
| | Rev | | CGTCATCTCCTGCCAGTTCA (SEQ ID NO: 48) |
| 7210D | Fwd | | CTGCTGCTCAGAGCATTGAAA (SEQ ID NO: 49) |
| | Probe | (BHQ) | CCATGGCCAGGGAAGGCTTACTA (SEQ ID NO: 50) |
| | Rev | | CGCCTCCGACTGAACATATGAC (SEQ ID NO: 51) |
| | | | Human TaqMan Gain of allele assays |
| 7210hU | Fwd | | CCTGATATGCATCTTTCCCTATGGA (SEQ ID NO: 52) |
| | Probe | (BHQ) | ATGGCACCTCAGACCAGACCCAC (SEQ ID NO: 53) |
| | Rev | | GGCAGCAATAATACTGGGACAAAC (SEQ ID NO: 54) |
| 7210hD | Fwd | | GGCCAGGAAACACATCTGAAG (SEQ ID NO: 55) |
| | Probe | (BHQ) | AGCAGTGACTCTAAATGCTCAGTGTGA (SEQ ID NO: 56) |
| | Rev | | GCCTCACTCCAACAACATTATGA (SEQ ID NO: 57) |

Selected ES cell clones were microinjected into 8-cell embryos from Charles River Laboratories Swiss Webster albino mice, yielding F0 VelociMice® that were 100% derived from the targeted cells (Poueymirou et al. 2007, supra). Mice bearing a humanized locus were again confirmed and identified by genotyping of DNA isolated from tail snips using a modification of allele assay (Valenzuela et al., supra) that detected the presence of the human gene sequences. Animals homozygous for a humanized locus were made by crossing heterozygous animals.

Generation of a Triple-Humanized Mouse Strain

A "quadruple-humanized" strain was generated by crossing the single-humanized and triple-humanized strains together, bred to homozygosity for both loci on a 100% C57BL/6NTac background. Homozygous quadruple-humanized strain is referred to as Il1rl2$^{hu/hu}$ Il1f6$^{hu/hu}$ Il1f8$^{hu/hu}$ Il1f8$^{hu/hu}$, or a "DITRA-like" mouse. Neo and hygro cassettes were deleted in the F0 germline by self-deleting technology.

Example 2. Characterization of DITRA Mice

Materials and Methods

Acute and Chronic IMQ-Induced Skin Inflammation Induction and Antibody Treatment in DITRA-Like Mice To induce skin inflammation, 8-10 weeks old humanized DITRA-like female mice had their back hair shaved using mouse hair trimmer (Oster, MiniMax, Cat #78049-100) and skin depilated with 0.5 g Veet hair removal gel three days prior to IMQ cream application. A daily topical dose of 62.5 mg of commercially available IMQ cream (5%) (Aldara, GM Health Care Limited, NDC 99207-206-12, lot # QJ044A) or Vaseline (CVS Pharmacy, NDC 59779-902-88) was applied on the shaved back skin of the mice for four consecutive days for acute and nine days for chronic disease induction. A daily topical dose of 62.5 mg of Aldara translated into a daily dose of 3.125 mg of an active compound. In acute IMQ-induced skin inflammation, an anti-human IL-36R antibody was administered subcutaneously into back skin at 10 mg/kg 3 days before and 1 day after starting IMQ application. Control group received PBS and 10 mg/kg of hIgG4 Isotype control injections. In chronic IMQ-induced skin inflammation, the same anti-human IL-36R antibody was administered subcutaneously into back skin at 10 mg/kg therapeutically on days 4 and 8 after starting IMQ application. Two or three days after treatments, the back skin of mice started to display signs of erythema, scaling and thickening. The severity of inflammation was measured on a daily basis using an adapted version of the clinical Psoriasis Area and Severity Index. Erythema, scaling and thickening were scored independently on a scale from 0-4: 0, none; 1, slight; 2, moderate; 3, marked; and 4, very marked (van der Fits et al., J Immunol 2009, 182:5836-5845, which is herein incorporated by reference in its entirety). On day 4 of acute and day 11 of chronic IMQ-induced skin inflammation, skin thickness was measured using caliper (Kaefer).

Histopathology

Skin tissues of 6 mm diameter from murine back were fixed in 10% buffered formalin, and 4-5 μm paraffin embedded sections were stained with hematoxylin and eosin. Skin sections were evaluated blindly for the presence of parakeratosis, orthokeratosis, Munro's microabscess, acanthosis, epidermal ulceration, inflammation in the dermis and hypodermis, blood vessel congestion in the dermis and hypodermis, follicular hyperkeratosis and epithelial hyperplasia. A 0-4 scoring scale was used: 0-within normal limits, 1-minimal, 2-mild, 3-moderate and 4-severe (van der Fits et al., J Immunol 2009, 182:5836-5845, which is incorporated herein by reference in its entirety). A total pathology score was calculated for each mouse by adding the individual histopathological feature scores. Data analysis was performed using GraphPad Prism™ software.

Measurement of Cytokines in Skin Homogenates

Full thickness skin tissues of 6 mm diameter from murine back were taken and placed in 15 mL tube containing T-per buffer (Thermo Scientific, Cat #378510, lot # RF236217), 1× Halt Protease Inhibitor Cocktail (Thermo Scientific, Cat #87786, lot # QG221763) and 5M EDTA Solution (Thermo Scientific, Cat3 78429). Skin tissues were disrupted at 28000 rpm for 1 minute using a Polytron (PT10-35 GT-D, Cat #9158158) and put on ice. Generated skin homogenates were centrifuged at 1500 rpm for 8 minutes at 4° C. and the supernatants were collected into 96-well plates. Skin homogenates were subjected to Bradford protein assay using protein assay dye (BioRad, Cat #500-0006, lot #210008149) to quantify the total protein content. Cytokine concentrations in the skin homogenates were measured using a Proinflammatory Panel 1 (mouse) multiplex immunoassay kit (MesoScale Discovery, Cat # K15048D) according to manufacturer's instructions. In brief, 50 μL/well of calibrators and samples (diluted in Diluent 41) were added to the plates pre-coated with capture antibodies and incubated at room temperature while shaking at 700 rpm for 2 hours. The plates were then washed 3 times with 1×PBS containing 0.05% (w/v) Tween-20, followed by the addition of 25 μL of Detection Antibody Solution diluted in Diluent 45. After 2-hour incubation at room temperature while shaking, the plates were washed 3 times, and 150 μL of 2× Read Buffer was added to each well. Electrochemiluminescence was immediately read on a MSD Spector® instrument. Data analysis was performed using GraphPad Prism™ software. Cytokine levels were normalized to total protein content.

Induction of DSS-Induced Model of Chronic Colitis and Antibody Treatment in DITRA-Like Mice To induce chronic DSS-mediated colitis, female DITRA-like mice aged 12-20 weeks with an average body weight of more than 23 g were given 1.5-3% DSS (Sigma-Aldrich Cat #87786, lot # PJ203966B) in drinking water for 7 days followed by distilled water for 11-13 days. A second cycle of DSS treatment (for 4 days) followed by water (5-6 days) was performed until day 27-30. Control group received distilled water for the duration of the study. Anti-human IL-36R and mIL-12p40 (Bioxcell Cat # BE0051, clone C17.8) antibodies were administered intraperitoneally at 10 mg/kg be-weekly starting on day 7. Control group received PBS and respective hIgG4 and ratIgG2a (Bioxcell Cat # BE0089, clone 2A3) Isotype control injections at 10 mg/kg. Mice were weighted and monitored for clinical signs of colitis (e.g. stool consistency and fecal blood) on a daily basis. On day 27-30, mice were euthanized and colon lengths were measured. To evaluate DSS colitis, the following features were scored: inflammation (severity and extent), epithelial changes (erosion/ulcer), changes in the crypts (crypt loss, cryptitis/crypt abscess, regeneration/hyperplasia, goblet cell loss), submucosal edema and percentage of tissue area with pathology relative to the total tissue area on the slide. A 0-4 scoring scale was used: 0-0-within normal limits, 1-minimal, 2-mild, 3-moderate and 4-severe. A total pathology score was calculated for each mouse by adding the individual histopathological feature scores.

Measurement of Lcn-2 in Fecal Samples

To monitor intestinal inflammation throughout the study, feces from individual DITRA-like mice were collected into 2 mL deep well plates on a weekly basis and stored at −80°

C. Upon the completion of the study, feces collected on different days were subjected to homogenization. In brief, fecal samples were reconstituted with 1 mL PBS containing 0.1% Tween-20, 1× Halt Protease Inhibitor Cocktail (Thermo Scientific, Cat #87786, lot # QG221763) and 5M EDTA Solution (Thermo Scientific, Cat3 78429). After adding 2 Tungsten 3 mm Carbide Beads to the wells (Qiagen, Cat #69997), the plates were placed on a shaker at highest speed overnight at 4° C. Homogenous fecal suspensions were centrifuged at 1200 rpm for 10 minutes at 4° C. and the supernatants were collected into 96-well plates. Fecal Lipocalin-2 (Lcn2) levels were measured using mouse Duoset Lipocalin-2/NGAL ELISA kit (R&D Systems, Cat # DY1857, lot # P116359) according to manufacturer's instructions. Data analysis was performed using GraphPad Prism™ software.

Measurement of Myeloperoxidace (MPO) Activity in Colon Homogenates

Pieces of distal part of the colon were taken into 2 mL microcentrifuge tubes containing 2 Tungsten 3 mm Carbide Beads (Qiagen, Cat #69997) containing T-per buffer (Thermo Scientific, Cat #378510, lot # RF236217), lx Halt Protease Inhibitor Cocktail (Thermo Scientific, Cat #87786, lot # QG221763) and 5M EDTA Solution (Thermo Scientific, Cat #78429). Colon tissues were disrupted using Qiagen Tissue Lyser II at frequency of 27.5 $s^{-1}$ for 10 minutes. Tubes were centrifuged at 1500 rpm for 8 minutes at 4° C. and the supernatants were collected into 96-well plates. Colon homogenates were subjected to Bradford protein assay using protein assay dye (BioRad, Cat #500-0006, lot #210008149) to quantify the total protein content. Myeloperoxidase (MPO) activity in the colon homogenates was measured using mouse MPO ELISA Kit (Hycult Biotech, Cat # HK210-02, lot #21022KO617-Y) according to manufacturer's instructions. Data analysis was performed using GraphPad Prism™ software. MPO levels were normalized to total protein content.

Measurement of Cylokines in Colon Homogenates

Cytokine concentrations in the colon homogenates were measured using a Proinflammatory Panel 1 (mouse) multiplex immunoassay kit (MesoScale Discovery, Cat # K15048D) according to manufacturer's instructions. In brief, 50 μL/well of calibrators and samples (diluted in Diluent 41) were added to the plates pre-coated with capture antibodies and incubated at room temperature while shaking at 700 rpm for 2 hours. The plates were then washed 3 times with 1×PBS containing 0.05% (w/v) Tween-20, followed by the addition of 25 μL of Detection Antibody Solution diluted in Diluent 45. After 2-hour incubation at room temperature while shaking, the plates were washed 3 times, and 150 μL of 2× Read Buffer was added to each well. Electrochemiluminescence was immediately read on a MSD Spector® instrument. Data analysis was performed using GraphPad Prism™ software. Cytokine levels were normalized to total protein content.

Statistical Analysis

Statistical significance within the groups was determined by one-way Anova with Tukey's multiple comparison post-test (*$p<0.05$, $p<0.005$, *$p<0.0005$, ****$p<0.0001$) (same for both *—statistical significance from PBS-treated group and #-statistical significance from corresponding Isotype-treated group).

Results

Humanized DITRA-Like Mice Exhibit Enhanced Skin Inflammation in IMQ-Induced Model of Psoriasis To interrogate the role of deregulated IL-36R signaling similar to GPP or DITRA (for "Deficiency of Interleukin Thirty-six Receptor Antagonist") patients, mice were generated to have humanized IL-36R (e.g., Il1rl2) and human IL-36α, β, γ ligands, but not the IL-36Ra antagonist, as described in Example 1. The resulting hIL-36R/hIL-36α, β, γ mice were referred to as DITRA-like mice due to a 20-fold decreased affinity of mouse IL-36Ra for human IL-36R leading to an enhanced IL-36R signaling similar to DITRA patients (for a more detailed discussion of DITRA patients, see, e.g., Marrakchi et al., N Engl J Med 2011, 365:620-628, which is herein incorporated by reference in its entirety).

In an unchallenged state, DITRA-like mice did not develop any spontaneous diseases. In contrast, in the preclinical model of IMQ-induced psoriasiform dermatitis that closely resembles human psoriasis lesions in terms of the phenotypic and histological characteristics (for a more detailed discussion regarding characterization of psoriasiform dermatitis, see van der Fits et al., J Immunol 2009, 182:5836-5845; Swindell et al., PLoS One 2011, 6: e18266, all of which are herein incorporated by reference in their entireties), DITRA-like mice displayed an enhanced skin inflammation compared to their WT littermates (FIGS. 3A-3B). In brief, IMQ was applied daily to the shaved back skin of DITRA-like and WT mice for four consecutive days. On day 5 skin was harvested for subsequent histopathological evaluation, protein and RNA isolation. IMQ-treated DITRA-like mice developed more severe psoriasis lesions such as scaling, erythema and skin thickening compared to WT littermates (FIG. 3A). Consistent with clinical features, histopathological evaluation of the skin revealed more enhanced acanthosis, parakeratosis and disturbed keratinocyte differentiation in DITRA-like mice (FIG. 3B). IMQ-treated DITRA-like mice also displayed significantly increased numbers of Munro's abscesses or pustules similarly to patients with GPP. Moreover, IMQ application led to increased levels of pro-inflammatory molecules deregulated in psoriasis (pro-inflammatory molecules including, e.g., IL-17a, IL-17f, IL-23a, S100A8, Defb4) in the skin of DITRA-like mice compared to WT littermates (FIG. 3C). Further, IL-36α, IL-36β, and IL-36γ mRNA expression were equally increased in IMQ-treated DITRA-like mice and IMQ-treated wild type mice as compared to Vaseline treated DITRA-like mice and Vaseline treated wild type mice, respectively; however, protein levels of IL-36α and IL-36β cytokines were detected at 2-fold higher concentrations in the inflamed skin of DITRA-like mice as compared to the levels in the inflamed skin of wild type mice.

Figures 4A, 4B:
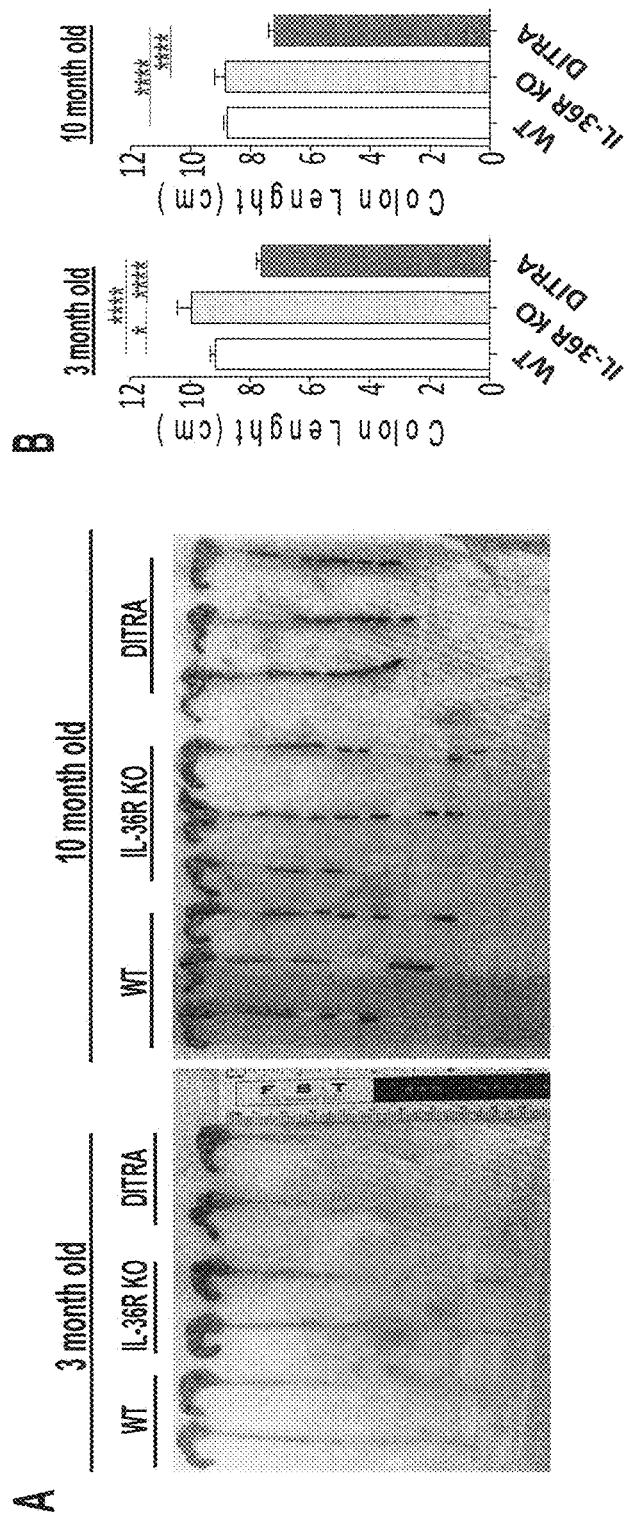
FIGS. 4A-4B. In some embodiments, DITRA-like mice display shortened colons at steady state. (4A) Representative pictures of colons isolated from DITRA-like mice and their co-housed IL-36R KO and WT littermates at 3 and 10 months. (4B) Quantified colon length of 3 and 10 month old DITRA-like mice compared to their co-housed IL-36R KO and WT littermates (n=6 per each group). Error bars represent mean±SD.

Humanized DITR4-Like Mice Display a Defect in Mucosal Healing in DSS-Induced Model of Chronic Colitis In recent years, several studies in subsets of patients demonstrated deregulated expression of IL-36 axis in IBD and its possible contribution to the intestinal inflammation. Expression of IL-36α and IL-36γ was shown to be elevated in inflamed mucosa of patients with ulcerative colitis (see Medina-Contreras et al., J Immunol 2016, 196:34-38; Nishida et al., Inflamm Bowel Dis 2016, 22:303-314, and Russell, Mucosal Immunol 2016, 9:1193-1204, which are all herein incorporated by reference in their entireties). In preclinical models, IL-36R deficiency protected from DSS- and Oxazolone-induced colitis (Medina-Contreras et al., J Immunol 2016, 196:34-38; Harusato et al., Mucosal Immunol 2017, 10:1455-1467, which are all herein incorporated by reference in their entireties). At steady state, DITRA-like mice did not develop spontaneous ileitis/colitis, but displayed significantly shortened colons at both young and old age (3 and 10 month old, respectively) (FIGS. 4A and 4B). In addition, at steady state and as compared to wild type mice, DITRA-like mice exhibited elevated levels of IL-36 cytokines, as well as a trend towards increased IL-17F and IL-17A levels, and reduced L-21 levels, in the colon.

Figures 5A, 5B, 5C:
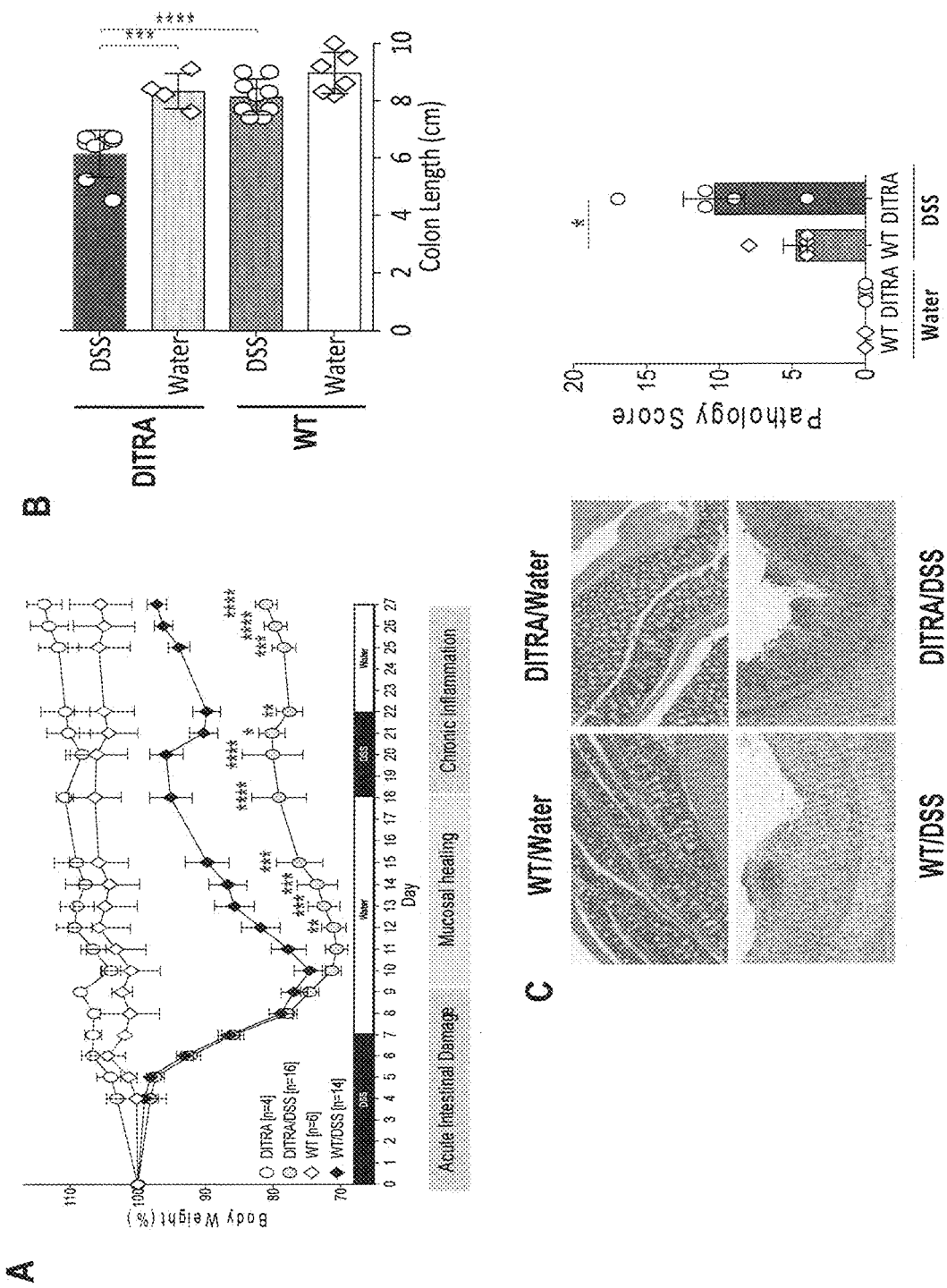
FIGS. 5A-5E. In some embodiments, DITRA-like mice exhibit a defect in mucosal healing in DSS-induced chronic colitis. DITRA-like mice (n=16) and their co-housed WT littermate controls (n=14) were subjected to chronic DSS-induced colitis by administrating 2.5% DSS for 7 days followed by water for 11 days and 1.5% DSS for 4 days followed by water for 5 days for a total of 27 days. Control mice (n=5) received regular water. (5A) Body weight loss in DITRA-like mice and their WT co-housed littermate controls calculated as the percent difference between the original and actual body weight on any particular day. (5B) Colon length in water- and DSS-treated DITRA-like and WT mice. (5C) Haemotoxylin and eosin (H&E) staining and pathology score of the colon of water- and DSS-treated DITRA-like and WT mice. (5D) Myeloperoxidase (MPO) activity in colon homogenates in water- and DSS-treated DITRA-like and WT mice. (5E) Levels of pro-inflammatory cytokines in colon homogenates in water- and DSS-treated DITRA-like and WT mice. Data are representative of at least three independent experiments. Error bars represent mean±SD. In each group of bars from left to right are: WT/water, DITRA/water, WT/DSS, and DITRA/DSS.
Figures 5D, 5E:
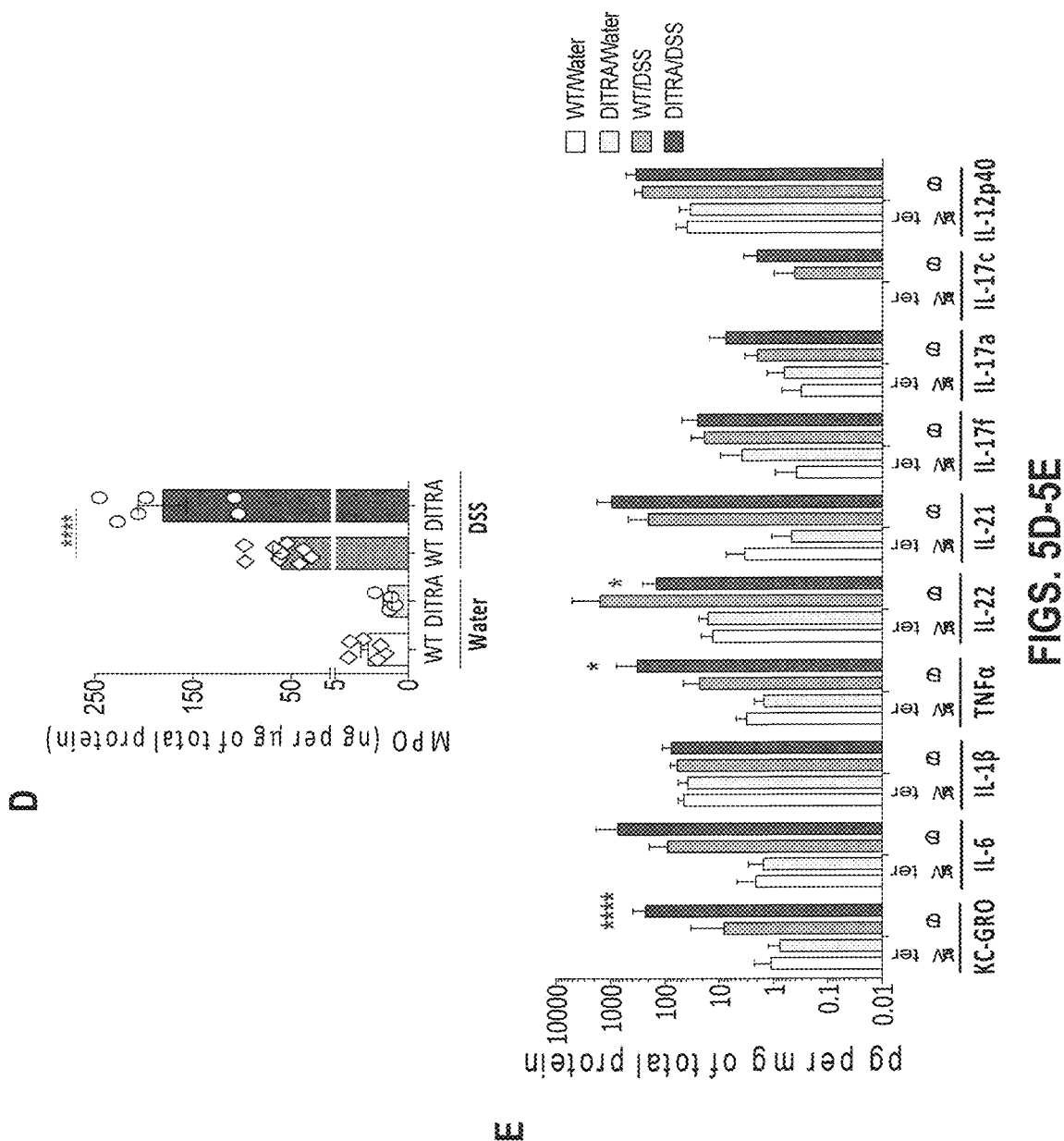

To evaluate the role of IL-36 axis in intestinal inflammation, a chemically induced model of intestinal injury was used by utilizing oral administration of DSS that damages the colonic epithelium (Okayasu et al., Gastroenterology 1990, 98:694-702, herein incorporated by reference in its entirety) and triggers potent inflammatory responses (Rakoff-Nahoum et al., Cell 2004, 118: 229-241, herein incorporated by reference in its entirety) exhibiting main features of IBD, in particular ulcerative colitis. DITRA-like mice and their co-housed WT littermates were subjected to DSS-induced chronic colitis regimen by administration of 2.5% DSS for 7 days followed by 11 days of water (first cycle) and 1.5% DSS for 4 days followed by 5 days of water (second cycle). In the acute phase of the disease, DITRA-like mice developed intestinal inflammation similarly to co-housed WT littermates (FIG. 5A). Interestingly, in the repair phase of the disease, DITRA-like mice showed inability to recover from DSS-induced mucosal damage reflected in the sustained body weight loss (FIG. 5A), significantly reduced colon length (FIG. 5B), more severe pathology score (associated with more severe ulceration, extensive epithelial erosion and neutrophilic infiltration) (FIG. 5C), significantly increased fecal Lipocalin-2 (Lcn2) levels and myeloperoxidase activity (FIG. 5D), up-regulation of pro-inflammatory cytokines such as KC-GRO, TNF-α and IL-6, and a reduction in the L-22 levels in the colon (FIG. 5E). In addition, DITRA-like mice exhibited a death rate of about 62.5% (data not shown). By contrast, WT mice did recover in the repair phase of colitis and had a death rate of 250%. Gut epithelial integrity was also investigated by orally gavaging DITRA-like mice and wild type mice with fluorescein isothiocyanate (FITC)-dextran. A significant increase in the FITC-dextran levels was observed in the sera of DITRA-like mice at day 14 of DSS treatment, indicating that the IL-36 pathway is involved in regulating intestinal permeability during gut injury. Thus, enhanced IL-36 signaling in DITRA-like mice leads to exacerbation of intestinal inflammation and a defect in mucosal repair suggesting the role of IL-36 in regulating the mechanisms involved in intestinal tissue remodeling.

Figures 6A, 6B:
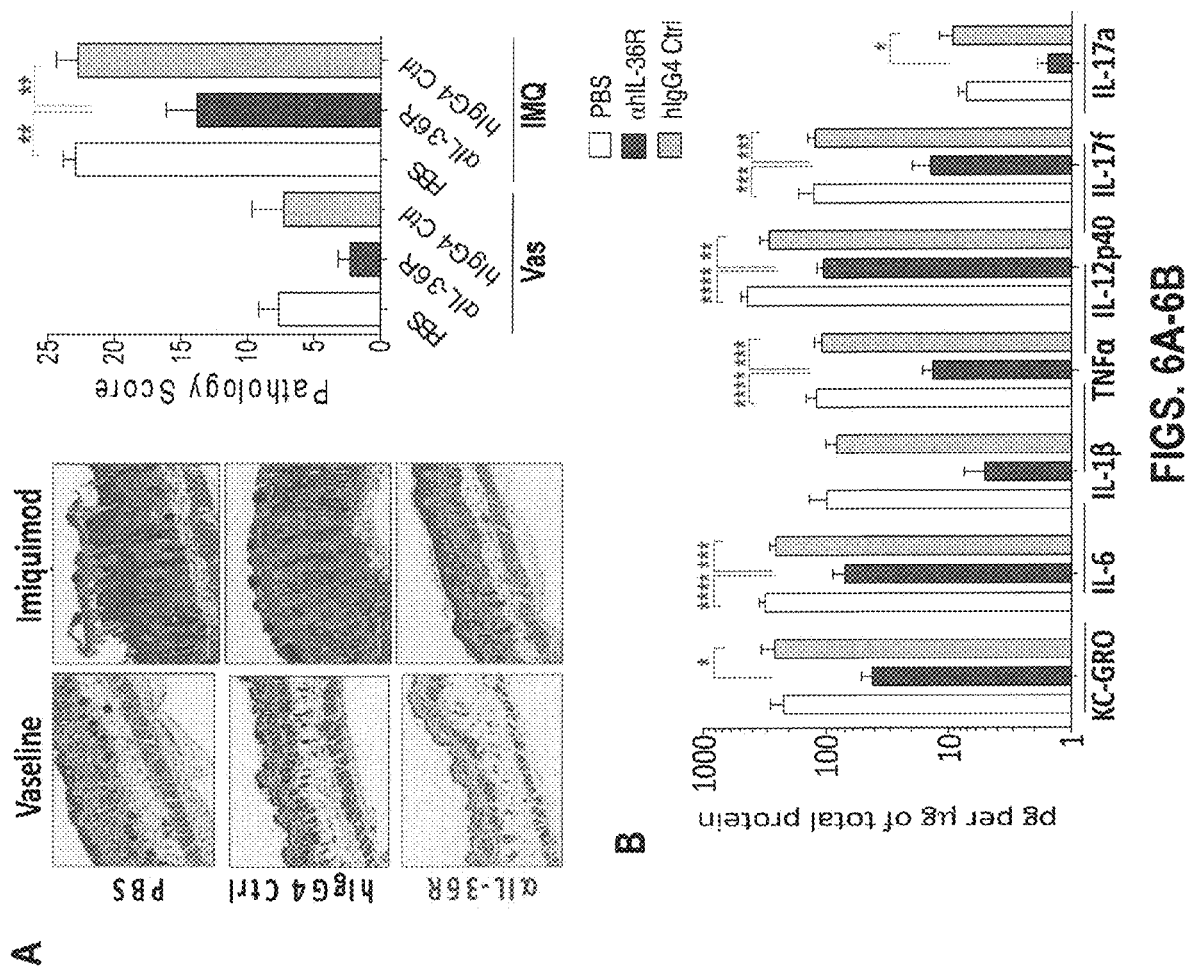
FIGS. 6A-6B. In some embodiments, human IL-36R antagonism with REGN anti-human IL-36R antibody ameliorates IMQ-induced skin inflammation in DITRA-like mice at prophylactic dosing. Skin on the back of DITRA-like mice was shaved 3 days before starting the IMQ application, and the skin was topically treated with Vaseline (control) or IMQ-containing cream (Aldara) for 4 consecutive days. PBS, αhIL-36R mAb and hIgG4 Isotype control were subcutaneously injected at 10 mg/mL on day−3 and 1 (n=9 for each treatment group). (6A) H&E histological sections and pathology score of the back skin isolated from DITRA-like mice on day 5. (6B) Levels of pro-inflammatory cytokines in the skin homogenates of DITRA-like mice on day 5 treated with daily applications of IMQ and injections of PBS, αIL-36R mAb and Isotype control on day−3 and 1. Data are representative of three independent experiments. Error bars represent mean±SD. In each group of bars from left to right are: PBS, αhIL-36R mAb, and hIgG4 isotype control.

Anti-Human IL-36R Monoclonal Antibody Inhibits Acute Skin Inflammation in DITRA-Like Mice at Prophylactic Dosing To examine the role of IL-36R in skin inflammation, an anti-human IL-36R monoclonal antibody was tested in IMQ-induced model of psoriasiform dermatitis. IMQ was applied daily to the shaved back skin of DITRA-like mice for four consecutive days. The anti-human IL-36R monoclonal antibody was administered at 10 mg/kg 3 days before (−3d) and one day after (d1) starting the IMQ application. Control groups received PBS and hIgG4 Isotype control injections at 10 mg/kg. On day 5 skin was harvested for subsequent histopathological evaluation and protein isolation. The anti-human IL-36R monoclonal antibody significantly reduced IMQ-induced total pathology score including parakeratosis and Munro's microabscess compared to PBS- and Isotype control-treated groups (FIG. 6A). Human IL-36R blockade also resulted in 66-93% reduction in KC-GRO, IL-6 and TNFα (FIG. 6B). Importantly, the anti-human IL-36R antibody treatment significantly decreased levels of pro-inflammatory cytokines deregulated in psoriasis (e.g., IL-12p40, IL-17f and IL-17α) (FIG. 6B) suggesting a tightly regulated interplay between these cytokines pathways. The observed efficacy of the anti-human IL-36R monoclonal antibody in abrogating acute IMQ-induced skin inflammation was dose-dependent, with a dose of 10 mg/kg resulting in stronger inhibition of skin inflammation as compared to a dose of 1 mg/kg, as determined based on the pathology score, skin thickness, and levels of pro-inflammatory cytokines in skin homogenates (data not shown).

Figures 7A, 7B, 7C:
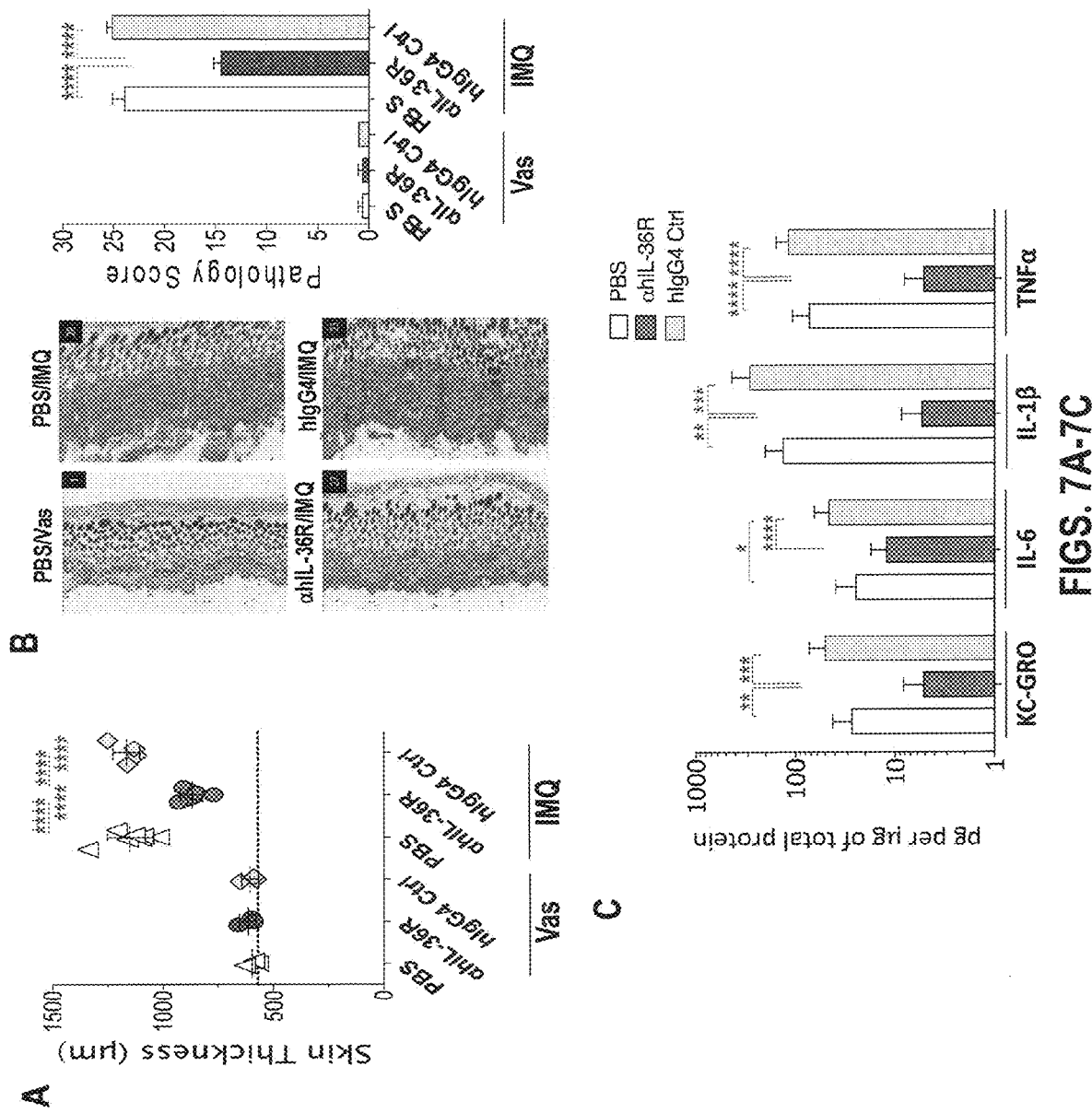
FIGS. 7A-7C. In some embodiments, therapeutic administration of anti-human IL-36R antibody ameliorates chronic IMQ-induced skin inflammation in DITRA-like mice. Skin on the back of DITRA-like mice was shaved 3 days before starting the administration, and the skin was topically treated with Vaseline (control) or IMQ-containing cream (Aldara) for two rounds (5 consecutive days with the application for a first round, followed by 2 days without the application, then a second round of 4 consecutive days with the application for a total of 11 days). PBS, anti-human IL-36R antibody and hIgG4 Isotype control were subcutaneously injected at 10 mg/mL on days 5 and 9 (n=10 for each treatment group). (7A) Skin thickness was measured in DITRA-like mice on day 12. Thickness is presented in μm. (7B) H&E histological sections and pathology score of the skin from DITRA-like mice on day 12. (7C) Levels of pro-inflammatory cytokines were measured in the skin homogenates of DITRA-like mice on day 12. Data are representative of two independent experiments. Error bars represent mean±SD. In each group of bars from left to right are: phosphate buffered saline (PBS), αhIL-36R mAb, and hIgG4 isotype control.

Anti-Human IL-36R Monoclonal Antibody Inhibits Chronic Skin Inflammation at Therapeutic Dosing To further examine the therapeutic efficacy of human IL-36R antagonism in vivo, the same anti-human IL-36R monoclonal antibody was tested in chronic IMQ-induced model of skin inflammation. For the duration of two weeks, IMQ was applied to the shaved back skin of DITRA-like mice for nine days in two rounds separated by two days without the treatments. The anti-human IL-36R monoclonal antibody was administered subcutaneously at days 5 and 9 after starting IMQ application at 10 mg/kg dose. Control groups received PBS and hIgG4 Isotype control injections at 10 mg/kg. On day 12 skin thickness was measured and tissues harvested for subsequent histopathological evaluation and protein isolation. Similar to acute IMQ-induced inflammation, prolonged IMQ application led to upregulation of proinflammatory mediators in the skin of DITRA-like mice (data not shown). The anti-human IL-36R monoclonal antibody showed a significant efficacy in reducing IMQ-induced skin thickness and pathology lesion scores in DITRA-like mice (FIGS. 7A and 7B, respectively). In addition, administration of the anti-human IL-36R monoclonal antibody led to a significant inhibition of IMQ-induced production of pro-inflammatory cytokines in the skin of DITRA-like mice (FIG. 7C).

Altogether, the data demonstrated prophylactic and therapeutic efficacy of an anti-human IL-36R antibody in ameliorating acute and chronic IMQ-induced skin inflammation in vivo.

Figures 8A, 8B:
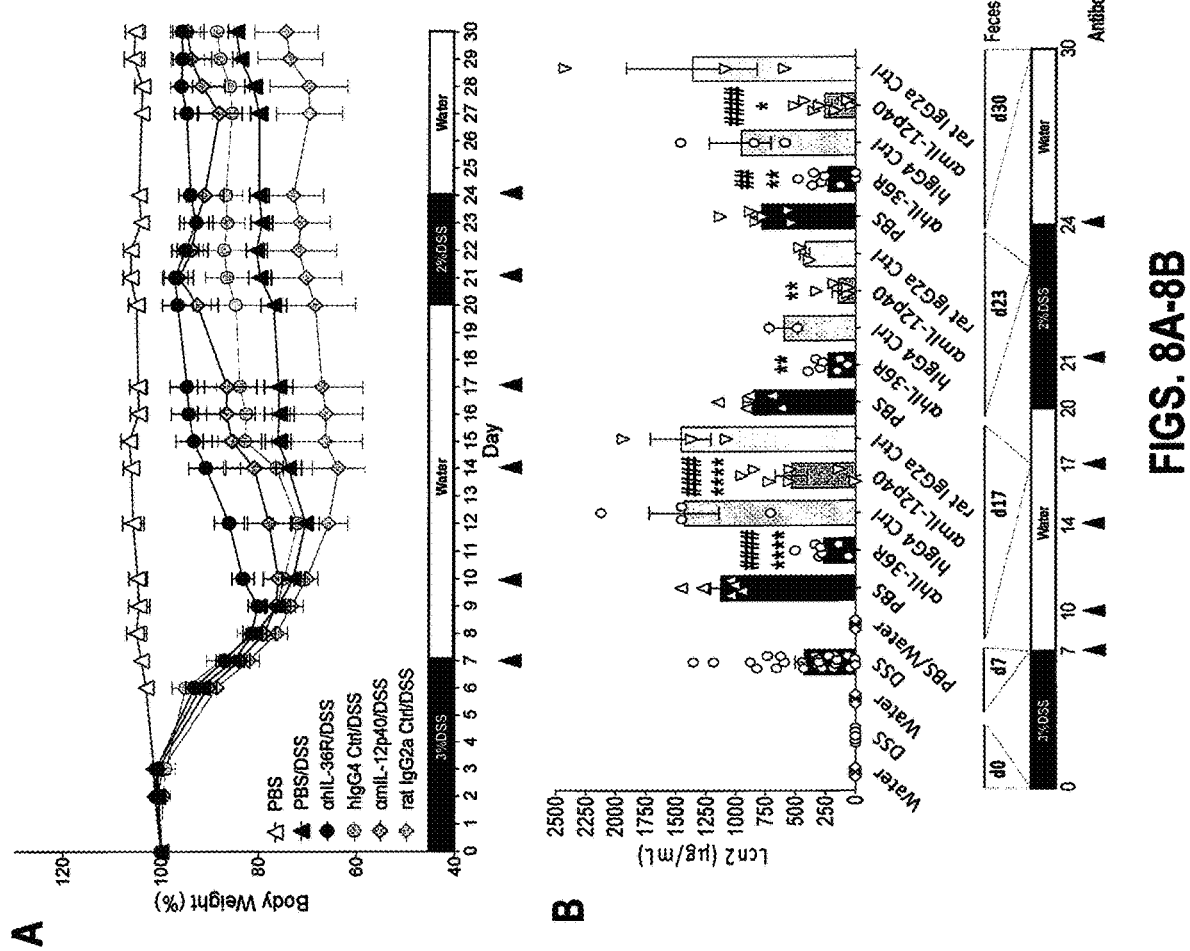
FIGS. 8A-8E. In some embodiments, therapeutic administration of anti-human IL-36R antibody, similarly to IL-12p40 blockade, ameliorates DSS-induced chronic inflammation in DITRA-like mice and rescues their inability to heal from DSS-induced mucosal damage. DITRA-like mice (n=45) were subjected to chronic DSS-induced colitis by administrating 3% DSS for 7 days and 2% DSS for 13 days followed by water for the total of 30 days. Control mice (n=5) received regular water. PBS (n=11), αIL-36R mAb (n=11), hIgG4 Isotype control (n=6), αmIL-12p40 (Biox-Cell) (n=11) and rat IgG2a Isotype control (n=6) were intraperitoneally injected at 10 mg/mL on day 7, 10, 14, 17, 21 and 24. (8A) Body weight loss in DITRA-like mice calculated as the percent difference between the original and actual body weight on any particular day. (8B) Levels of fecal lipocalin-2 (Lcn2) in DITRA-like mice measured on day 0, 7, 17, 23 and 30 throughout the chronic colitis. (8C) Colon length in DITRA-like mice on day 30. (8D) Myeloperoxidase (MPO) activity in colon homogenates of DITRA-like mice at day 30. (8E) Levels of pro-inflammatory cytokines in colon homogenates in DITRA-like mice on day 30. Data are representative of two independent experiments. Error bars represent mean±SD. In each group of bars from left to right are: PBS/water, PBS/DSS, αhIL-36R/DSS, hIgG4 isotype control/DSS, αmIL-12p40/DSS, and rat IgG2a isotype control/DSS.
Figures 8C, 8D, 8E:
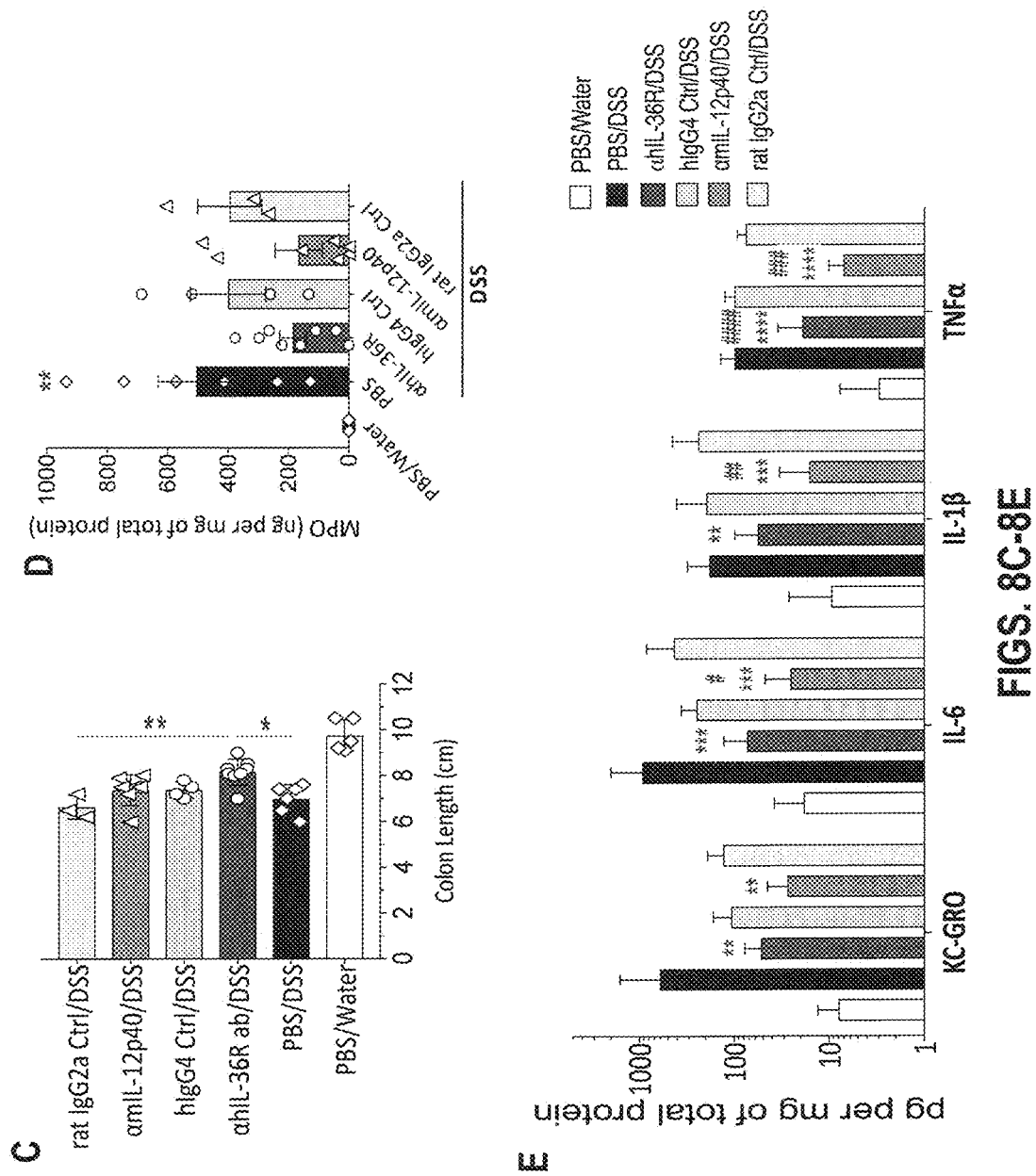

Anti-Human IL-36R Monoclonal Antibody Ameliorates DSS-Induced Chronic Colitis in DITRA-Like Mice at Therapeutic Dosing Having demonstrated the defect in mucosal healing as a result of enhanced IL-36 signaling in DITRA-like mice, it was further investigated as to whether Il-36 blockade would rescue the observed phenotype. DITRA-like mice were subjected to chronic DSS-induced colitis by administration of 3% DSS for 7 days followed by 13 days of water for two cycles. The same anti-human IL-36R monoclonal antibody and an anti-mIL-12p40 monoclonal antibody (a mouse surrogate for Ustekinumab which is approved for treating Crohn's disease) were administered at 10 mg/kg bi-weekly starting on day 7. Control groups received PBS and corresponding hIgG4 and rat IgG2a Isotype control injections at 10 mg/kg. Treatment with the anti-human IL-36R monoclonal antibody rescued the inability of DITRA-like mice to recover from DSS-induced mucosal damage and reduced the disease severity compared to PBS and Isotype control treatments in DITRA-like mice (FIG. 8A). To monitor the intestinal inflammation at different stages of the disease, feces from individual mice were collected on a weekly basis to measure fecal Lipocalin-2 (Lcn2) protein, a non-invasive biomarker of inflammation in intestinal injury (procedure described in, e.g., Thorsvik et al., J Gastroenterol Hepatol 2017, 32:128-135, which is herein incorporated by reference in its entirety). As shown in FIG. 8B, PBS-, hIgG4- and rat IgG2a-treated groups displayed significant upregulation of fecal Lcn2 levels on day 17, 23 and 30 compared to water alone. Administrations of the anti-human IL-36R monoclonal antibody surprisingly resulted in a significant reduction in Lcn2 levels compared to PBS- and Isotype-treated groups. Sustained reduction of fecal Lcn2 levels was observed in anti-human IL-36 antibody-treated groups at day 17, 23 and 30 (FIG. 8B).

Further results included that the hIL-36R blockade with the anti-human IL-36R monoclonal antibody led to an increase in colon length (FIG. 8C) and decrease in myeloperoxidase (MPO) activity (FIG. 8D) and 61-95% reduction in pro-inflammatory cytokines (FIG. 8E) in the colon of DSS-treated DITRA-like mice. The anti-human IL-36R monoclonal displayed comparable efficacy with IL-12p40 blockade in ameliorating DSS-induced chronic colitis as reflected in similarly decreased levels of fecal Lcn2, MPO activity and pro-inflammatory cytokines in the colon of DITRA-like mice (FIGS. 8A-8E).

IL-36R Blockade in Oxazolone-Induced Colitis

Figures 9A, 9B, 9C:
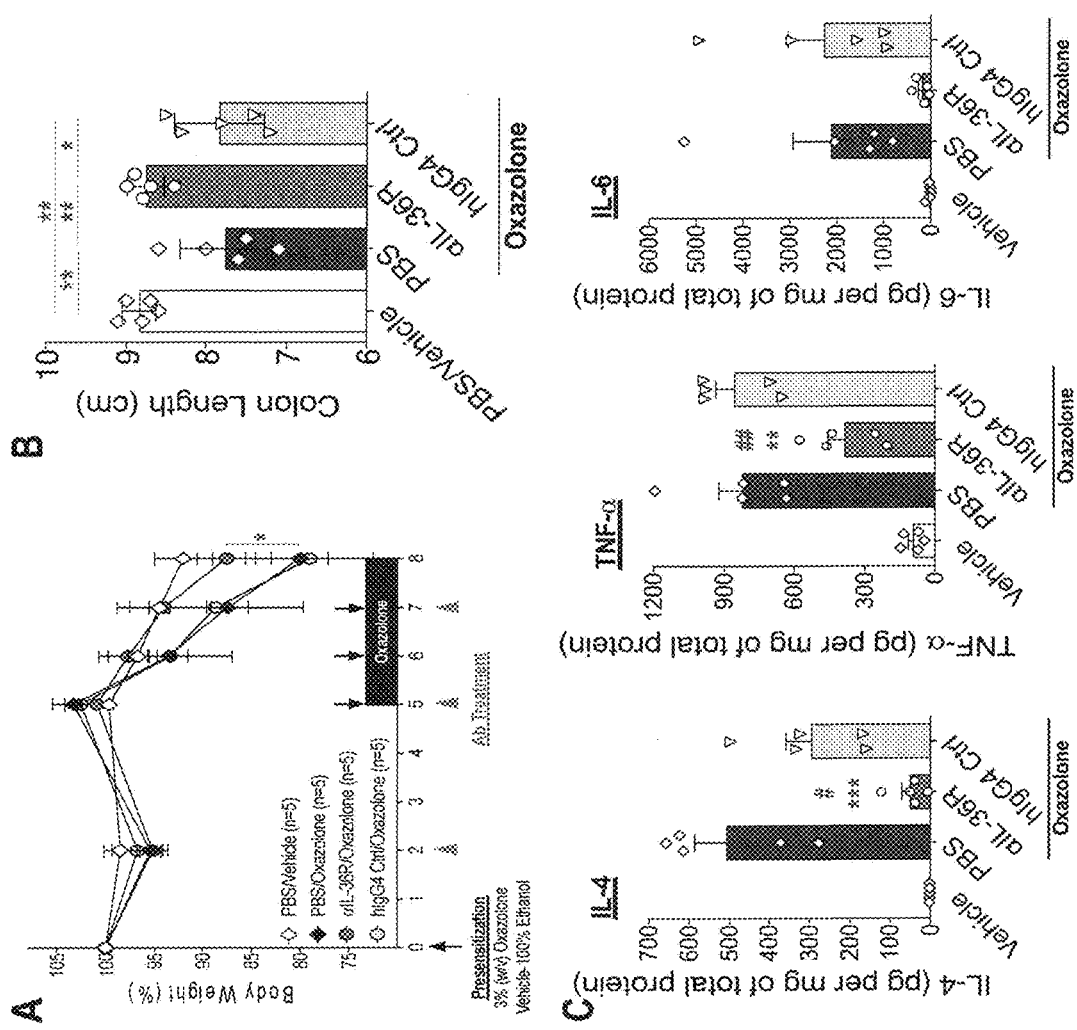
FIGS. 9A-9C. Human IL-36R antagonism ameliorates oxazolone-induced colitis in DITRA-like mice. DITRA-like mice were pre-sensitized with 3% solution of oxazolone dissolved in 100% Ethanol and intrarectally administered with 1.5% oxazolone and vehicle (50% Ethanol) on days 5, 6 and 7. Mice were intraperitoneally injected with PBS, anti-human IL-36R mAb and hIgG4 isotype control on days 2, 5 and 7 after pre-sensitization. (A) Body weight of PBS-, anti-human IL-36R mAb- and hIgG4 control-treated DITRA-like mice during oxazolone administration. *p<0.05 from PBS-treated group. (B) Colon length measured on day 8 in DITRA-like mice. (C) Levels of proinflammatory cytokines in colon homogenates in oxazolone- and vehicle-treated DITRA-like mice injected with PBS, anti-human IL-36R mAb and hIgG4 isotype control. *—represents significance from PBS-treated group, #—significance from isotype-treated group. Data are representative of two independent experiments with 5 mice per group. Error bars represent mean±SEM. *p<0.05, p<0.005, *p<0.0005, ****p<0.00001.

The efficacy of IL-36R blockade was tested in oxazolone-induced colitis, another preclinical model of IBD with the histologic resemblance to human ulcerative colitis (Heller et al., Immunity 17, 629-638 (2002), which is incorporated in its entirety by reference). Prophylactic administration of anti-human IL-36R antibody significantly reduced oxazolone-induced disease severity in DITRA-like mice compared to PBS and isotype control treated groups, as reflected in average body weight loss and average colon length (FIGS. 9A-9B). In addition, IL-36R antagonism led to significantly reduced levels of IL-4 and TNF-α in the colon of oxazolone-treated DITRA-like mice (FIG. 9C).

Various publications, including patents, patent applications, published patent applications, accession numbers, technical articles and scholarly articles are cited throughout the specification. Each of these cited publications is incorporated by reference, in its entirety and for all purposes, in this document.

---

The invention claimed is:

1. A genetically modified mouse whose genome comprises:
   (1) a humanized interleukin-1 receptor-like 2 (Il1rl2) gene, wherein the humanized Il1rl2 gene
      (i) encodes a humanized Il1rl2 protein that comprises the ectodomain of a human IL1RL2 protein and the transmembrane-cytoplasmic domains of a mouse Il1rl2 protein;
      (ii) results from a replacement of a genomic fragment of an endogenous mouse Il1rl2 gene encoding the ectodomain of an endogenous mouse Il1rl2 protein with a nucleotide sequence of a human IL1RL2 gene encoding the ectodomain of the humanized Il1rl2 protein; and
      (iii) is operably linked to the endogenous mouse Il1rl2 promoter;
   (2) a human interleukin-1 family member 6 (IL1F6) gene, which replaces the endogenous mouse Il1f6 gene;
   (3) a human interleukin-1 family member 8 (IL1F8) gene, which replaces the endogenous mouse Il1f8 gene; and
   (4) a human interleukin-1 family member 9 (Il1F9) gene, which replaces the endogenous mouse Ilf9 gene;
   wherein the mouse expresses the humanized Il1rl2 protein, human IL1F6, human IL1F8, and human IL1F9.

2. The genetically modified mouse of claim 1, wherein the humanized Il1rl2 protein comprises the amino acid sequence as set forth in SEQ ID NO: 7.

3. The genetically modified mouse of claim 1, wherein the humanized Il1rl2 gene comprises exons 1-2 of the endogenous mouse Il1rl2 gene, exons 3-8 of the human IL1RL2 gene, and exons 9-11 of the endogenous mouse Il1rl2 gene.

4. The genetically modified mouse of claim 1, wherein the mouse is homozygous for the humanized Il1rl2 gene, human IL1F6 gene, human IL1F8 gene and human IL 1F9 gene.

5. An isolated cell or tissue obtained from the mouse of claim 1, wherein the isolated cell or tissue comprises the humanized Il1rl2 gene, the human IL 1F6 gene, the human IL1F8 gene, and the human IL1f9 gene.

6. A method of determining whether a compound is capable of inhibiting inflammation, the method comprising:
   administering an agent to the mouse of claim 1 to induce inflammation,
   administering the compound to the mouse; and
   determining whether the compound inhibits inflammation in the mouse.

7. The method of claim 6, wherein the intestinal inflammation is induced in the mouse by administering dextran sulfate sodium (DSS) or oxazolone to the mouse, and wherein the compound is administered to the rodent before, during, or after the administration of DSS or oxazolone.

8. The method of claim 6, wherein the skin inflammation is induced in the mouse by administering imiquimod (IMQ), and wherein the compound is administered to the rodent before, during, or after the administration of IMQ.

9. The method of claim 6, wherein the compound is a small molecule compound, a nucleic acid inhibitor, or an antibody.

10. The method of claim 9, wherein the compound is an antibody.

11. The method of claim 6, wherein the humanized Il1rl2 protein comprises the amino acid sequence as set forth in SEQ ID NO: 7.

12. The method of claim 6, wherein the humanized Il1rl2 gene comprises exons 1-2 of the endogenous mouse Il1rl2 gene, exons 3-8 of the human IL1RL2 gene, and exons 9-11 of the endogenous mouse Il1rl2 gene.

13. The method of claim 6, wherein the mouse is homozygous for the humanized Il1rl2 gene, human IL1F6 gene, human IL1F8 gene and human IL1F9 gene.

14. A method of making a genetically modified mouse, comprising
   (A) modifying a mouse genome to comprise
      (1) a humanized interleukin-1 receptor-like 2 (IL1rl2) gene which
         (i) encodes a humanized IL1r12 protein that comprises the ectodomain of a human IL1RL2 protein and the transmembrane-cytoplasmic domains of a mouse Il1r12 protein;
         (ii) results from a replacement of a genomic fragment of an endogenous mouse Il1r12 gene encoding the ectodomain of an endogenous mouse Il1r12 protein with a nucleotide sequence of a human IL1RL2 gene encoding the ectodomain of the humanized ILlr12 protein; and
         (iii) is operably linked to the endogenous mouse Il1r12 promoter;
      (2) a human interleukin-1 family member 6 (IL1F6) gene, which replaces the endogenous mouse Il1f6 gene;
      (3) a human interleukin-1 family member 8 (IL1F8) gene, which replaces the endogenous mouse Il1f8 gene; and
      (4) a human interleukin-1 family member 9 (IL1F9) gene, which replaces the endogenous mouse Il1f9 gene; and
   (B) making a genetically modified mouse comprising the modified genome, wherein the mouse expresses the humanized Il1rl2 protein, human IL1F6, human IL1F8, and human IL1F9.

15. The method of claim 14, wherein the mouse genome is modified by a process comprising
   (i) making a first mouse comprising the humanized Il1rl2 gene;
   (ii) making a second mouse comprising the human IL1F6 gene, the human IL1F8 gene, and the human IL1F9 gene; and
   (iii) crossing the first mouse with the second mouse to obtain the modified mouse genome.

16. The method of claim 15, wherein the mouse comprising the humanized Il1rl2 gene made by
   providing a mouse embryonic stem (ES) cell,
   replacing a genomic fragment of the endogenous mouse Il1r12 gene of the mouse ES cell with the nucleotide sequence of the human IL1RL2 gene encoding the ectodomain of the humanized IL1rl2 protein, thereby obtaining a mouse ES cell comprising the humanized Il1rl2 gene, and making a mouse using the mouse ES cell comprising the humanized Il1rl2 gene.

17. The method of claim 16, wherein the nucleotide sequence of a human IL1RL2 gene is a genomic fragment of the human IL1RL2 gene that comprises exons 3-8 of the human IL1RL2 gene.

18. The method of claim 15, wherein the second mouse comprising the human IL1F6 gene, the human IL1F8 gene, and the human IL1F9 gene is made by:

providing a mouse embryonic stem (ES) cell,
replacing:
the endogenous mouse Il1f6 gene with the human IL1F6 gene,
(ii) the endogenous mouse Il1f8 gene with the human IL1F8 gene, and
(iii) the endogenous mouse Il1f9 gene with the human IL1F9 gene,
thereby obtaining a mouse ES cell comprising the human IL1F6 gene, the human IL1F8 gene, and the human IL1F9 gene, and
making the second mouse using the mouse ES cell comprising the human IL1F6 gene, the human IL1F8 gene, and the human IL1F99 gene.

19. The method of claim 18, wherein the human IL1F6 gene, the human IL1F8 gene, and the human IL1F9 gene, are provided in a contiguous nucleic acid molecule.

20. The method of claim 14, wherein the humanized Il1rl2 protein comprises the amino acid sequence as set forth in SEQ ID NO: 7.

21. The method of claim 14, wherein the humanized Il1rl2 gene comprises exons 1-2 of the endogenous mouse Il1rl2 gene, exons 3-8 of the human IL1RL2 gene, and exons 9-11 of the endogenous mouse Il1rl2 gene.

22. An isolated mouse embryonic stem (ES) cell whose genome comprises:

(1) a humanized interleukin-1 receptor-like 2 (Il1rl2) gene, wherein the humanized Il1rl2 gene
(i) encodes a humanized Il1rl2 protein that comprises the ectodomain of a human IL1RL2 protein and the transmembrane-cytoplasmic domains of a mouse Il1rl2 protein;
(ii) results from a replacement of a genomic fragment of an endogenous mouse Il1rl2 gene encoding the ectodomain of an endogenous mouse Il1rl2 protein with a nucleotide sequence of a human IL1RL2 gene encoding the ectodomain of the humanized Il1rl2 protein; and
(iii) is operably linked to the endogenous mouse Il1rl2 promoter;
(2) a human interleukin-1 family member 6 (IL1F6) gene, which replaces the endogenous mouse Il1f6 gene;
(3) a human interleukin-1 family member 8 (IL1F8) gene, which replaces the endogenous mouse Il1f8 gene; and
(4) a human interleukin-1 family member 9 (IL1F9) gene, which replaces the endogenous mouse Il1f9 gene.

23. The isolated mouse ES cell of claim 22, wherein the humanized Il1rl2 protein comprises the amino acid sequence as set forth in SEQ ID NO: 7.

24. A mouse embryo, comprising the isolated mouse ES cell of claim 23.

25. The isolated mouse ES cell of claim 22, wherein the humanized Il1rl2 gene comprises exons 1-2 of the endogenous mouse Il1rl2 gene, exons 3-8 of the human IL1RL2 gene, and exons 9-11 of the endogenous mouse Il1rl2 gene.

26. A mouse embryo, comprising the isolated mouse ES cell of claim 25.

27. A mouse embryo, comprising the isolated mouse ES cell of claim 22.

* * * * *

UNITED STATES PATENT AND TRADEMARK OFFICE
CERTIFICATE OF CORRECTION

| | |
|---|---|
| PATENT NO. | : 11,589,562 B2 |
| APPLICATION NO. | : 16/512949 |
| DATED | : February 28, 2023 |
| INVENTOR(S) | : Andrew J. Murphy |

It is certified that error appears in the above-identified patent and that said Letters Patent is hereby corrected as shown below:

On the Title Page

Item [73], should read:
Regeneron Pharmaceuticals, Inc.,
Tarrytown, NY (US)

In the Claims

Column 85, Claim 5, Line 47 should read:
humanized Il1rl2 gene, the human IL1F6 gene, the human Column 85, Claim 5, Line 48 should read:
IL1F8 gene, and the human IL1F9 gene.

Column 86, Claim 16, Line 63 should read:
ing the humanized Il1rl2 gene is made by Column 87, Claim 18, Line 15 should read:
(i) the endogenous mouse Il1f6 gene with the human Signed and Sealed this
Sixth Day of June, 2023

Katherine Kelly Vidal
*Director of the United States Patent and Trademark Office*